(12) United States Patent
Adler et al.

(10) Patent No.: US 9,757,593 B2
(45) Date of Patent: Sep. 12, 2017

(54) RADIATION SYSTEMS WITH MINIMAL OR NO SHIELDING REQUIREMENT ON BUILDING

(71) Applicant: Varian Medical Systems, Inc., Palo Alto, CA (US)

(72) Inventors: John R. Adler, Stanford, CA (US); David H. Whittum, Sunnyvale, CA (US); Steven W. Prince, San Francisco, CA (US); James E. Clayton, Saratoga, CA (US)

(73) Assignee: Varian Medical Systems, Inc., Palo Alto, CA (US)

( * ) Notice: Subject to any disclaimer, the term of this patent is extended or adjusted under 35 U.S.C. 154(b) by 669 days.

(21) Appl. No.: 14/017,992

(22) Filed: Sep. 4, 2013

(65) Prior Publication Data

US 2014/0171725 A1    Jun. 19, 2014

Related U.S. Application Data

(60) Provisional application No. 61/697,218, filed on Sep. 5, 2012.

(51) Int. Cl.
*A61N 5/00* (2006.01)
*A61N 5/10* (2006.01)
*G21F 3/00* (2006.01)

(52) U.S. Cl.
CPC .............. *A61N 5/1082* (2013.01); *G21F 3/00* (2013.01); *A61N 2005/1094* (2013.01)

(58) Field of Classification Search
CPC ...... A61N 5/10; A61N 5/1042; A61N 5/1047; A61N 5/1049; A61N 5/1089; A61N 2005/1061; A61N 5/1067; A61B 2090/101; A61B 6/548

USPC .......................................................... 600/1–3
See application file for complete search history.

(56) References Cited

U.S. PATENT DOCUMENTS

| | | |
|---|---|---|
| 3,082,322 A | 3/1963 | Koerner et al. |
| 3,488,495 A | 1/1970 | Schneeman |
| 3,588,499 A | 6/1971 | Pegrum |
| 4,977,585 A | 12/1990 | Boyd |
| 5,420,427 A | 5/1995 | Morgan et al. |
| 5,537,452 A | 7/1996 | Shepherd et al. |

(Continued)

FOREIGN PATENT DOCUMENTS

| | | |
|---|---|---|
| CN | 2533895 Y | 2/2003 |
| FR | 1 587 608 A | 3/1970 |

OTHER PUBLICATIONS

Definition of Capsule from dictionary.com printed from internet Dec. 26, 2016.*

(Continued)

*Primary Examiner* — Samuel Gilbert
(74) *Attorney, Agent, or Firm* — Vista IP Law Group, LLP

(57) ABSTRACT

A radiation system includes: a first support; a first structure rotatably coupled to the first support so that the first structure is rotatable about a first axis relative to the first support; a second structure rotatably coupled to the first structure so that the second structure is rotatable about a second axis that forms a non-zero angle relative to the first structure; and a first radiation source connected to the second structure; wherein the first structure and the second structure are parts of a capsule for accommodating at least a portion of a patient.

20 Claims, 38 Drawing Sheets

(56) References Cited

U.S. PATENT DOCUMENTS

| | | | |
|---|---|---|---|
| 5,751,781 A | 5/1998 | Brown et al. | |
| 5,993,373 A * | 11/1999 | Nonaka | A61N 5/10 250/492.1 |
| 6,104,779 A | 8/2000 | Shepherd et al. | |
| 6,198,957 B1 | 3/2001 | Green | |
| 6,217,214 B1 | 4/2001 | Cabral et al. | |
| 6,325,538 B1 | 12/2001 | Heesch | |
| 6,888,919 B2 | 5/2005 | Graf | |
| 6,977,987 B2 * | 12/2005 | Yamashita | A61N 5/10 378/64 |
| 7,188,999 B2 * | 3/2007 | Mihara | A61N 5/10 378/17 |
| 7,295,648 B2 | 11/2007 | Brown | |
| 7,302,038 B2 | 11/2007 | Mackie et al. | |
| 7,526,066 B2 | 4/2009 | Koshnitsky et al. | |
| 7,649,981 B2 | 1/2010 | Seppi et al. | |
| 8,664,618 B2 * | 3/2014 | Yao | A61N 5/1082 250/393 |
| 9,308,395 B2 | 4/2016 | Adler, Jr. et al. | |
| 2005/0197564 A1 | 9/2005 | Dempsey | |
| 2005/0236588 A1 | 10/2005 | Ein-Gal | |
| 2009/0110146 A1 | 4/2009 | Sliski et al. | |
| 2010/0002829 A1 | 1/2010 | Dafni | |
| 2010/0239066 A1 | 9/2010 | Fahrig et al. | |
| 2011/0210261 A1 | 9/2011 | Maurer, Jr. | |

OTHER PUBLICATIONS

International Search Report and Written Opinion dated Feb. 5, 2013 for related PCT Patent Application No. PCT/US2012/067453.
First Chinese Office Action and Search Report dated Dec. 28, 2015, for related Chinese Patent Application No. 201280068583.0, 13 pages.
Extended European Search Report dated Dec. 23, 2014 for related EP Patent Application No. 12854268.5, 9 pages.
Non-final Office Action dated Jan. 24, 2014 for related U.S. Appl. No. 13/310,582.
Final Office Action dated Aug. 27, 2014 for related U.S. Appl. No. 13/310,582.
Advisory Action dated Nov. 21, 2014 for related U.S. Appl. No. 13/310,582.
Non-final Office Action dated Apr. 6, 2015 for related U.S. Appl. No. 13/310,582.
Final Office Action dated Sep. 11, 2015 for related U.S. Appl. No. 13/310,582.
Notice of Allowance and Fee(s) due dated Dec. 4, 2015 for related U.S. Appl. No. 13/310,582.
Communication pursuant to Article 94(3) EPC dated Sep. 20, 2016, for related European Patent Application No. 12 854 268.5, 4 pages.
Notification of Second Office Action dated Aug. 25, 2016 for related Chinese Patent Application No. 201280068583.0, 6 pages.

* cited by examiner

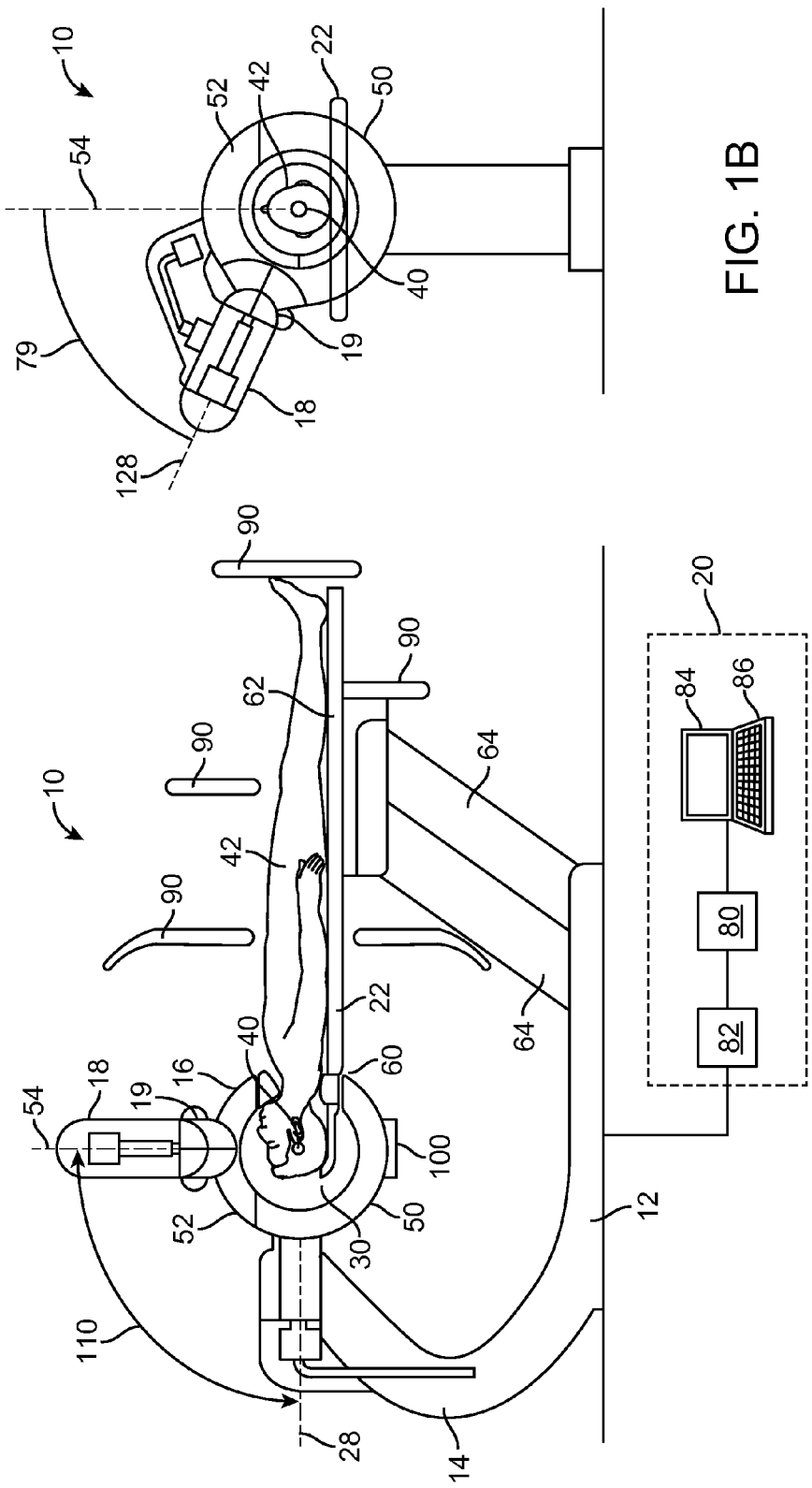

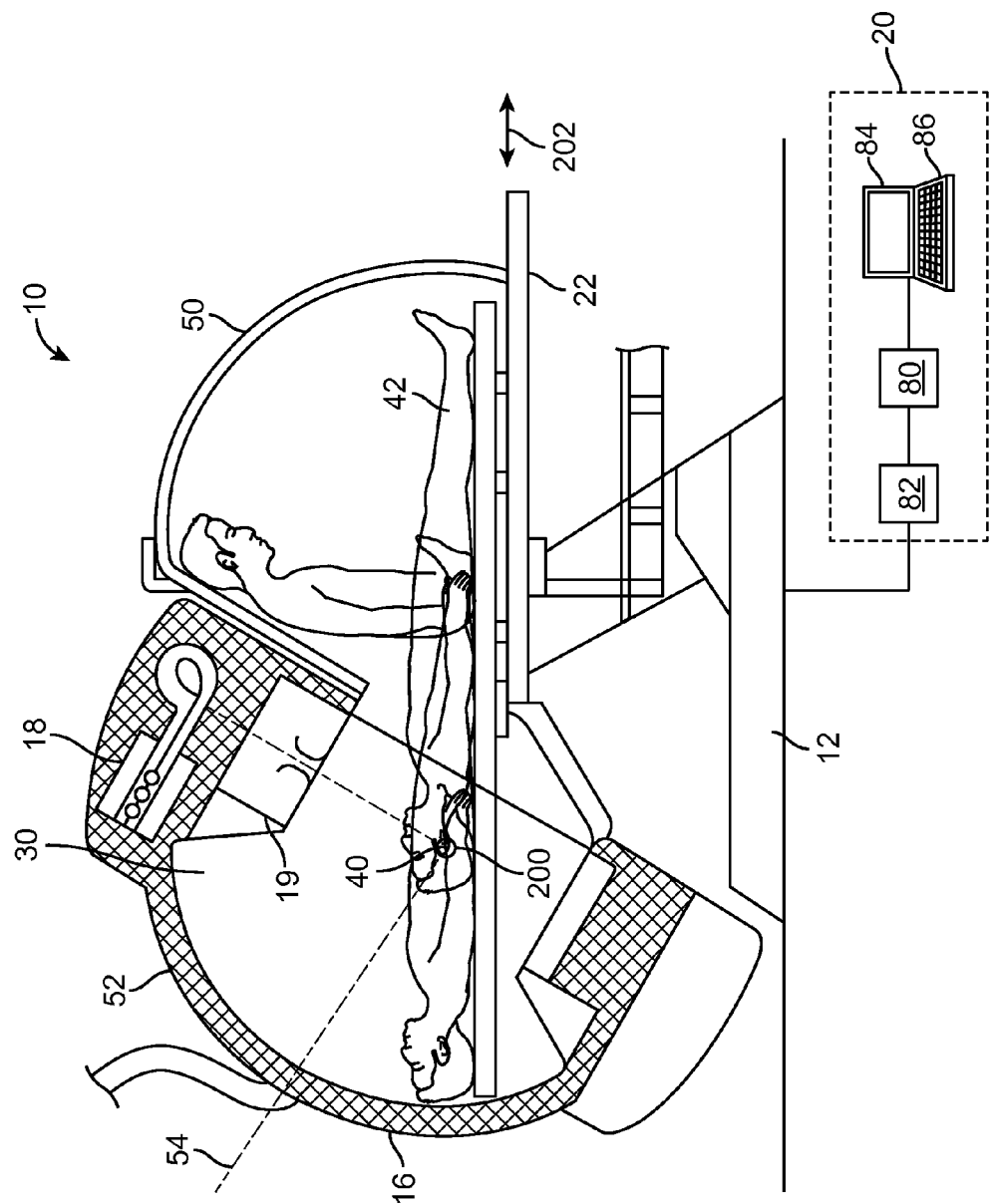

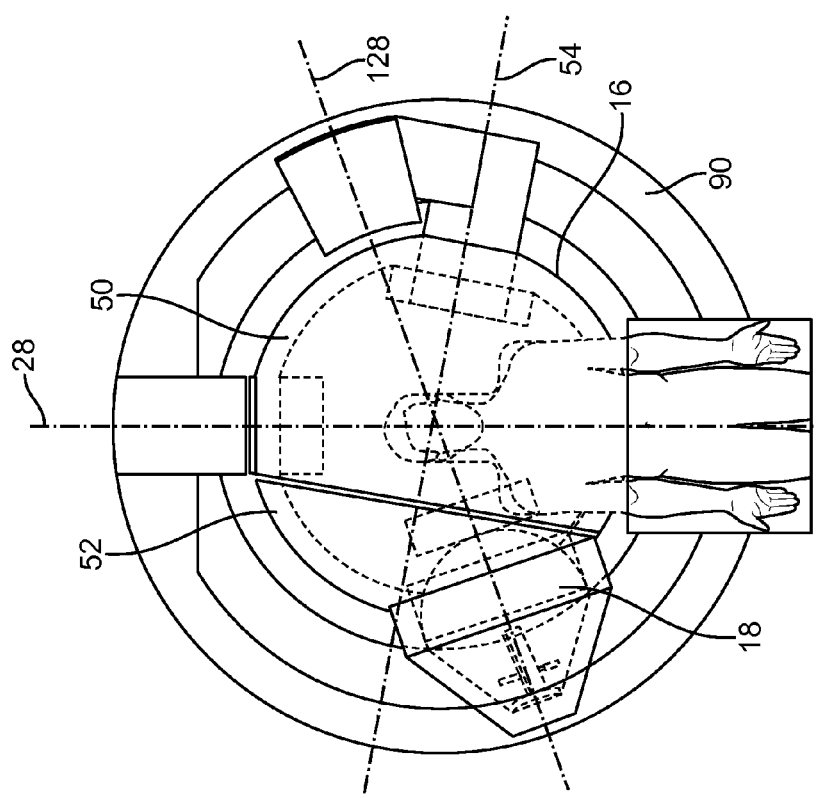
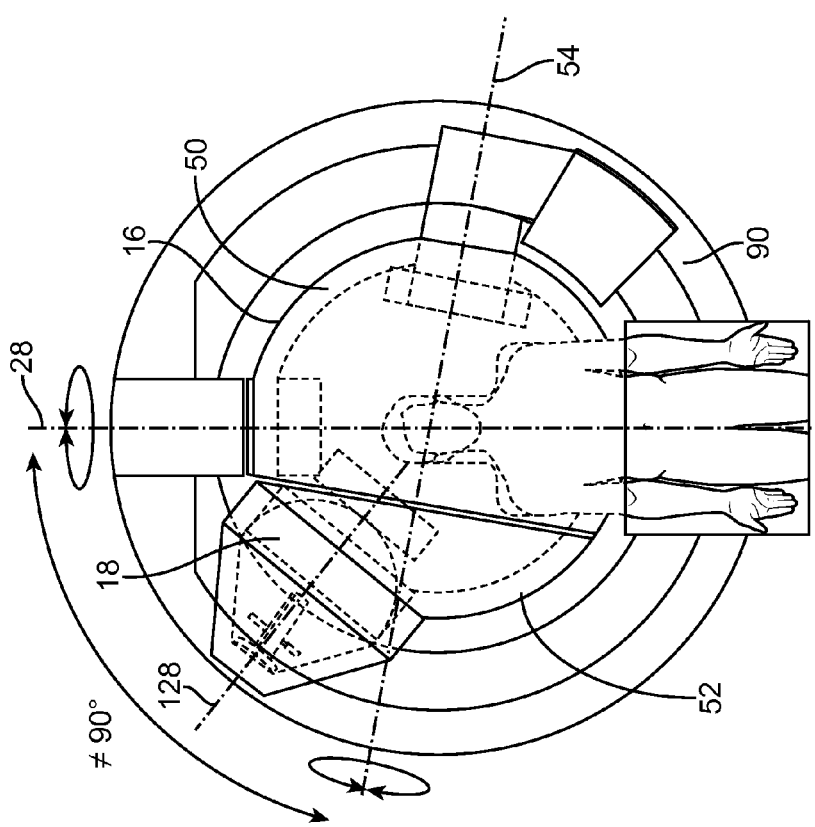
FIG. 12E
FIG. 12F

RADIATION SYSTEMS WITH MINIMAL OR NO SHIELDING REQUIREMENT ON BUILDING

RELATED APPLICATION DATA

This application claims priority to and the benefit of U.S. Provisional Patent Application No. 61/697,218, filed on Sep. 5, 2012. The entire disclosure of the above application is expressly incorporated by reference herein.

FIELD

This application relates generally to radiation systems, and more particularly, to radiation treatment systems.

BACKGROUND

Radiation has been employed for diagnostic purposes. For example, radiation may be used in an x-ray procedure or a CT procedure to obtain images of a patient. Radiation has also been employed to treat tumorous tissue. In radiation therapy, a high energy beam is applied from an external source towards the patient. The radiation source, which may be rotating (as in the case for arc therapy), produces a collimated beam of radiation that is directed into the patient to the target site. Sometimes, in radiation therapy, the high energy radiation may also be used for imaging the patient.

Existing radiation systems for imaging and/or treatment generate a significant amount of radiation during a procedure. Thus, in existing facilities that provide radiation machines, the building structures housing the radiation machines are required to be retrofitted to provide adequate radiation shielding. This ensures that radiation generated by a radiation machine does not cause harm to the operator of the radiation machine, or to other occupants of the building who are not the intended recipient of the radiation.

Applicant of the subject application determines that new radiation systems would be desirable.

SUMMARY

In accordance with some embodiments, a radiation system includes: a first support; a first structure rotatably coupled to the first support so that the first structure is rotatable about a first axis relative to the first support; a second structure rotatably coupled to the first structure so that the second structure is rotatable about a second axis that forms a non-zero angle relative to the first structure; and a first radiation source connected to the second structure; wherein the first structure and the second structure are parts of a capsule for accommodating at least a portion of a patient.

Optionally, the first structure comprises a first space, the second comprises a second space, and the first space and the second space are configured to collectively accommodate the at least a portion of the patient.

Optionally, the first structure has an interface plane that interfaces with the second structure, the interface plane forming an acute angle with respect to the first axis.

Optionally, the first radiation source is configured to rotate within a rotational plane about the second axis by rotating the second structure relative to the first structure about the second axis; and wherein an angle between the rotational plane and the first axis is adjustable by rotation of the first structure about the first axis.

Optionally, the system further includes a beam stopper connected to the second structure.

Optionally, the first radiation source is configured to deliver treatment energy.

Optionally, the system further includes: a second radiation source connected to the second structure; and an imager connected to the second structure; wherein the first radiation source is configured to deliver treatment radiation; wherein the second radiation source is configured to deliver diagnostic radiation; and wherein the first radiation source, the second radiation source, and the imager are rotatable relative to the first structure by movement of the second structure.

Optionally, the system further includes a third structure rotatably coupled to the second structure, wherein the second structure is rotatable relative to both the first and the third structures about the second axis.

Optionally, the system further includes a second support for supporting the third structure.

Optionally, the first structure and the third structure are configured to rotate simultaneously relative to the second structure, or vice versa.

Optionally, the second structure includes a shielding material that is configured to block at least 98% of radiation resulted from an operation of the first radiation source.

In accordance with other embodiments, a radiation system includes: a first support; a first structure rotatably coupled to the first support so that the first structure is rotatable about a first axis relative to the first support; a second structure rotatably coupled to the first structure so that the second structure is rotatable about a second axis; and a first radiation source connected to the second structure; wherein the first radiation source is configured to rotate within a rotational plane about the second axis by rotating the second structure relative to the first structure about the second axis; and wherein an angle between the rotational plane and the first axis is adjustable by rotation of the first structure about the first axis.

Optionally, the first structure comprises a first space, the second comprises a second space, and the first space and the second space are configured to collectively accommodate at least a portion of a patient.

Optionally, the first structure has an interface plane that interfaces with the second structure, the interface plane forming an acute angle with respect to the first axis.

Optionally, the first radiation source is configured to deliver treatment energy.

Optionally, the system further includes: a second radiation source connected to the second structure; and an imager connected to the second structure; wherein the first radiation source is configured to deliver treatment radiation; wherein the second radiation source is configured to deliver diagnostic radiation; and wherein the first radiation source, the second radiation source, and the imager are rotatable relative to the first structure by movement of the second structure.

Optionally, the system further includes a third structure rotatably coupled to the second structure, wherein the second structure is rotatable relative to both the first and the third structures about the second axis.

Optionally, the system further includes a second support for supporting the third structure.

Optionally, the first structure and the third structure are configured to rotate simultaneously relative to the second structure, or vice versa.

Optionally, the second structure includes a shielding material that is configured to block at least 98% of radiation resulted from an operation of the first radiation source.

In accordance with some embodiments, a radiation system includes a support, a capsule rotatably coupled to the support, a radiation source movably coupled to the capsule, wherein the radiation source is configured to provide a treatment radiation beam, and is capable of being turned on or off in response to a control signal, and a collimator located next to the radiation source, wherein the capsule defines a space for accommodating a portion of a patient, and includes a shielding material for attenuating radiation resulted from an operation of the radiation source, and wherein the shielding material is configured to limit a radiation exposure level to 5 mR/hr or less within 3 meters from an isocenter.

In accordance with other embodiments, a radiation system includes a patient support configured to support a patient in an upright position, wherein the patient support is rotatable about a vertical axis, a gantry defining a space for accommodating at least a portion of the patient, and a radiation source mounted on the gantry, wherein the gantry is configured to translate in a vertical direction to move the radiation source vertically.

In accordance with other embodiments, a radiation method includes delivering a radiation beam from a radiation source towards a portion of a patient, and rotating the patient relative to the radiation source, wherein the patient is rotated while the radiation beam is being delivered to the portion of the patient.

Other and further aspects and features will be evident from reading the following detailed description of the embodiments.

BRIEF DESCRIPTION OF THE DRAWINGS

The drawings illustrate the design and utility of embodiments, in which similar elements are referred to by common reference numerals. These drawings are not necessarily drawn to scale. In order to better appreciate how the above-recited and other advantages and objects are obtained, a more particular description of the embodiments will be rendered, which are illustrated in the accompanying drawings. These drawings depict only typical embodiments and are not therefore to be considered limiting of its scope.

FIG. 1A illustrates a radiation system in accordance with some embodiments;

FIG. 1B illustrates an end view of the radiation system of FIG. 1A in accordance with some embodiments;

FIG. 4 illustrates another radiation system in accordance with other embodiments;

FIGS. 12A-12G illustrate another radiation system in accordance with other embodiments;

DESCRIPTION OF THE EMBODIMENTS

Figure 2A:
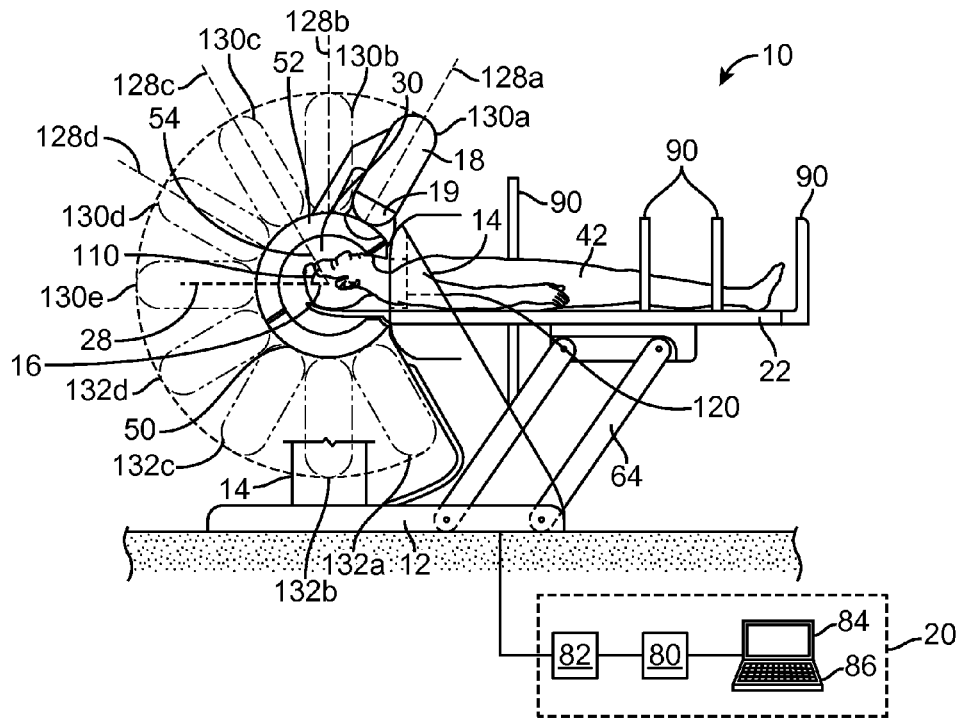
FIG. 2A illustrates another radiation system in accordance with other embodiments.

Various embodiments are described hereinafter with reference to the figures. It should be noted that the figures are not drawn to scale and that elements of similar structures or functions are represented by like reference numerals throughout the figures. It should also be noted that the figures are only intended to facilitate the description of the embodiments. They are not intended as an exhaustive description of the invention or as a limitation on the scope of the claimed invention. In addition, an illustrated embodiment needs not have all the aspects or advantages shown. An aspect or an advantage described in conjunction with a particular embodiment is not necessarily limited to that embodiment and can be practiced in any other embodiments even if not so illustrated.

FIG. 1A illustrates a radiation system 10 in accordance with some embodiments. The radiation system 10 includes a base 12, a support 14, a capsule 16, a radiation source 18, a collimator 19, a control system 20, and a patient support 22. In the illustrated embodiments, the base 12 and the support 14 are manufactured as a single piece with an unity configuration. In other embodiments, the base 12 and the support 14 may be separate components that are coupled together. Also, in further embodiments, the support 14 may be moveable relative to the base 12 in one or more degrees of freedom. In still further embodiments, the base 12 may be considered to be a part of the support 14.

In the illustrated embodiments, the capsule 16 is rotatably coupled to the support 14 about an axis 28, and defines a space 30 for accommodating at least a portion 40 of a patient 42. In some embodiments, the axis 28 may be a horizontal axis parallel to, or along, the X-axis, depending on the placement of the coordinate system. As used in this specification, the term "capsule" may refer to any structure (which may be a single component or a multiple components) that at least partially defines a space for accommodating an object, such as a portion of the patient 42, and should not be limited to structures that provide full enclosure, or structures having any particular shapes. In the illustrated embodiments, the portion 40 is a head of the patient 42. In other embodiments, the portion 40 may include other part(s) of the patient 42. For example, in other embodiments, the portion 40 may include both the head and the shoulders of the patient 42. In further embodiments, the portion 40 may include a body of the patient 42.

As shown in the figure, the capsule 16 includes a first capsule portion 50 and a second capsule portion 52 that is rotatable relative to the first capsule portion 50 about an axis 54. In some embodiments, the axis 54 may be a vertical axis that is parallel to, or along, the Z-axis, depending on the placement of the coordinate system. In one implementation, the first capsule portion 50 and the second capsule portion 52 may be rotatably coupled to each other using a tongue-and-groove mechanism, which may be more effective in preventing leakage of radiation between the coupling of the portions 50, 52 (because part of the tongue-and-groove mechanism may attenuate some of the radiation). In other embodiments, the first and second capsule portions 50, 52 may be coupled using other mechanisms, such as abutting surfaces on respective portions 50, 52, overlapping surfaces on respective portions 50, 52, etc. In the illustrated embodiments, the first and second capsule portions 50, 52 define an interior surface that has a partial spherical configuration. In other embodiments, the interior surface may have other configurations, and is not limited to a spherical configuration. Also, in the illustrated embodiments, the capsule 16 is a hollow structure (e.g., a hollow sphere) separated at a plane that is parallel to axis 28 to form first and second portions 50, 52. In other embodiments, the capsule 16 may be separated at a plane that forms an angle relative to the axis 28 to form first and second portions 50, 52.

In the illustrated embodiments, the capsule 16 includes a shielding material that is configured to block at least some of the radiation that results from an operation of the radiation source 18. The shielding material may include any material(s) that is known for providing radiation shielding, including but not limited to steel, lead, tungsten, or combination thereof. In some embodiments, the shielding material may be used to make the wall of the capsule 16. In other embodiments, the shielding material may be coupled to the wall of the capsule 16. For example, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such a feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such a feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement.

In the illustrated embodiments of FIG. 1A, the radiation source 18 is a treatment radiation source that is configured to provide a treatment radiation beam towards an isocenter that coincides with a target region in the portion 40 of the patient 42. The radiation source 18 may be capable of being turned on or off in response to a control signal (e.g., a signal from a control unit, etc.). Alternatively it may be a radioactive source which is not capable of being turned off, but may be shuttered. The radiation source 18 may be configured to generate a cone beam, a fan beam, or other types of radiation beams in different embodiments. The radiation source 18 may be implemented using an x-band linear accelerator. In other embodiments, the radiation source 18 may be implemented using other types of linear accelerator. It should be noted that as used in this specification, the term "radiation source" or similar terms, such as "source", refers to a component from which a radiation or energy is emitted, and may or may not include an accelerator. Also, in the illustrated embodiments, the radiation source 18 is configured to provide the treatment radiation beam having an energy level that is anywhere from 0.2 MV to 8 MV, and more preferably, anywhere from 0.9 MV to 3 MV. In other embodiments, the radiation source 18 may be configured to provide the treatment radiation beam having other energy levels, such as lower than 0.2 MV or higher than 8 MV. However, providing a radiation beam having an energy level that is at or below 3 MV is more desirable because it may obviate the need to add shielding to the building of the facility, or at least reduce some of the shielding requirement for the building. In other embodiments, shielding to a building may also not be required even for radiation beams having an energy level that is higher than 3 MV. Such may be accomplished by configuring the shielding of the system 10 (e.g., providing thicker shielding, and/or using more dense material(s), etc.).

Also, in other embodiments, a small beam tube may be employed in conjunction with closely packed shielding to further reduce radiation exposure. To obtain close proximity to the beam, and further reduce the solid-angle to the target, the shielding may be built into the accelerator structure, employing for example dense conductive materials such as Elkonite. With the aid of electromagnets or permanent magnets, a serpentine beam tube may be employed to block line of sight to the target, and to aid shielding of radiation exposure. An example would involve use of a bending magnet, preferably achromatic bending magnet.

In the illustrated embodiments, the source to isocenter distance (SID) or source-axis distance (SAD) is less than 800 mm, and more preferably less than 600 mm, and even more preferably around 415 mm (415 mm±40 mm). Also, in some embodiments, the SID/SAD value for the radiation system 10 is less than those in existing radiation machines. Such configuration allows the radiation source 18 to provide less radiation energy compared to existing treatment radiation sources, and still sufficiently treats a target (e.g., tumor, or a nerve). Also, because of the reduction in energy requirement, the amount of shielding that is needed for a facility building is substantially reduced, or may be eliminated. Furthermore, because of the reduction in energy requirement, the size of the accelerator for generating the radiation may be reduced. This in turn reduces the weight of the system 10, thereby obviating any need to retrofit a building, or at least reducing an amount of retrofit required, for supporting a weight of the system 10. In other embodiments, the SID/SAD may have other values.

As shown in FIG. 1B, which is an end view of the system 10 of FIG. 1A, the radiation source 18 is tilted so its axis 128 (which may be a beam axis in some embodiments) forms an angle 79 (e.g., a non-zero acute angle) relative to the axis 54. Such a configuration allows the radiation source 18 to deliver radiation from different angles towards the portion 40 of the patient 42 as the second portion 52 rotates relative to the first portion 50 about the axis 54. In other embodiments, the capsule 16 may be rotated about the axis 28 to turn the radiation source 18 around the patient so that radiation may be delivered to the patient from different angles. In some embodiments, the rotation of the second portion 52 about the axis 54, and the rotation of the capsule 16 about the axis 28, may be performed one after the other. Alternatively, the rotation of the second portion 52 about the axis 54, and the rotation of the capsule 16 about the axis 28, may be performed simultaneously. In some embodiments, the radiation source 18 may be configured to be tiltable relative to the second portion 52.

Returning to FIG. 1A, the collimator 19 is located next to the radiation source 18, and is configured to shape the radiation beam from the source 18 in accordance with a treatment plan. In some embodiments, the collimator 19 may be considered to be a part of the radiation source 18. As shown in the figure, none of the components from the radiation source 18 or the collimator 19 extends into the space 30. This creates the interior surface of the capsule 16 that maintains a clearance to the portion 40 of the patient 42 inside the space 30, thereby avoiding the risk of having a component that collides with the portion 40 of the patient 42 that is inside the space 30 as the capsule 16 rotates about the axis 28, and/or as the second capsule portion 52 rotates about the axis 54. In other embodiments, instead of a collimator, component 19 may be a cone with an outlet having a pre-defined configuration, an iris that provides an outlet having a cross-section that is adjustable, or any of other devices that is capable of blocking at least some of the radiation provided from the radiation source 18. In one or more embodiments, the component 19 may be configured to block/attenuate at least 98% of the radiation (e.g., within the treatment field), and more preferably at least 99.9% of the radiation (e.g., outside of the treatment field).

As shown in FIG. 1A, the capsule 16 also includes an opening 60 for allowing the portion 40 of the patient 42 to partially enter interior space 30 of the capsule 16. The patient support 22 includes a table 62 for supporting the patient 42, and a positioner 64 configured to translate the table 62 axially (e.g., along the X-axis) so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

In the illustrated embodiments, the control system 20 includes a processor 80, such as a computer processor, coupled to a control 82. The control system 20 may also include a monitor 84 for displaying data and an input device 86, such as a keyboard or a mouse, for inputting data. In the illustrated embodiments, during an imaging and/or treatment procedure, the capsule 16 rotates about the patient 42 (as in a CT procedure and/or an arch-therapy). The operation of the radiation source 18 and the capsule 16 are controlled by the control 82, which provides power and timing signals to the radiation source 18 and the collimator system 19, and controls a rotational speed and position of the capsule 16, and/or a rotational speed and position of the second portion 52 relative to the first portion 50, based on signals received from the processor 80. Although the control 20 is shown as a separate component from the capsule 16 and the processor 80, in alternative embodiments, the control 20 may be a part of the capsule 16 or the processor 80.

In some embodiments, movement of the components of the system 10 (e.g., the capsule 16, the second portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

As shown in FIG. 1A, the radiation system 10 may optionally further include one or more shields 90 for blocking radiation that results from an operation of the radiation source 18. The shield(s) 90 may be coupled to the patient support 22, the support 14, the capsule 16, the radiation source 18, any of other components in the system 10, or any combination thereof. The additional shield(s) 90 is advantageous because it allows the capsule 16 to block less radiation. For example, in some embodiments, the shielding material at the capsule 16 may be configured to block radiation so that it attenuates at least 98%, and more preferably at least 99.9%, and even more preferably at least 99.999%, of the radiation (e.g., photons/charged particles, such as electrons, neutrons, etc.), resulted from an operation of the radiation source 18 traveling therethrough. In some embodiments, the shielding material at the capsule 16, and the additional shield(s) 90, may be configured to block off a sufficient amount of radiation resulted from an operation of the radiation source 18 so that they obviate the need to provide shielding at a facility building, such as at a hospital. In other embodiments, instead of completely eliminating shielding at a building, the shielding material at the capsule 16, and the additional shield(s) 90, may be configured to block off a sufficient amount of radiation resulted from an operation of the radiation source 18, so that they reduce a significant amount (e.g., at least 50%, and more preferably, at least 90%) of the shielding requirement at a building. In other embodiments, the shield(s) 90 may be configured to block off all or most of the radiation resulted from an operation of the radiation source 18. In such cases, the capsule 16 may not include any shielding material.

It should be noted that the shield(s) 90 is not limited to the configuration shown in the illustrated embodiments, and that in other embodiments, the shield(s) 90 may have different configurations (e.g., shapes). For example, in other embodiments, the shield 90 may be in a form of a tube or container that houses a part (e.g., the body, legs, or both, etc.) of the patient 42.

Also, as shown in FIG. 1A, the radiation system 10 may optionally further include an imager 100 in accordance with some embodiments. The imager (imaging panel) 100 may be based on amorphous silicon or any of other technologies known in the art. The imager 100 is located at an operative position relative to the radiation source 18 (e.g., on the side of the capsule 16 that is opposite from the radiation source 18). During use, radiation from the radiation source 18 enters the patient 42 and exits the patient 42 to reach the imager 100. The imager 100 generates image data in response to the radiation received thereon. The radiation may be treatment radiation in some embodiments, or may be diagnostic radiation in other embodiments. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

Also, in one or more embodiments described herein, the radiation system 10 may optionally further include one or more imaging sources (e.g., two x-ray sources in keV range) and one or more corresponding imagers that are in corresponding operative positions relative to the imaging source(s). The imager(s) may be coupled to the base 12, to the capsule 16, to the support 22, or to any component of the radiation system 10. In other embodiments, the imager(s) may be coupled to another structure that is not a part of the radiation system 10. For example, in other embodiments, the imager(s) may be mounted to a room (e.g., to a ceiling, a floor), or to a support that is movable independent of the base 12. During use, radiation from the imaging source(s) enters the patient 42 and exits the patient 42 to reach the corresponding imager(s). The imager(s) generates image data in response to the radiation received thereon. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

It should be noted that the radiation system 10 is not limited to the examples described previously, and that the radiation system 10 may have different configurations in different embodiments.

For example, in other embodiments, instead of being a treatment source, the radiation source 18 may be a diagnostic radiation source for providing diagnostic energy. In such cases, the imager 100 is configured to receive diagnostic radiation (e.g., radiation generated at keV energy level) and generate image signals in response thereto. In other embodiments, in addition to being a treatment radiation source, the radiation source 18 may also be a diagnostic radiation source for providing diagnostic energy. In such cases, the imager 100 is configured to selectively receive diagnostic radiation or treatment radiation and generate image signals in response thereto.

In some embodiments, treatment energy is an energy having a value that is higher than 160 kilo-electron-volts (keV), and more preferably, higher than 0.9 mega-electron-volts (MeV) (e.g., 8 MeV or lower). Also, in some embodiments, diagnostic energy is generally those energies below the high energy range, and more typically below 160 keV. In other embodiments, the treatment energy and the diagnostic energy can have other energy levels, and refer to energies that are used for treatment and diagnostic purposes, respectively. In some embodiments, the radiation source 18 is able to generate X-ray radiation at a plurality of photon energy levels within a range anywhere from 10 keV to 20 MeV, and more preferably, from 10 keV to 3 MeV. Radiation sources capable of generating X-ray radiation at different energy levels are described in U.S. patent application Ser. No. 10/033,327, entitled "RADIOTHERAPY APPARATUS EQUIPPED WITH AN ARTICULABLE GANTRY FOR POSITIONING AN IMAGING UNIT," filed on Nov. 2, 2001, and U.S. patent application Ser. No. 10/687,573, entitled "MULTI-ENERGY X-RAY SOURCE," filed on Oct. 15, 2003.

In further embodiments, the structure 16 supporting the radiation source 18 may have different configurations as those described. For example, in other embodiments, the structure 16 may have a ring configuration, as in a ring gantry. In further embodiments, the structure 16 may include an arm for carrying the radiation source 18. The arm may have an L-shape, a C-shape, or any other shapes in different embodiments. If a C-shape arm (C-arm) is used, one end of the arm may carry the radiation source 18, the other end of the arm may carry the imager 100, and the middle segment of the C-arm may be rotatably coupled to a support structure.

In the above embodiments, the axis 54 of rotation for the second portion 52, and the axis 28 of rotation for the first portion 50 form an angle 110 that is approximately 90° (i.e., 90°±10°). In other embodiments, the angle 110 between the axes 28, 54 may be different to provide different angular coverage by the system 10. In the above embodiments, the axis 54 of rotation for the second portion and the axis 128 of the radiation source 18 form an angle 79 that is anywhere from 0° to 90°, and more preferably, anywhere from 10° to 80° (such as, anywhere from 30° to 60°). In other embodiments, the angle 79 between the axes 54, 128 may be different to provide different angular coverage by the system 10.

FIG. 2A illustrates another radiation system 10 in accordance with other embodiments. The system 10 of FIG. 2A is similar to that of FIG. 1, except that the support 14 is located on the left and right sides of the patient support 22. In particular, the support 14 has a first portion that is next to a left side of the patient support 22, and a second portion that is next to a right side of the patient support 22. The first and second portions of the support 14 are coupled together by a support component 120 that extends between the first and second portions of the support 14. The support component 120 has an opening for allowing a portion of the patient to be inserted therethrough to reach the space 30. The first portion 50 of the capsule 16 is rotatably coupled to the support component 120 so that the first portion 50 may rotate about the axis 28. The second portion 52 of the capsule 16 is rotatably coupled to the first portion 50 so that the second portion 52 may rotate about the axis 54.

During use, the second portion 52 may be selectively rotated about the axis 54 relative to the first portion 50, to place the radiation source 18 at a position that lies in a plane 128a (e.g., a position 130a). The radiation source 18 may then be rotated around the patient by rotating the first portion 50 about the axis 28 relative to the support component 120, thereby placing the radiation source 18 at different positions around the patient in plane 128a (such as positions 130a, 132a). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128b (e.g., position 130b). The radiation source 18 may then be rotated around the patient by rotating the first portion 50 about the axis 28 relative to the support component 120, thereby placing the radiation source 18 at different positions around the patient in plane 128b (such as positions 130b, 132b). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128c (e.g., position 130c). The radiation source 18 may then be rotated around the patient by rotating the first portion 50 about the axis 28 relative to the support component 120, thereby placing the radiation source 18 at different positions around the patient in plane 128c (such as positions 130c, 132c). As the first portion 50 is rotated about the axis 28, treatment radiation or imaging radiation may be delivered to the patient.

In still another example, the second portion 52 may be selectively rotated about the axis 54 relative to the first portion 50, to place the radiation source 18 at a position that lies in plane 128d (e.g., position 130d). The radiation source 18 may then be rotated around the patient by rotating the first portion 50 about the axis 28 relative to the support component 120, thereby placing the radiation source 18 at different positions around the patient in plane 128d (such as positions 130d, 132d). As the first portion 50 is rotated about the axis 28, treatment radiation or imaging radiation may be delivered to the patient.

In further embodiments, during use, the radiation source 18 may be placed at a position 130e by rotating the second portion 52 about the axis 54 relative to the first portion 50. This allows the radiation source 18 to deliver radiation from the top of the patient's head (superior to inferior).

Although several possible positions for the radiation source 18 are shown as examples, it should be understood that the radiation source 18 may be placed at other positions, such as positions that are anywhere between the examples described previously.

Also, in further embodiments, instead of, or in addition to, delivering treatment or imaging radiation to the patient while the first portion 50 rotates about the axis 28, treatment or imaging radiation may be delivered to the patient while the second portion 52 rotates about the axis 54.

Figure 2B:
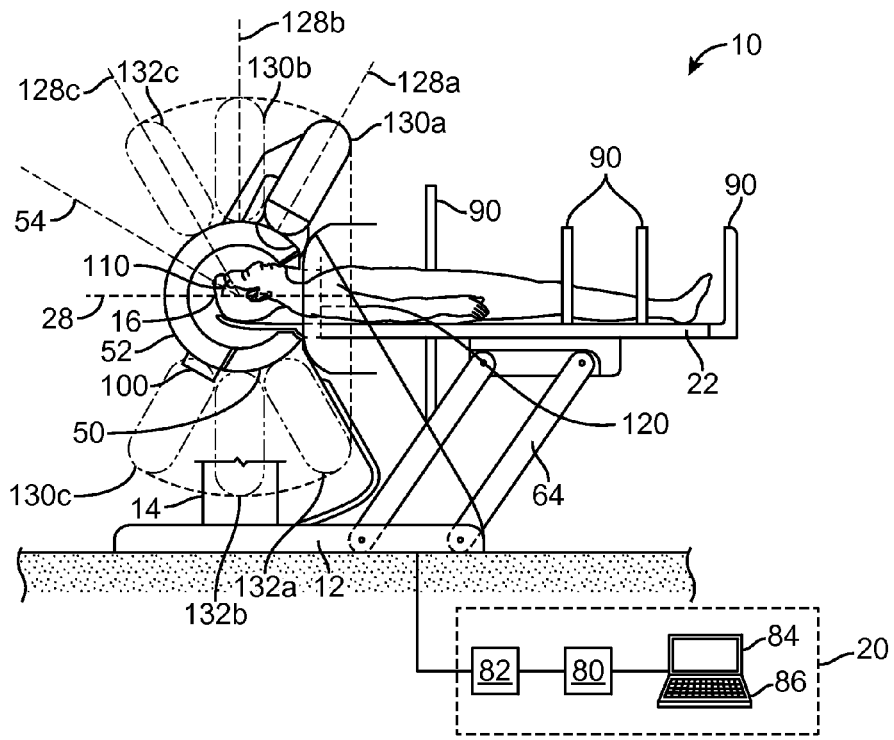
FIG. 2B illustrates another radiation system in accordance with other embodiments.

In other embodiments, the angular coverage provided by the radiation system 10 may be different from that shown in FIG. 2A by changing the relative angle 110 between the axis 28 of rotation and the axis 54 of rotation. FIG. 2B illustrates another radiation system 10 in accordance with other embodiments. The system 10 of FIG. 2B is similar to that of FIG. 2A, except that the angle 110 between the axes 28, 54 of rotation is decreased compared to that shown in FIG. 2A. Also, in the illustrated embodiments, the beam axis 128 of the radiation source 18 is approximately parallel (forms a 0°±10°) to the plane of interface between the first portion 50 and the second portion 52. As a result, the possible positions achievable by the radiation source 18 is different from that shown in FIG. 2A.

In the embodiments of FIG. 2B, during use, the second portion 52 may be selectively rotated about the axis 54 relative to the first portion 50, to place the radiation source 18 at position 130a. The radiation source 18 may then be rotated around the patient by rotating the first portion 50 about the axis 28 relative to the support component 120, thereby placing the radiation source 18 at different positions around the patient (such as position 132a). As the first portion 50 is rotated about the axis 28, treatment radiation or imaging radiation may be delivered to the patient.

In another example, the second portion 52 may be selectively rotated about the axis 54 relative to the first portion 50, to place the radiation source 18 at a position that lies in plane 128b. The radiation source 18 may then be rotated around the patient by rotating the first portion 50 about the axis 28 relative to the support component 120, thereby placing the radiation source 18 at different positions around the patient (such as positions 130b, 132b). As the first portion 50 is rotated about the axis 28, treatment radiation or imaging radiation may be delivered to the patient.

In still another example, the second portion 52 may be selectively rotated about the axis 54 relative to the first portion 50, to place the radiation source 18 at position 130c. The radiation source 18 may then be rotated around the patient by rotating the first portion 50 about the axis 28 relative to the support component 120, thereby placing the radiation source 18 at different positions around the patient (such as position 132c). As the first portion 50 is rotated about the axis 28, treatment radiation or imaging radiation may be delivered to the patient.

Although several possible positions for the radiation source 18 are shown as examples, it should be understood that the radiation source 18 may be placed at other positions, such as positions that are anywhere between the examples described previously.

Also, in further embodiments, instead of, or in addition to, delivering treatment or imaging radiation to the patient while the first portion 50 rotates about the axis 28, treatment or imaging radiation may be delivered to the patient while the second portion 52 rotates about the axis 54. For example, in other embodiments, the second portion 52 may rotate relative to the first portion 50 within the plane 128a to place the radiation source 18 at different positions around the patient (such as positions 130a, 130c), while the radiation source 18 delivers treatment or imaging radiation towards the patient.

In another example, the first portion 50 may first rotate relative to the support component 120 by 180° relative to that shown in FIG. 2B. Then the second portion 52 may rotate relative to the first portion 50 within the plane 128c to place the radiation source 18 at different positions around the patient (such as positions 132a, 132c), while the radiation source 18 delivers treatment or imaging radiation towards the patient. In other examples, the first portion 50 may be rotated relative to the support component 120 by other angles (different from) 180° relative to that shown in FIG. 2B.

In the embodiments of FIG. 2B, the capsule 16 is supported by the support structure 14 (partially shown) on one side of the capsule 16. However, in other embodiments, the system 10 may further include an additional support on the opposite side of the capsule 16.

Figure 3A:
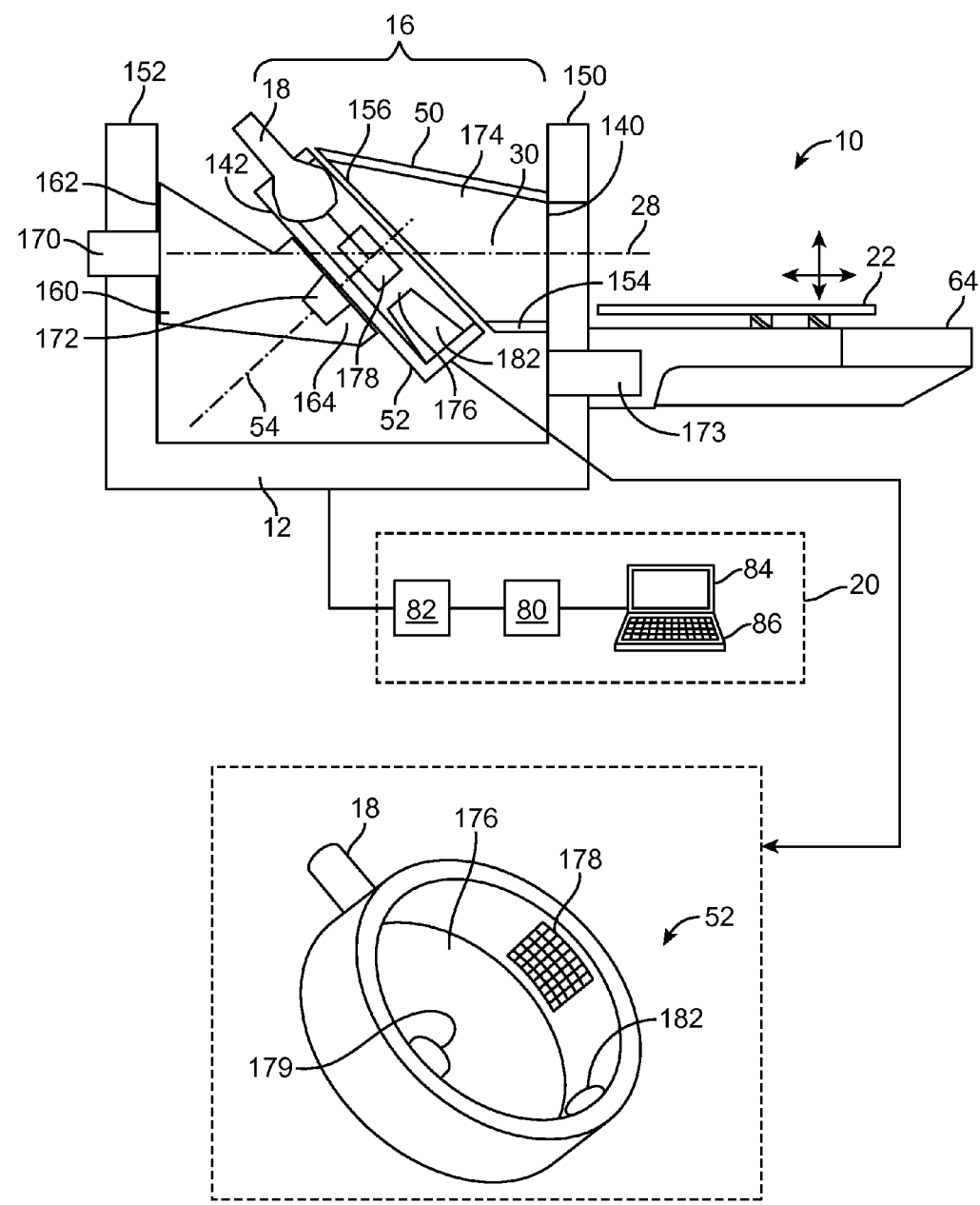
FIGS. 3A-3K illustrate another radiation system in accordance with other embodiments.

FIG. 3A illustrates a variation of the system 10 of FIG. 2B in accordance with some embodiments. The degree of movement for the radiation source 18 in the system 10 of FIG. 3A is similar to that of FIG. 2B, except that the capsule 16 has a different shape, and the capsule 16 is rotatably supported at a first end 140, and a second end 142 of the capsule 16. In the illustrated embodiments, the base 12 is coupled to (e.g., integrally formed with) a first support 150 and a second support 152. The system 10 also includes a support member 160 disposed between the support 152 and the second portion 52 of the capsule 16. The support member 160 has an end 162 that is rotatably coupled to the support 152, and another end 164 that is rotatably coupled to the second portion 52 of the capsule 16. Thus, the second portion 52 is rotatably coupled between the first portion 50 and the support member 160, and the first portion 50 and the support member 160 are in turn, rotatably coupled to the supports 150, 152, respectively. The rotatable coupling between the various components may be implemented using bearings in some embodiments, such as large ring bearings. As shown in the figure, the system 10 also includes a first motor 170 for turning the support member 160 about the axis 28 relative to the support 152, and a second motor 172 for turning the second portion 52 about the axis 54 relative to the support member 160 and relative to the first portion 50. The system 10 also includes a third motor 173 for turning the first portion 50 relative to the support 150. During use, the motors 170, 172, 173 rotate in synchronization with each other, so that the oblique plane at the end 164 and the oblique plane at the end 156 are maintained parallel relative to each other in order to accommodate the portion 52 between the support member 160 and the portion 50.

In the illustrated embodiments, the first portion 50 defines a space 174, and the second portion 52 defines a space 176, wherein the space 174 and the space 176 together form the space 30 for accommodating a portion of a patient. The support table 22 may be positioned by positioner 64 during use, which may be configured to translate the table 22 longitudinally and/or vertically. In other embodiments, the positioner 64 may also be configured to shift the table 22 laterally left and right, and/or to rotate the table 22 in one or more degrees of freedom.

As shown in the figure, the second portion 52 also includes an imager 178 on one side of the second portion 52, and an imaging source 179 located on the opposite side of the second portion 52. Also, the second portion 52 includes the radiation source 18 attached thereto, and a beam stop 182 on the opposite side. The beam stop 182 provides shielding of the primary beam and may be made from tungsten or lead in some embodiments. The portion of the beam stop 182 facing the patient is preferably concave to better shield scattered ionizing radiation. It should be noted that the beam stop 182 may be included in other embodiments described herein, even if the figures do not explicitly show it. The imaging source 179 may be a x-ray source (e.g., in keV range), a MRI component, an ultrasound source, or any component that is capable of generating energy for imaging purposes. Although the radiation source 18, the imaging source 179, and the beam stop 182 are illustrated as protruding into the space 176, in other embodiments, these components may not protrude into the space 176. During use, the imaging source 179 and the imager 178 may be used to obtain image(s) of a portion of the patient that is disposed therebetween. Such may be performed before a treatment session begins (e.g., to register the position of the patient/target region). Alternatively, the imaging may be performed during treatment session (e.g., to track and/or to verify a position of a target region).

In some embodiments, the first portion 50 may be an oblique hollow cone having an outer open end 140 normal to axis 28 and an inner open end 156 angled relative to axis 28 and normal to axis 54. Outer open end 140 is rotatably connected to the support 150 to allow first portion 50 to rotate about axis 28. Inner open end 156 faces second portion 52. Second portion 52 is a cylinder with an open end and a closed end. The open end faces inner open end 156 of first portion 50. The closed end is rotatably connected to a support arm 160 to allow second portion 52 to rotate about the axis 54. Support arm 160 has an inner end 164 normal to axis 54 and an outer end 162 normal to axis 28 and inner end 164 is rotatably connected to second portion 52. Outer end 162 is connected to the motor 170 in the second support 152."

Figure 3B:
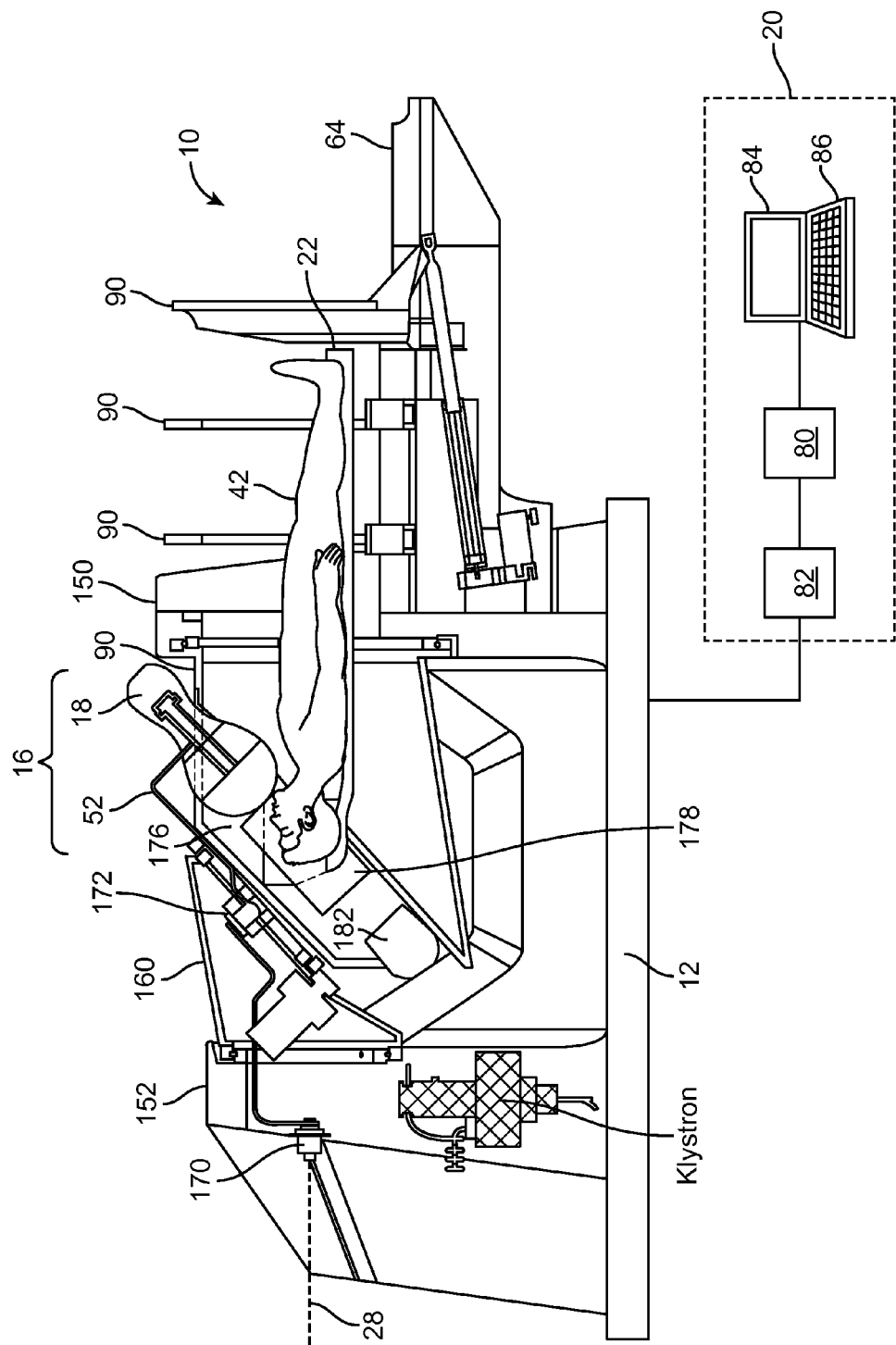

FIG. 3B illustrates an implementation of the system 10 of FIG. 3A in accordance with some embodiments, particularly showing the system 10 being used with a patient 42. During use, the patient 42 is supported on the table 22, and the positioner 64 moves the table 22 along its longitudinal axis to slide a portion of the patient 22 through an opening at the support 150, and through the space 174 of the first portion 50, so that a target area (brain tissue in the example shown) is located in the space 176 within the second portion 52. As shown in the figure, the second portion 52 may have an imager 178 on one side of the space 176, and an imaging source 179 (shown in FIG. 3A) on the opposite side of the space 176, so that a part of the patient may be imaged by the imaging source 179 and the imager 178.

As shown in the figure, the system 10 may include additional shields 90. The shields 90 and the capsule 16 may cooperate to block off at least 98%, and more preferably at least 99.9%, and even more preferably at least 99.999%, of the radiation resulted from an operation of the radiation source 18. In other embodiments, the shields 90 themselves may block off most of the radiation resulted from an operation of the radiation source 18. In some embodiments, the shields 90 may be moveable relative to the patient support 22. For example, in some embodiments, each shield 90 may have a left portion and a right portion that are housed underneath the support 22 (e.g., on opposite sides of the positioner 64). After the patient is placed on the support 22, the left and right portions of the shields 90 from the left and right sides of the positioner 64, respectively, may then be moved up to a closed position, thereby surrounding parts of the patient.

It should be noted that any of the features related to shielding discussed with reference to the embodiments of FIG. 1 may be included in the embodiments of FIGS. 3A, 3B. For example, in some embodiments, the capsule 16 includes a shielding material that is configured to block at least some of the radiation that is resulted from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such a feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such a feature is advantageous because it allows the radiation system 10 to be useable at any location within the building, or at any facility, with minimal retrofit to be done to the building to provide radiation shielding.

In some embodiments, movement of the components of the system 10 of FIGS. 3A, 3B (e.g., the support member 160, the first portion 50, the second portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 3C:
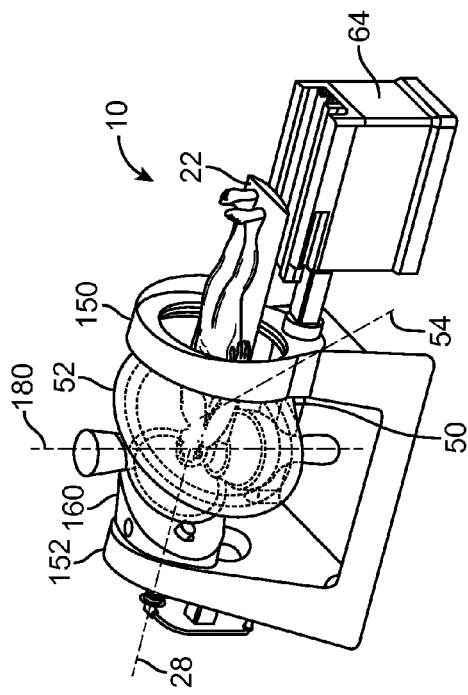

FIGS. 3C-3H illustrates some movement configurations that may be accomplished using the system 10 of FIG. 3B. As shown in FIG. 3C, the second portion 52 may be rotated relative to the first portion 50 and the support member 160 (on opposite sides of the second portion 52) until the axis 180 (e.g., beam axis) of the radiation source 18 is approximately perpendicular (e.g., 90°±10°) to the axis 28 of rotation to reach the configuration shown in the figure. Then the support member 160, and the first and second portions 50, 52 of the capsule 16 may be rotated together about the axis 28 to turn the radiation source 18 about the patient. For example, after the components 50, 52, 160 have been rotated by 90°, the system 10 will have a configuration shown in FIG. 3D. In the example shown, the path of the radiation source 18 lies in a plane that is approximately perpendicular to the axis 28.

Alternatively, from the position shown in FIG. 3C, the second portion 52 carrying the radiation source 18 may be rotated about the axis 54 to turn the second portion 52 relative to the components 160, 50. For example, after the second portion 52 has been rotated by 90° about the axis 54, the system 10 will have a configuration shown in FIG. 3E. In the example shown, the path of the radiation source 18 relative to the support member 152 lies in a plane that forms a non-perpendicular angle relative to the axis 28.

Figure 3D:
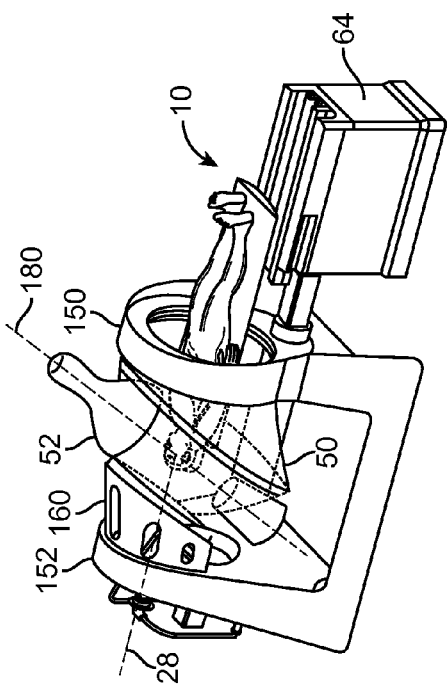
Figure 3E:
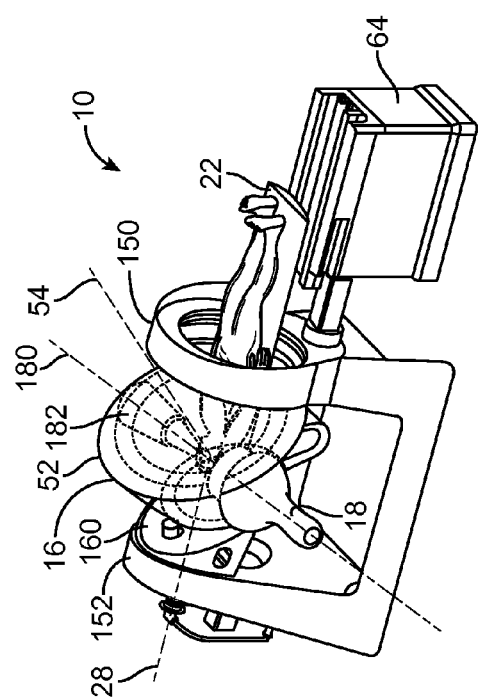
Figure 3F:
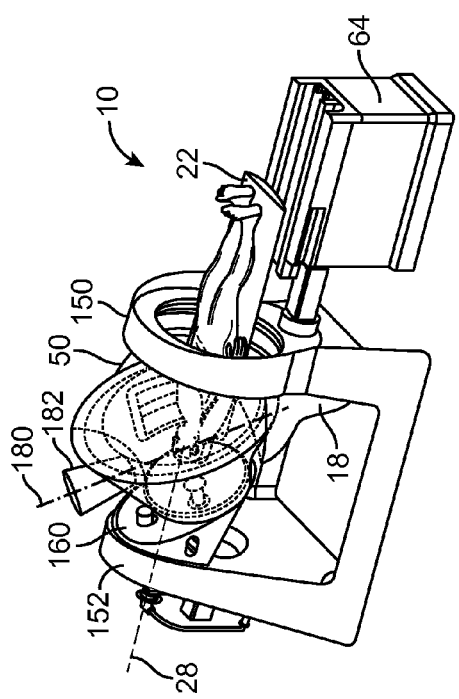

Also, in another example, from the position shown in FIG. 3E, the support member 160, and the first and second portions 50, 52, may be rotated together about the axis 28 by 180° to achieve the configuration shown in FIG. 3F.

Figure 3H:
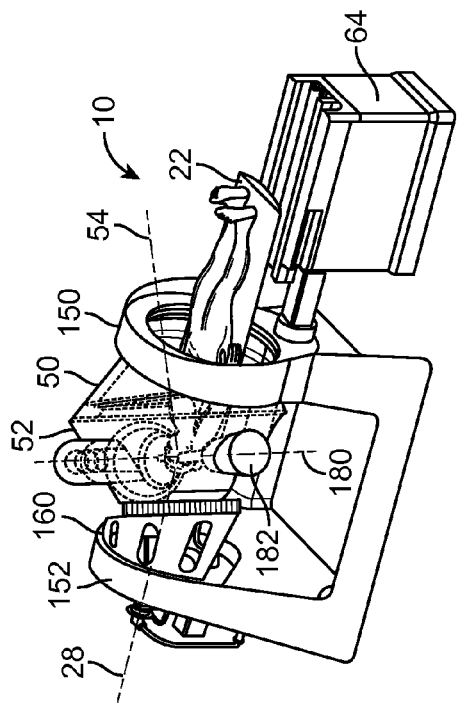
Figure 3G:
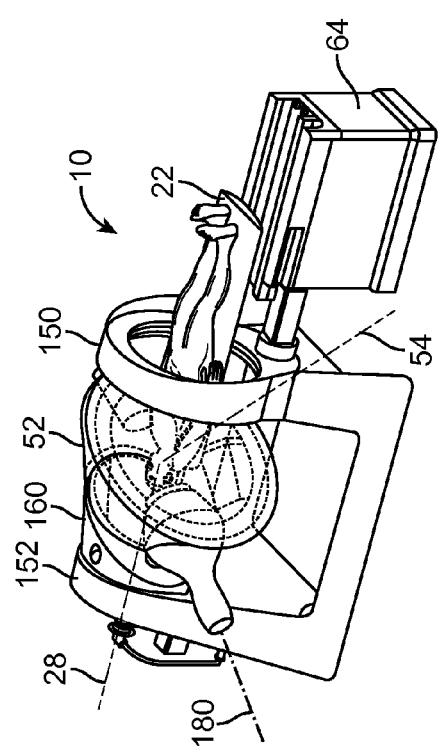

It should be noted that at any given configuration formed by the components 50, 52, 160, the second portion 52 may be rotated about the axis 54 relative to the two adjacent components 50, 160 to turn the radiation source 18 around the patient so that energy can be delivered towards the patient from various angular positions. For example, from the configuration shown in FIG. 3D, the second portion 52 may be rotated about the axis 54 relative to the components 50, 160 to turn the radiation source 18 around the patient. In such cases, the rotational path of the radiation source 18 lies in a plane that forms a non-perpendicular angle relative to the axis 28. FIG. 3G shows the configuration of the system 10 when the component 52 of FIG. 3D is rotated 90° about the axis 54.

Also, at any given configuration formed by the components 50, 52, 160, all three components 50, 52, 160 may be rotated about the axis 28 relative to the supports 150, 152 to turn the radiation source 18 around the patient so that energy can be delivered towards the patient from various angular positions. For example, from the configuration shown in FIG. 3D, the components 50, 52, 160 may be rotated about the axis 28 together to turn the radiation source 18 around the patient. In such cases, the rotational path of the radiation source 18 lies in a plane that is perpendicular to the axis 28. FIG. 3C shows the configuration of the system 10 when the components 50, 52, 160 of FIG. 3D are rotated 90° about the axis 28.

It should be noted that the possible configurations that may be achieved by the system 10 are not limited to the examples described, and that the system 10 may accomplish other configurations in other embodiments. For example, FIG. 3H shows another configuration that may be achieved by turning the support member 160, and/or the second portion 52.

In one or more embodiments, the rotation of the components 50, 52, 160 about the axis 28 may be accomplished by activating the motor 170 (FIG. 3B). While the components 50, 52, 160 are being rotated about the axis 28, the second portion 52 may remain fixed in position relative to the two adjacent components 50, 160. Such may be accomplished using a locking mechanism that locks the second portion 52 in place relative to the first portion 50 and the support member 160. Alternatively, while the components 50, 52, 160 are being rotated about the axis 28, the second motor 172 (FIG. 3B) may also be activated to turn the second portion 52 relative to the two adjacent components 50, 160. Activating the motors 170, 172 simultaneously is advantageous because it allows the system 10 to form a desired configuration within a shorter amount of time (compared to when the motors 170, 172 are sequentially activated), thereby reducing treatment time for the patient.

Figure 3I:
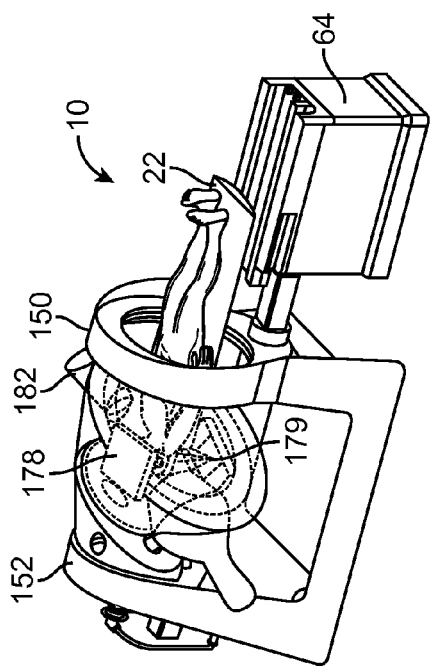

As discussed, the system 10 may include an imager 178 and a corresponding imaging source 179 (FIG. 3I). FIG. 3I illustrates the system 10, particularly showing the imager 178 and the imaging source 179 in relation with the rest of the components of the system 10. Although one set of imager 178 and imaging source 179 is shown in the example, in other embodiments, the system 10 may have two sets of imagers 178 and imaging sources 179 that are placed at 90° (or at any of other angles) relative to each other.

As discussed, the system 10 may optionally include one or more shields 90. FIG. 3J illustrates the system 10 of FIG.

3B, particularly showing the system 10 having a shield 90. The shield 90 has a right portion 190 and a left portion 192. During use, the right and left portions 190, 192 of the shield 90 may be retracted below the patient support 22 and/or next to the positioner 64. After the patient has been placed on the patient support 22, the right and left portions 190, 192 of the shield 90 may be moved mechanically upward to a closed position, thereby creating an enclosure that completely surrounds the patient.

Figure 3K:
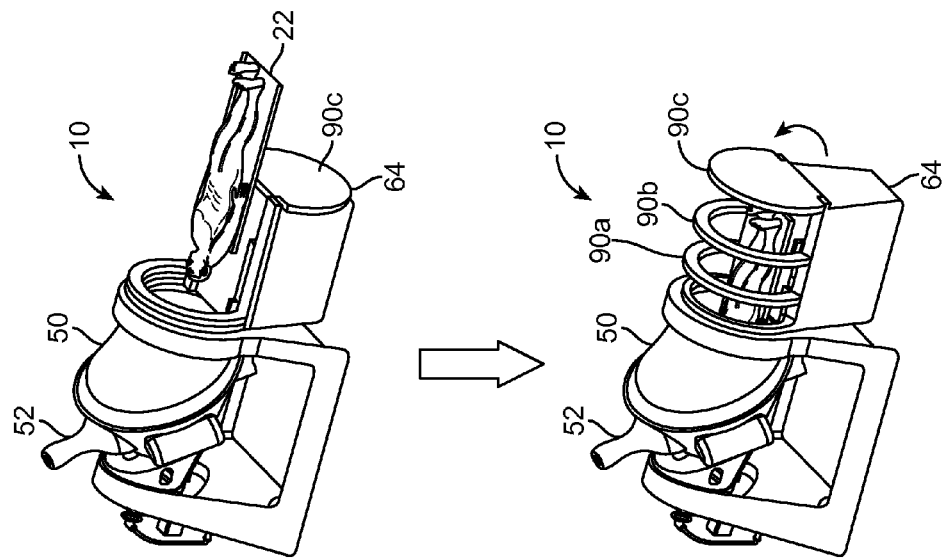
Figure 3J:
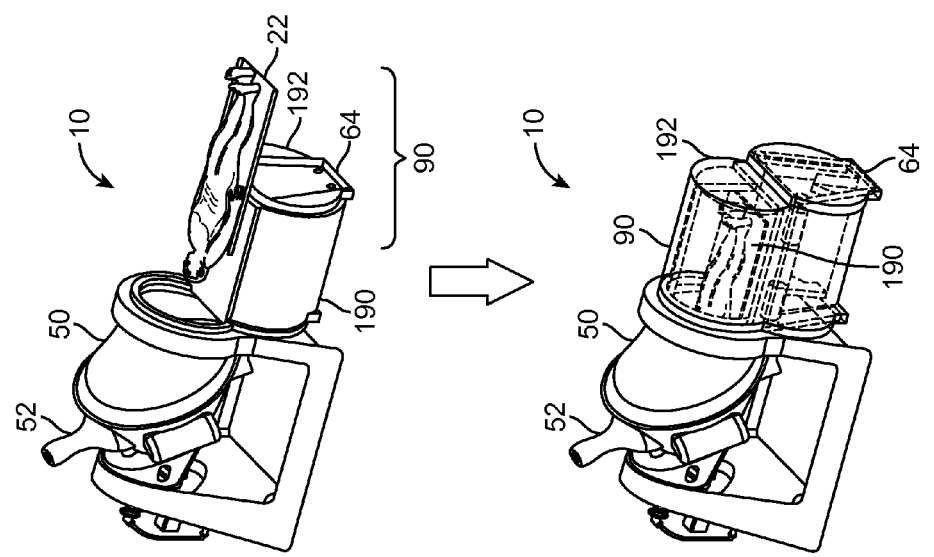

FIG. 3K illustrates another variation of the system 10, particularly showing the system having a plurality of shields 90a-90c. Each of the shields 90a, 90b has a left portion and a right portion, which may be retracted below the patient support 22 and/or next to the positioner 64. After the patient has been placed on the patient support 22, the left and right portions of each of the shields 90a, 90b may be moved mechanically upward to a closed position. Also, the shield 90c may be placed at an open position below the patient support 22. After the patient has been placed on the patient support 22, the shield 90c may be rotated about a hinge to swing the shield 90c to a closed position. The shields 90a-90c collectively function to block (attenuate) radiation emitting out of the capsule 16 that results from the operation of the radiation source 18, while allowing parts of the patient to be visible from outside the system 10. In some embodiments, a shielding wall (e.g., lead glass) may be coupled between the shields 90a, 90b to further attenuate radiation.

FIG. 4 illustrates another radiation system 10 in accordance with other embodiments. The radiation system 10 of FIG. 4 is similar to the system 10 of FIG. 1, except that the capsule 16 has a different configuration. As shown in the figure, the capsule 16 has a size that surrounds the patient 42. The capsule 16 has a first portion 50, and a second portion 52 that rotates relative to the first portion 50 about axis 54. The second portion 52 of the capsule 16 carries the radiation source 18, which is configured to deliver treatment radiation and/or diagnostic radiation. During use, the second portion 52 of the capsule 16 rotates about the axis 54 to thereby place the radiation source 18 at different gantry position with respect to the portion 40 of the patient 42 that is desired to be treated and/or imaged. The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. In other embodiments, the SID/SAD may have other values (e.g., a value that is larger than 600 mm). In some embodiments, the portions 50, 52 may be coupled to each other using a tongue-and-groove mechanism, or any of other mechanisms that can prevent leakage of radiation from within the capsule. Also, in some embodiments, the portion 50 may include a door that allows the patient to enter the capsule 16. In other embodiments, the portion 50 may be detachably coupled to the support 22 so that the portion 50 may be removed from the support 22 to allow positioning of the support 22 with the patient thereon. Then the portion 50 may be coupled (e.g., moveably coupled) to the support 22. As shown in the figure, the capsule 16 has a sufficient large size so that the patient may sit upright if needed. Also, the patient may be positioned by moving the support 22 relative to the capsule 16 so that different parts (such as the head, torso, etc.) of the patient may be placed at the isocenter.

In some embodiments, the capsule 16 may optionally be configured to also rotate about an axis that is perpendicular to the axis 54. For example, in some embodiments, the capsule 16 may also be configured to rotate about an axis that coincides with an isocenter 200 of the system 10, and that extends perpendicular to the axis 54 out of the page of the figure. The support 22 may be configured to translate the patient 42 (e.g., in the directions represented by the arrows 202) to thereby place different parts of the patient 42 at the isocenter 200.

It should be noted that any of the features related to shielding discussed with reference to the embodiments of FIG. 1 may be included in the embodiments of FIG. 4. For example, in some embodiments, the capsule 16 includes a shielding material that is configured to block at least some of the radiation that is resulted from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such a feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such a feature is advantageous because it allows the radiation system 10 to be useable at any location within the building, or at any facility, with minimal retrofit to be done to the building to provide radiation shielding.

Also, in further embodiments, the system 10 of FIG. 4 may optionally include one or more shields 90, as similarly discussed. The shield(s) 90 and the capsule 16 may cooperate to block off at least 98%, and preferably at least 99.9%, and even more preferably at least 99.999%, of the radiation resulted from an operation of the radiation source 18 in some embodiments. In other embodiments, the shield(s) 90 themselves may block off most of the radiation resulted from an operation of the radiation source 18.

In some embodiments, movement of the components of the system 10 of FIG. 4 (e.g., the capsule 16, the second portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 5:
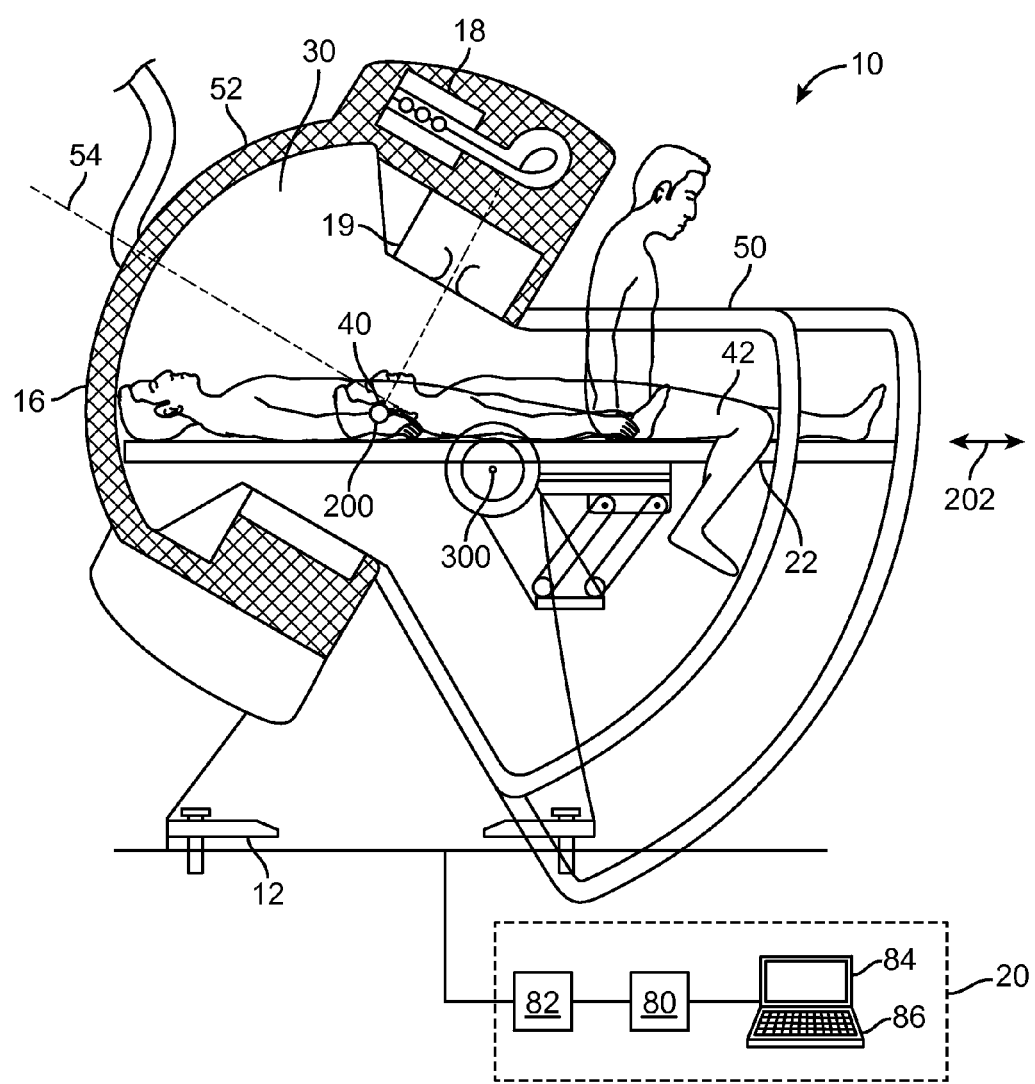
FIG. 5 illustrates another radiation system in accordance with other embodiments.

FIG. 5 illustrates another radiation system 10 in accordance with other embodiments. The radiation system 10 of FIG. 5 is similar to the system 10 of FIG. 4, except that the capsule 16 has a different configuration. As shown in the figure, the capsule 16 provides a complete enclosure that surrounds the entire patient 42 and the support 22. The radiation system 10 of FIG. 5 is similar to the embodiment of FIG. 4, except that the entire patient support 22 is contained within the space defined by the first portion 50 and the second portion 52. The capsule 16 has a first portion 50, and a second portion 52 that rotates relative to the first portion 50 about axis 54. In the illustrated embodiments, each of the first and second portions 50, 52 has a hollow dome shape. In other embodiments, the portions 50, 52 may have other shapes. Part of the capsule 16 may be a door that is moveably coupled to the rest of the capsule 16 to thereby allow the patient 42 to enter into and exit out of the capsule 16. The second portion 52 of the capsule 16 carries the radiation source 18, which is configured to deliver treatment radiation and/or diagnostic radiation. During use, the second portion 52 of the capsule 16 rotates about the axis 54 to thereby place the radiation source 18 at different gantry position with respect to the portion 40 of the patient 42 that is desired to be treated and/or imaged. The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. In other embodiments, the SID/SAD may have other values (e.g., a value that is larger than 600 mm).

In some embodiments, the capsule 16 may optionally be configured to also rotate about an axis that is perpendicular to the axis 54. For example, in some embodiments, the capsule 16 may also be configured to rotate about an axis that coincides with an isocenter 200 of the system 10, and that extends perpendicular to the axis 54 out of the page of the figure. In another example, the capsule 16 may be configured to rotate about axis 300, which is offset from the isocenter 200, and extends out of the page of the figure in a direction that is perpendicular to the axis 54. In some embodiments, the patient support 22 inside the capsule 16 may be coupled to the structural support 12 outside the capsule 16 through a shaft/hinge that extends through the wall of the capsule 16 that connects to the support 12. Such configuration allows the patient support 22 to remain rotationally fixed relative to the support 12 as the capsule 16 is rotated about the axis through the isocenter 200 or the axis 300. Such configuration also allows the capsule 16 to rotate relative to the patient support 22 without carrying the patient support 22 with it as it rotates. The support 22 may be configured to translate the patient 42 (e.g., in the directions represented by the arrows 202) to thereby place different parts of the patient 42 at the isocenter 200. The support 22 may also be configured to move in different degrees of freedom, such as those described with reference to the embodiments of FIG. 1.

It should be noted that any of the features related to shielding discussed with reference to the embodiments of FIG. 1 may be included in the embodiments of FIG. 5. For example, in some embodiments, the capsule 16 includes a shielding material that is configured to block at least some of the radiation that results from an operation of the radiation source 18. In some embodiments, the shielding material may be used to make the wall of the capsule 16. In other embodiments, the shielding material may be coupled to the wall of the capsule 16. For examples, the shielding material may be coupled to an outside surface of the wall of the capsule 16, an inside surface of the wall of the capsule 16, or may be a layer that is embedded within the wall of the capsule 16. In addition, in other embodiments, the shielding material may be in a form of multiple layers that are coupled to the capsule 16, with one or more layers coupled to an outside surface of the wall of the capsule 16, one or more layers embedded in the wall of the capsule 16, one or more layers coupled to an inside surface of the wall of the capsule 16, or combination thereof. Also, in some embodiments, the shielding material may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide shielding at a facility building, such as at a hospital. Such a feature is advantageous because it allows the radiation system 10 to be useable at any location within the building, or at any facility, without requiring expensive retrofit to be done to the building to provide radiation shielding. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such a feature is advantageous because it allows the radiation system 10 to be useable at any location within the building, or at any facility, with minimal retrofit to be done to the building to provide radiation shielding.

Also, in further embodiments, the system 10 of FIG. 5 may optionally include one or more shields 90, as similarly discussed. The shield(s) 90 and the capsule 16 may cooperate to block off at least 98%, and preferably at least 99.9%, and even more preferably at least 99.999%, of the radiation resulted from an operation of the radiation source 18 in some embodiments. In other embodiments, the shield(s) 90 themselves may block off most of the radiation resulted from an operation of the radiation source 18.

In some embodiments, movement of the components of the system 10 of FIG. 5 (e.g., the capsule 16, the second portion 52, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

Figure 6:
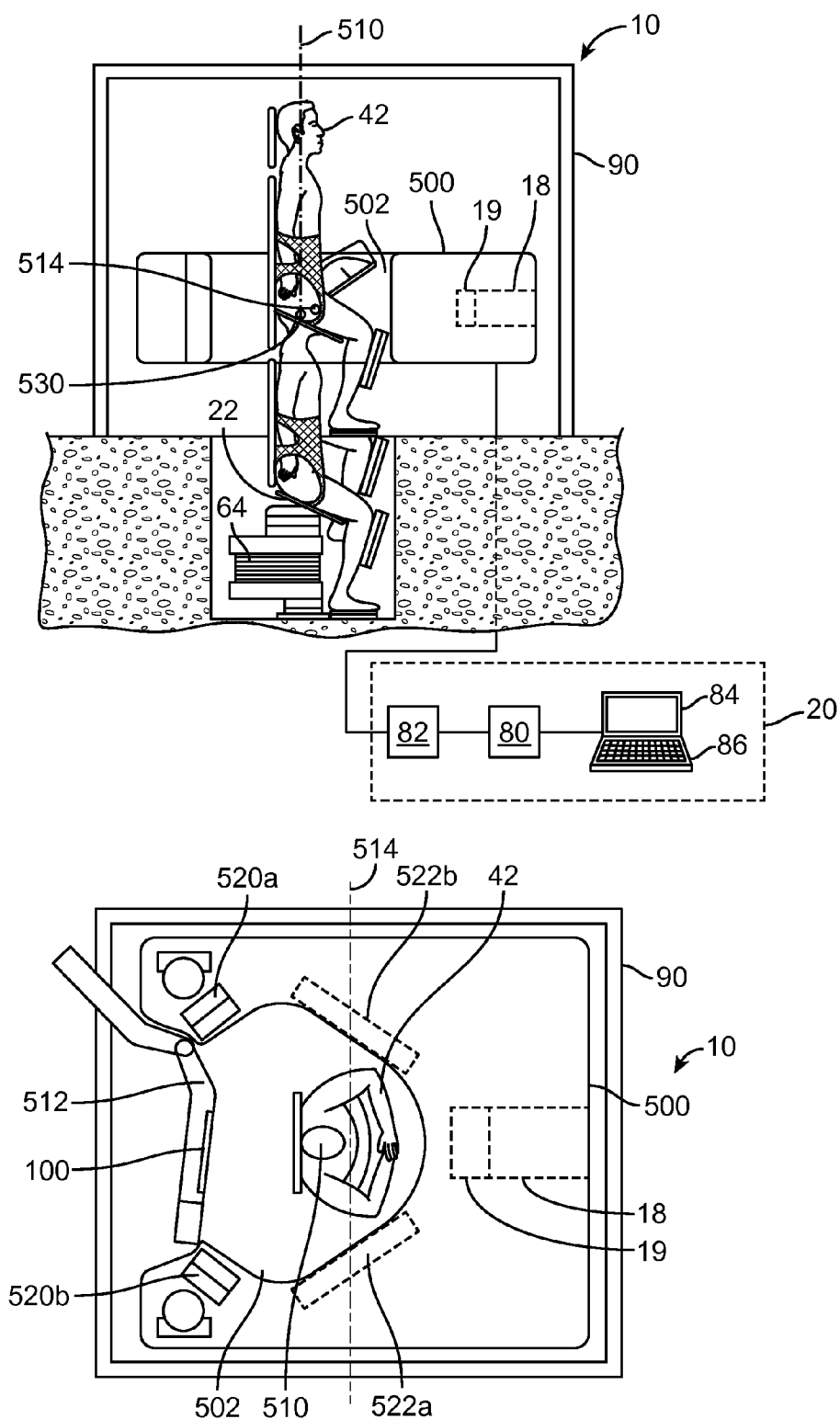
FIG. 6 illustrates another radiation system in accordance with other embodiments.

FIG. 6 illustrates another radiation system 10 in accordance with other embodiments. The system 10 includes a patient support 22, a gantry 500, a radiation source 18 coupled to the gantry 500, and a collimator 19 for configuring radiation (e.g., changing a shape of the radiation beam) provided by the radiation source 18. The gantry 500 may be rectangular block with an interior space 502 for accommodating the patient support 22. In the illustrated embodiments, the patient support 22 is configured to support the patient 42 in an upright position. In one implementation, the patient support 22 may be implemented as a medical chair. The patient support 22 is also configured to rotate by a positioner 64 about a vertical axis 510 during use, so that the patient 42 may be rotated relative to the radiation source 18. Because the patient 42 is rotated by the patient support 22, the gantry 500 carrying the radiation source 18 does not need to be rotated. Instead, the gantry 500 is configured to move vertically in an upward or downward position so that the radiation source 18 may deliver radiation to different part(s) of the patient 42. In such cases, the gantry 500 may be slidably coupled to a vertical rail, for example.

In other embodiments, the positioner 64 may also be configured to move the patient support 22 vertically upward or downward. In such cases, the gantry 500 is not required to move vertically (e.g., the gantry 500 may be fixedly mounted to a structure, such as a component of the system 10, a part of a room, etc.). However, in some embodiments, the gantry 500 may optionally be configured to move vertically anyway. In further embodiments, the gantry 500 may optionally be configured to tilt relative to the patient 42. For example, in some embodiments, the gantry 500 may be configured to rotate about a horizontal axis 514 that intersects the vertical axis 510, so that the radiation source 18 may deliver radiation towards the patient 42 at different angular positions.

As shown in the figure, the gantry 500 includes a door 512 for allowing the patient 42 to enter into the space 502 surrounded by the gantry 500. The door 512 may optionally include an imager 100, so that when the door 512 is closed, the imager 100 is at an operative position relative to the radiation source 18. During use, radiation from the radiation source 18 enters the patient 42 and exits the patient 42 to reach the imager 100. The imager 100 generates image data in response to the radiation received thereon. The radiation may be treatment radiation in some embodiments, or diagnostic radiation in other embodiments. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

The radiation source 18 may be the same radiation source 18 as that discussed with reference to FIG. 1. In the illustrated embodiments, the SID/SAD is less than 800 mm, and more preferably less than 600 mm, and even more preferably about 415 mm (415 mm±40 mm). Also, in some embodiments, the SID/SAD value for the radiation system 10 is less than those in existing radiation machines. Such configuration allows the radiation source 18 to provide less radiation energy compared to existing treatment radiation sources, and still sufficiently treat a target (e.g., tumor). Also, because of the reduction in energy requirement, the amount of shielding that is needed for a facility building is substantially reduced, or may be eliminated. In other embodiments, the SID/SAD may have other values (e.g., a value that is larger than 600 mm).

In the illustrated embodiments, the radiation system 10 also includes a shield 90 surrounding the gantry 500. The shield 90 is configured to block at least some of the radiation that results from an operation of the radiation source 18. In some embodiments, the shield 90 may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90 may be configured to block off a sufficient amount of radiation resulted from an operation of the radiation source 18 so that it obviates the need to provide shielding at a facility building, such as at a hospital. Such a feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90 may be configured to block off a sufficient amount of radiation resulted from an operation of the radiation source 18 so that it reduces a significant amount (e.g., at least 50%, and more preferably, at least 90%) of the shielding requirement at a building. Such a feature is advantageous because it allows the radiation system 10 to be useable at any location within the building, or at any facility, with minimal retrofit to be done to the building to provide radiation shielding.

In some embodiments, movement of the components of the system 10 of FIG. 6 (e.g., the support 22, the source 18, etc.) may be performed based on a treatment plan. Also, in some embodiments, when determining the treatment plan that is to be carried out using the system 10, movement constraint associated with the degrees of freedom of the moving parts of the system 10 may be incorporated in the treatment planning.

As shown in the figure, the radiation system 10 may optionally further include two imaging sources 520a, 520b (e.g., two x-ray sources) and two corresponding imagers 522a, 522b that are in corresponding operative positions relative to the imaging sources 520a, 520b. In other embodiments, the imaging sources 520a, 520b and the imagers 522a, 522b may be coupled to another structure that is not a part of the radiation system 10. For example, in other embodiments, the imaging sources 520a, 520b and the imagers 522a, 522b may be mounted to a room (e.g., to a ceiling, a floor), or to a support that is movable independent of the gantry 500. During use, radiation from the imaging sources 520a, 520b enters the patient 42 and exits the patient 42 to reach the corresponding imagers 522a, 522b. The imagers 522a, 522b generate image data in response to the radiation received thereon. In some embodiments, the image data may be generated before a treatment session using diagnostic radiation to setup the patient 42 (e.g., before treatment radiation is delivered to the patient 42). In other embodiments, the image data may be generated during a treatment session to confirm an accuracy of treatment radiation delivery. In further embodiments, the image data may be processed by the processor 80, which adjusts a treatment plan based on the processed image data. For example, if the processor 80 determines from the image data that a part of a target region is not receiving enough radiation, and/or if a critical (e.g., healthy) tissue is receiving too much radiation, the processor 80 may then adjust the treatment plan so that a future delivery of treatment radiation would result in more radiation being delivered to the target region and/or less radiation being delivered to the critical tissue.

In other embodiments, the radiation system 10 may not include both imaging sources 520a, 520b and both imagers 522a, 522b. Instead, the radiation system 10 may include only one imaging source, and one corresponding imager. In further embodiments, the radiation system 10 may not include any imaging source and imager.

Figure 7:
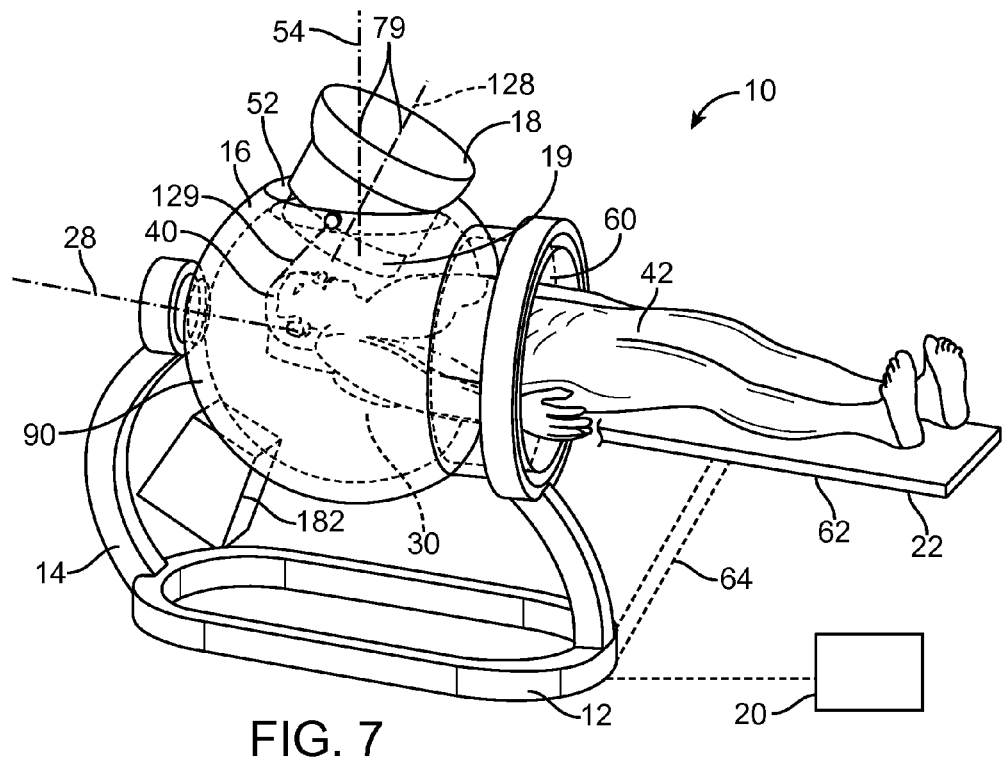
FIG. 7 illustrates another radiation system in accordance with other embodiments.

FIG. 7 illustrates another radiation system 10 in accordance with some embodiments. The radiation system 10 includes a base 12, a support 14, a capsule 16, a radiation source 18, a collimator 19, a control system 20, and a patient support 22. The system 10 is the same as that described with reference to FIG. 1, except that the various components (e.g., the base 12, capsule 16, radiation source 18, etc.) have different sizes and/or shapes. In the illustrated embodiments, the base 12 and the support 14 are manufactured as a single piece with an unity configuration. In other embodiments, the base 12 and the support 14 may be separate components that are coupled together. Also, in further embodiments, the support 14 may be moveable relative to the base 12 in one or more degrees of freedom. In still further embodiments, the base 12 may be considered to be a part of the support 14.

In the illustrated embodiments, the capsule 16 is rotatably coupled to the support 14 about axis 28, and defines a space 30 for accommodating at least a portion 40 of a patient 42. In the illustrated embodiments, the portion 40 is a head of the patient 42. In other embodiments, the portion 40 may include other part(s) of the patient 42. For example, in other embodiments, the portion 40 may include both the head and the shoulders of the patient 42. In further embodiments, the portion 40 may include a body of the patient 42.

As shown in the figure, the capsule 16 includes a first capsule portion 50 and a second capsule portion 52 that is rotatable relative to the first capsule portion 50 about axis 54. In one implementation, the first capsule portion 50 and the second capsule portion 52 may be rotatably coupled to each other using a tongue-and-groove mechanism, which may be more effective in preventing leakage of radiation between the coupling of the portions 50, 52 (because part of the tongue-and-groove mechanism may attenuate some of the radiation). In other embodiments, the first and second capsule portions 50, 52 may be coupled using other mechanisms. In the illustrated embodiments, the first and second capsule portions 50, 52 define an interior surface that has a partial spherical configuration. In other embodiments, the interior surface may have other configurations, and is not limited to a spherical configuration. Also, in some embodiments, the second capsule portion 52 may be a part of the radiation source 18. In some embodiments, the portion 50 may be a hollow sphere with an open top. The circumference of the open top is slotted to receive pins that extend from radiation source 18 or from the portion 62. The pins are located along an axis 129 so radiation source 18 can pivot along axis 129. The pins also allow radiation source 18 to rotate about axis 54. In some embodiments, the beam stop 182 may be fixed relative to the capsule 16. In such cases, the beam stop 182 may have a sufficiently large area to block radiation from the radiation source 18 no matter which direction the radiation source 18 is aiming. In other embodiments, the beam stop 182 may move in conjunction with the radiation source 18 so that the beam stop 182 is always at the opposite side facing the radiation source 18. For example, the beam stop 182 may be coupled to the radiation source 18 via a C-arm, or other mechanical supports in some embodiments.

As shown in FIG. 7, the radiation source 18 is tilted so that it forms an angle 79 (e.g., a non-zero acute angle) relative to the axis 54. Such configuration allows the radiation source 18 to deliver radiation from different angles towards the portion 40 of the patient 42 as the second portion 52 rotates relative to the first portion 50 about the axis 54. In other embodiments, the capsule 16 may be rotated about the axis 28 to turn the radiation source 18 around the patient so that radiation may be delivered to the patient from different angles. In some embodiments, the rotation of the second portion 52 about the axis 54, and the rotation of the capsule about the axis 28, may be performed one after the other. Alternatively, the rotation of the second portion 52 about the axis 54, and the rotation of the capsule about the axis 28, may be performed simultaneously. In some embodiments, the radiation source 18 may be configured to be tiltable relative to the second portion 52.

As shown in FIG. 7, the capsule 16 also includes an opening 60 for allowing the portion 40 of the patient 42 to go therethrough in order to reach the interior space 30 of the capsule 16. The patient support 22 includes a table 62 for supporting the patient 42, and a positioner 64 configured to translate the table 62 axially so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

It should be noted that any of the shielding features described with reference to the embodiments of FIG. 1 may be optionally applied for the embodiments of FIG. 7. For example, in some embodiments, any of the components (e.g., the capsule 16) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement. Also, in some embodiments, the radiation system 10 may optionally further include one or more shields (e.g., the shield(s) 90 described with reference to FIG. 1) for blocking radiation that is resulted from an operation of the radiation source 18. The shield(s) may be coupled to any of the components in the system 10.

Also, in some embodiments, the system 10 may optionally include an imager (similar to the imager 100 described with reference to FIG. 1) that cooperates with the radiation source 18 to obtain image(s). Furthermore, in some embodiments in which the radiation source 18 is a treatment radiation source, the system 10 may optionally further include an imager on one side of the capsule 16 and an imaging source located on the opposite side of the capsule 16 for obtaining images before, during, and/or after a treatment session.

Figure 8A:
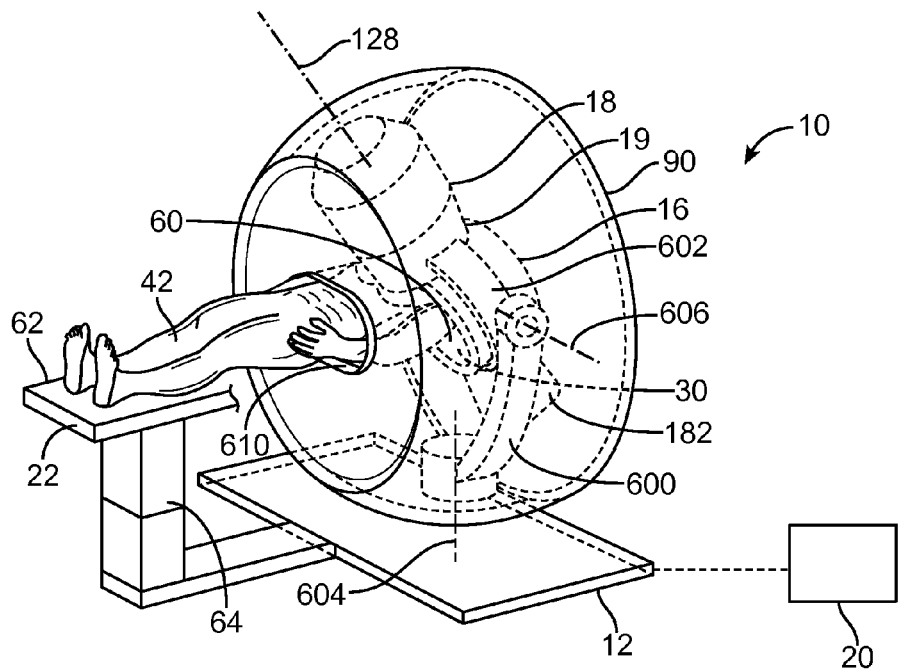
FIGS. 8A-8D illustrate another radiation system in accordance with other embodiments.

FIG. 8A illustrates another radiation system 10 in accordance with some embodiments. The radiation system 10 includes a base 12, a capsule 16, a radiation source 18, a collimator 19, a control system 20, and a patient support 22. These components are similar to those described with reference to the embodiments of FIG. 1. The system 10 also includes a first support 600 (e.g., a first gimbal) that is rotatable relative to the base about a first axis 604, a second support 602 (e.g., a second gimbal) that is rotatably coupled to the first support 600 so that the second support 602 can rotate relative to the first support 600 about a second axis 606. Radiation source 18 is coupled to second support 602. The capsule 16 is rotatably coupled (e.g., via one or more hinges) to the second support 602 so that the capsule 16 can rotate relative to the second support 602 about the axis 128 of the radiation source 18. The capsule 16 has a partial sphere configuration that is hollow. In other embodiments, the capsule 16 may have other shapes. In the illustrated embodiments, the second axis 606 of rotation is perpendicular to the first axis 604 of rotation, and the axis 128 is also perpendicular to the axis 606. In other embodiments, the second axis 606 may form a non-perpendicular angle relative to the first axis 604. Also, in other embodiments, the axis 128 may form a non-perpendicular angle relative to the second axis 606. In some embodiments, the radiation source 18 may be axially translated along the axis 128 so that it is moved closer towards the patient 42 or further away from the patient 42 (like that shown in the embodiments of FIG. 11A, which will be discussed further below). In other embodiments, the radiation source 18 may be axially fixed along the axis 128.

In the illustrated embodiments, the capsule 16 defines a space 30 for accommodating at least a portion of a patient 42. In the illustrated embodiments, the portion is a head of the patient 42. In other embodiments, the portion may include other part(s) of the patient 42. For example, in other embodiments, the portion 40 may include both the head and the shoulders of the patient 42. In further embodiments, the portion 40 may include a body of the patient 42.

As shown in the figure, the capsule 16 also includes an opening 60 for allowing the portion of the patient 42 to go therethrough in order to reach the interior space 30 of the capsule 16. The patient support 22 includes a table 62 for supporting the patient 42, and a positioner 64 configured to translate the table 62 axially so that the portion of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

Figure 8B:
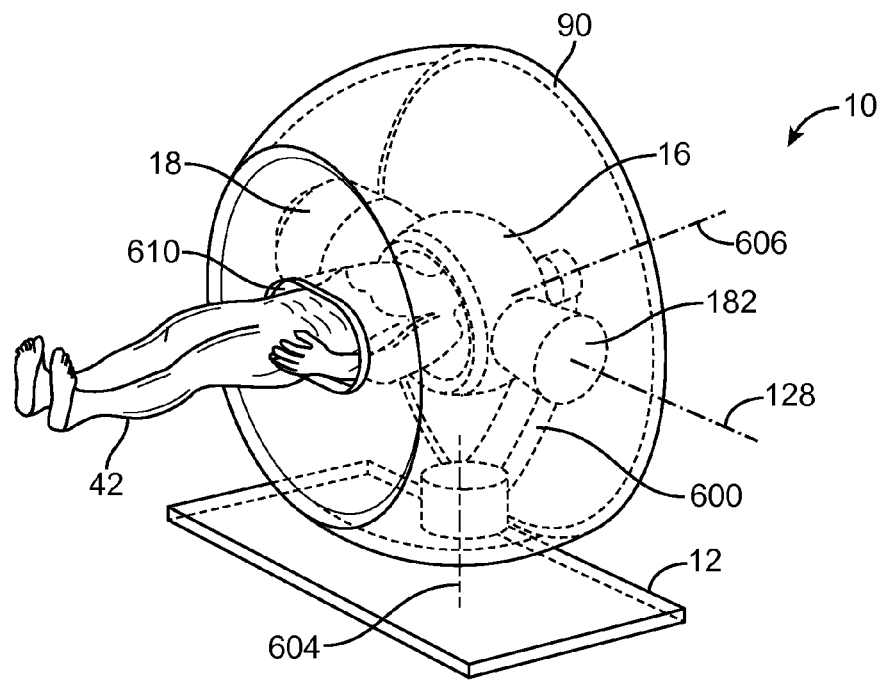
Figure 8C:
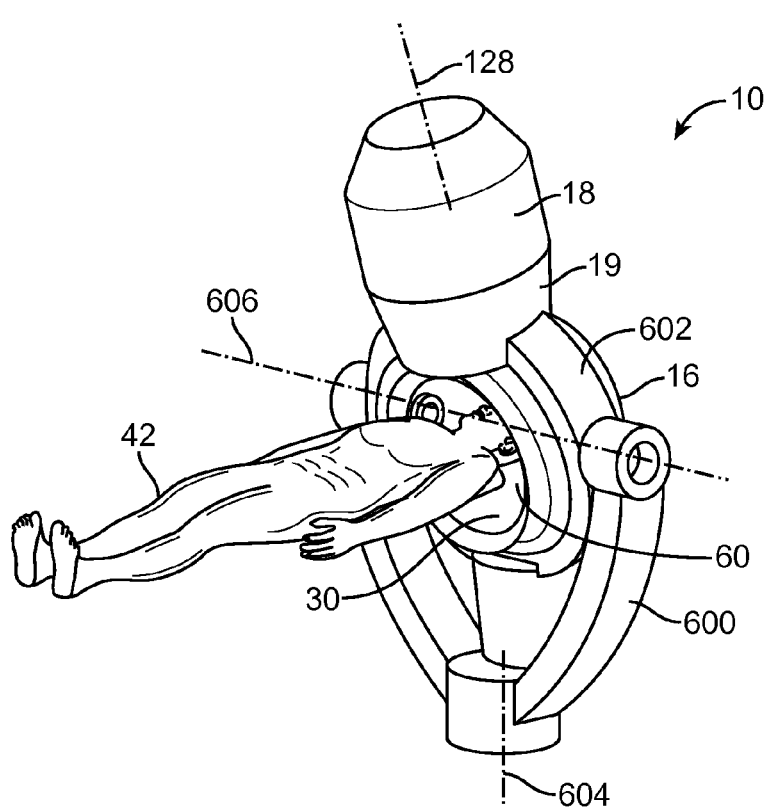
Figure 8D:
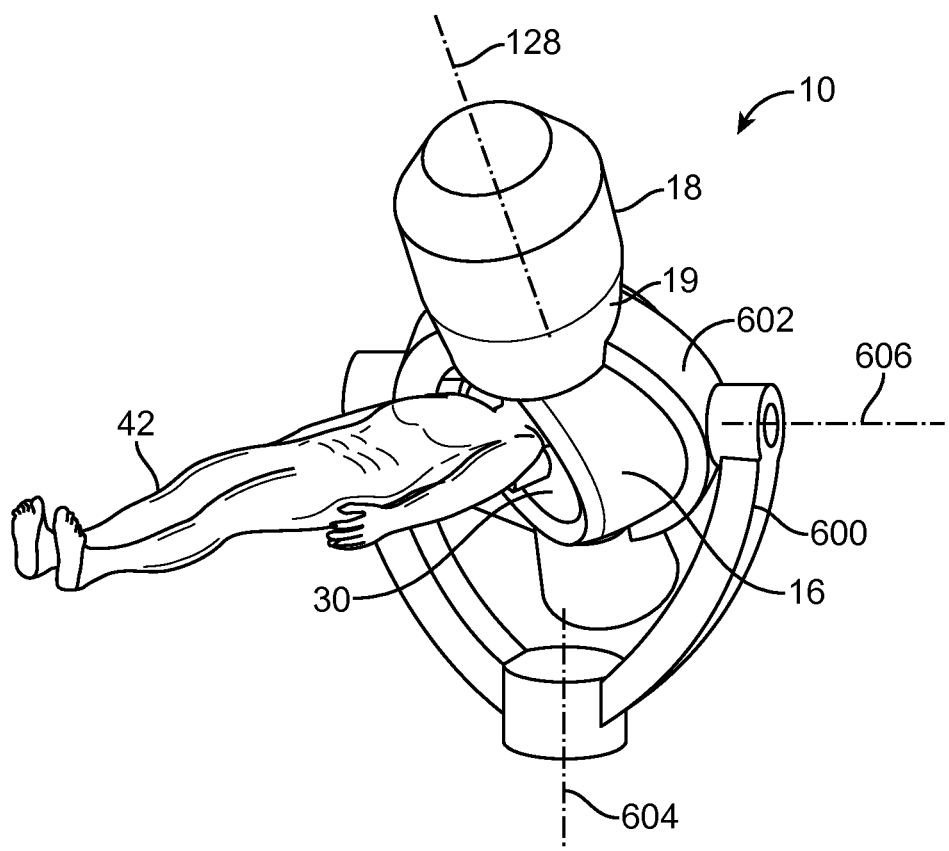

FIG. 8B illustrates the system 10 of FIG. 8A, particularly showing the support 600 having been rotated about the axis 604, and the support 602 (carrying the radiation source 18 and the capsule 16) having been rotated about the axis 606. FIGS. 8C-8D illustrate the system 10 of FIG. 8A, but with the shield 90 removed to show the components more clearly. As shown in FIG. 8C, the capsule 16 may be rotated about the axis 128 relative to the support 602. As illustrated in the figures, the different degrees of movement by the different components 16, 600, 602 allow the radiation source 18 to be placed at different angular positions relative to the patient 42 so that radiation beam can be directed towards the patient 42 from different directions. In some embodiments, movements of the first support 600, second support 602, and the capsule 16 may occur simultaneously. In other embodiments, the movements of the first support 600, second support 602, and the capsule 16 may occur one after the other.

In the illustrated embodiments, the system 10 also includes a shield 90 disposed around the capsule 16. The shield 90 includes an opening 610 for allowing at least a part of the patient 42 to be inserted therethrough.

It should be noted that any of the shielding features described with reference to the embodiments of FIG. 1 may be optionally applied for the embodiments of FIG. 8. For example, in some embodiments, any of the components (e.g., the capsule 16, the shield 90, or both) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement.

Also, in the illustrated embodiments of FIG. 8A, the shield 90 is configured to block at least some of the radiation that is resulted from an operation of the radiation source 18. In some embodiments, the shield 90 may be configured (e.g., have certain material density, certain geometry, and/or certain thickness) to block radiation (either alone or in combination with the capsule 16) so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90 may be configured to block off (either alone or in combination with the capsule 16) a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90 may be configured to block off (either alone or in combination with the capsule 16) a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield(s) 90 may be configured to block off all or most of the radiation resulted from an operation of the radiation source 18. In such cases, the capsule 16 may not include any shielding material.

Also, in some embodiments, the system 10 of FIG. 8A may optionally include an imager (similar to the imager 100 described with reference to FIG. 1) that cooperates with the radiation source 18 to obtain image(s). Furthermore, in some embodiments in which the radiation source 18 is a treatment radiation source, the system 10 may optionally further include an imager on one side of the capsule 16 and an imaging source located on the opposite side of the capsule 16 for obtaining images before, during, and/or after a treatment session.

Figure 9A:
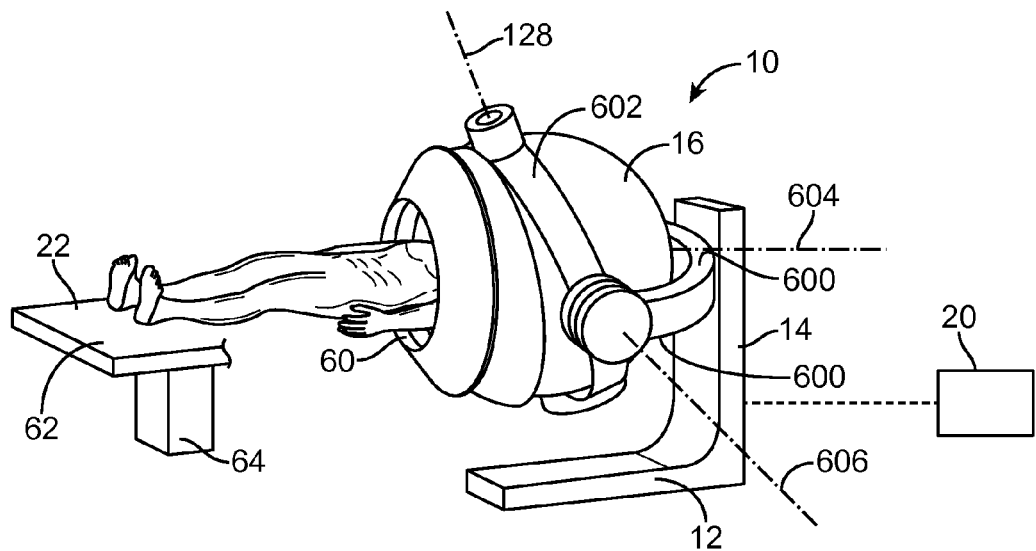
FIGS. 9A-9G illustrate another radiation system in accordance with other embodiments.
Figure 9B:
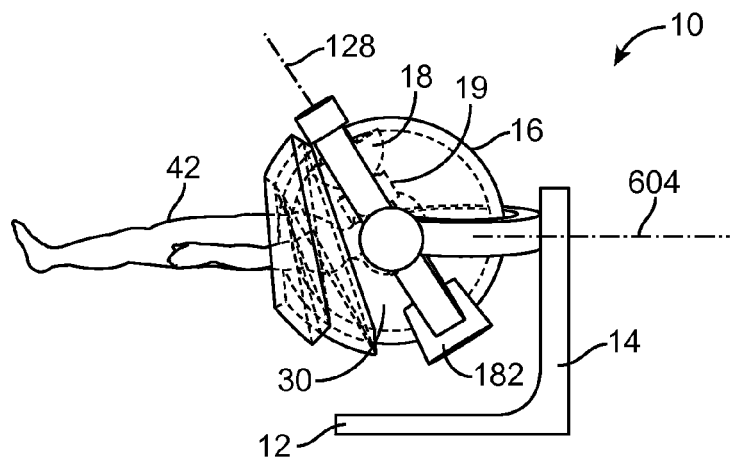
Figure 9C:
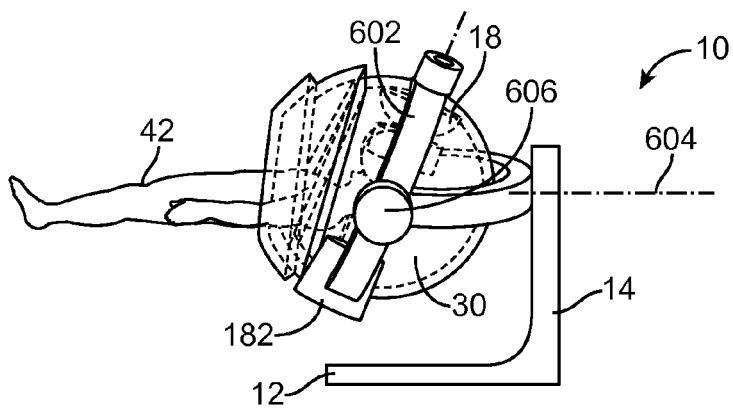
Figure 9D:
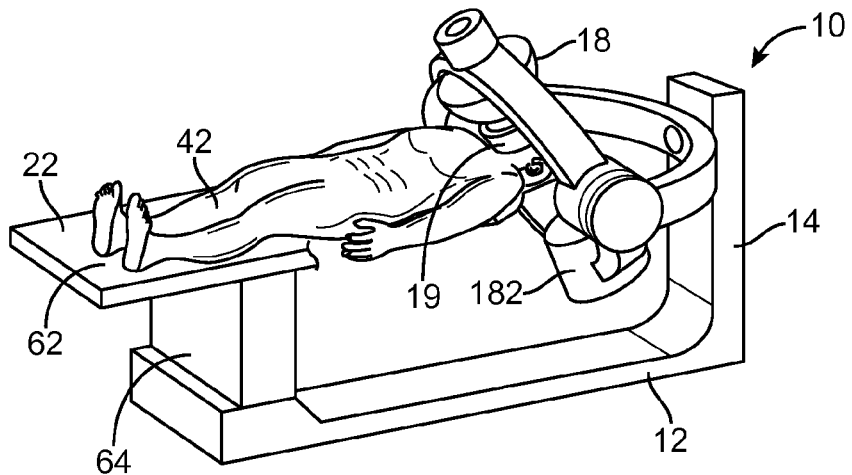

FIGS. 9A-9B and 9D illustrate another radiation system 10 in accordance with some embodiments. The radiation system 10 includes a base 12, a support 14, a capsule 16, a radiation source 18, a collimator 19, a control system 20, and a patient support 22. These components are similar to those described with reference to the embodiments of FIGS. 1 and 8A. In particular, the system 10 of FIG. 9A is similar to the embodiments of FIG. 8A, except that the support 600 is now mounted to support 14 instead of to the base 12. Also, the system 10 of FIG. 9A includes two circular plates at one end of the capsule 16 where the patient enters the capsule 16. The plates provides additional shielding to block radiation resulted from the operation of the radiation source.

In FIG. 9D, the capsule 16 is removed to more clearly show the radiation source 18 and the collimator 19. The system 10 also includes a first support 600 that is rotatable relative to the support 14 about a first axis 604, a second support 602 that is rotatably coupled to the first support 600 so that the second support 602 can rotate relative to the first support 600 about a second axis 606. The capsule 16 is rotatably coupled to the second support 602 so that the capsule 16 can rotate relative to the second support 602 about the axis 128 of the radiation source 18. In other embodiments, the capsule 16 may be fixedly secured relative to the second support 602. The second support 602 is configured to carry the radiation source 18 and the collimator 19 so that movement of the second support 602 will cause a corresponding movement of the radiation source 18 and the collimator 19. In the illustrated embodiments, the second axis 606 of rotation is perpendicular to the first axis 604 of rotation, and the axis 128 is also perpendicular to the axis 606. In other embodiments, the second axis 606 may form a non-perpendicular angle relative to the first axis 604. Also, in other embodiments, the axis 128 may form a non-perpendicular angle relative to the second axis 606. In some embodiments, the radiation source 18 may be axially translated along the axis 128 so that it is moved closer towards the patient 42 or further away from the patient 42. In other embodiments, the radiation source 18 may be axially fixed along the axis 128.

In the illustrated embodiments, the capsule 16 defines a space 30 for accommodating at least a portion of a patient 42. In the illustrated embodiments, the portion includes a head and a shoulder of the patient 42. In other embodiments, the portion may include other part(s) of the patient 42.

As shown in the figure, the capsule 16 also includes an opening 60 for allowing the portion of the patient 42 to go therethrough in order to reach the interior space 30 of the capsule 16. The patient support 22 includes a table 62 for supporting the patient 42, and a positioner 64 configured to translate the table 62 axially so that the portion of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

Figures 9E, 9F:
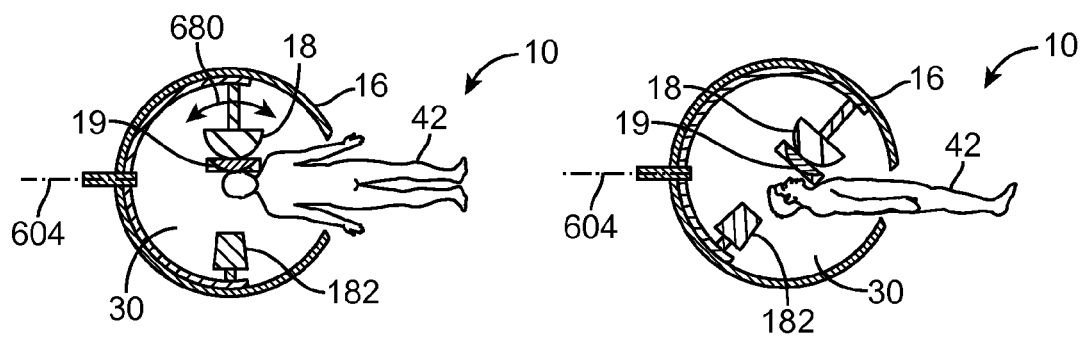
Figure 9G:
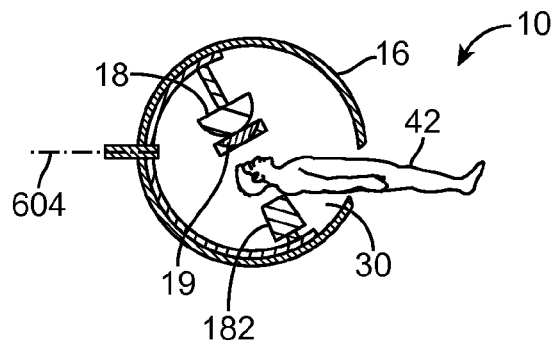

FIG. 9C illustrates the system 10 of FIG. 9A, particularly showing the support 602 (carrying the radiation source 18 and the collimator 19) having been rotated about the axis 606. As shown in FIG. 9E, in some embodiments, the first support 600 may be rotated about the axis 604 so that the radiation source 18 may be on one of the left and right sides of the patient 42. From the position shown in the figure, the second support 602 may be rotated about the axis 606 to place the radiation source 18 at different angular positions (as illustrated by the double-arrow 680). Alternatively, from the position shown in FIG. 9A, the second support 602 may be rotated about the axis 606 to place the radiation source 18 at different angular positions, such as the position shown in FIG. 9F, or the position shown in FIG. 9G. As shown in the above examples, regardless of the angular position of the support 600 relative to the support 14, the radiation source 18 and the collimator 19 may be rotated about the axis 606 (as represented by the double-arrow 680 in FIG. 9E). The different degrees of movement by the different components 600, 602 allow the radiation source 18 to be placed at different angular positions relative to the patient 42 so that radiation beam can be directed towards the patient 42 from different directions. In some embodiments, movements of the first support 600 and second support 602 may occur simultaneously. In other embodiments, the movements of the first support 600 and the second support 602 may occur one after the other.

It should be noted that any of the shielding features described with reference to the embodiments of FIG. 1 may be optionally applied for the embodiments of FIG. 9A. For example, in some embodiments, any of the components (e.g., the capsule 16) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement. Also, in some embodiments, the radiation system 10 may optionally further include one or more shields (e.g., the shield(s) 90 described with reference to FIG. 1) for blocking radiation that is resulted from an operation of the radiation source 18. The shield(s) may be coupled to any of the components in the system 10.

Also, in some embodiments, the system 10 of FIG. 9A may optionally include an imager (similar to the imager 100 described with reference to FIG. 1) that cooperates with the radiation source 18 to obtain image(s). Furthermore, in some embodiments in which the radiation source 18 is a treatment radiation source, the system 10 may optionally further include an imager on one side of the capsule 16 and an imaging source located on the opposite side of the capsule 16 for obtaining images before, during, and/or after a treatment session.

Figure 10:
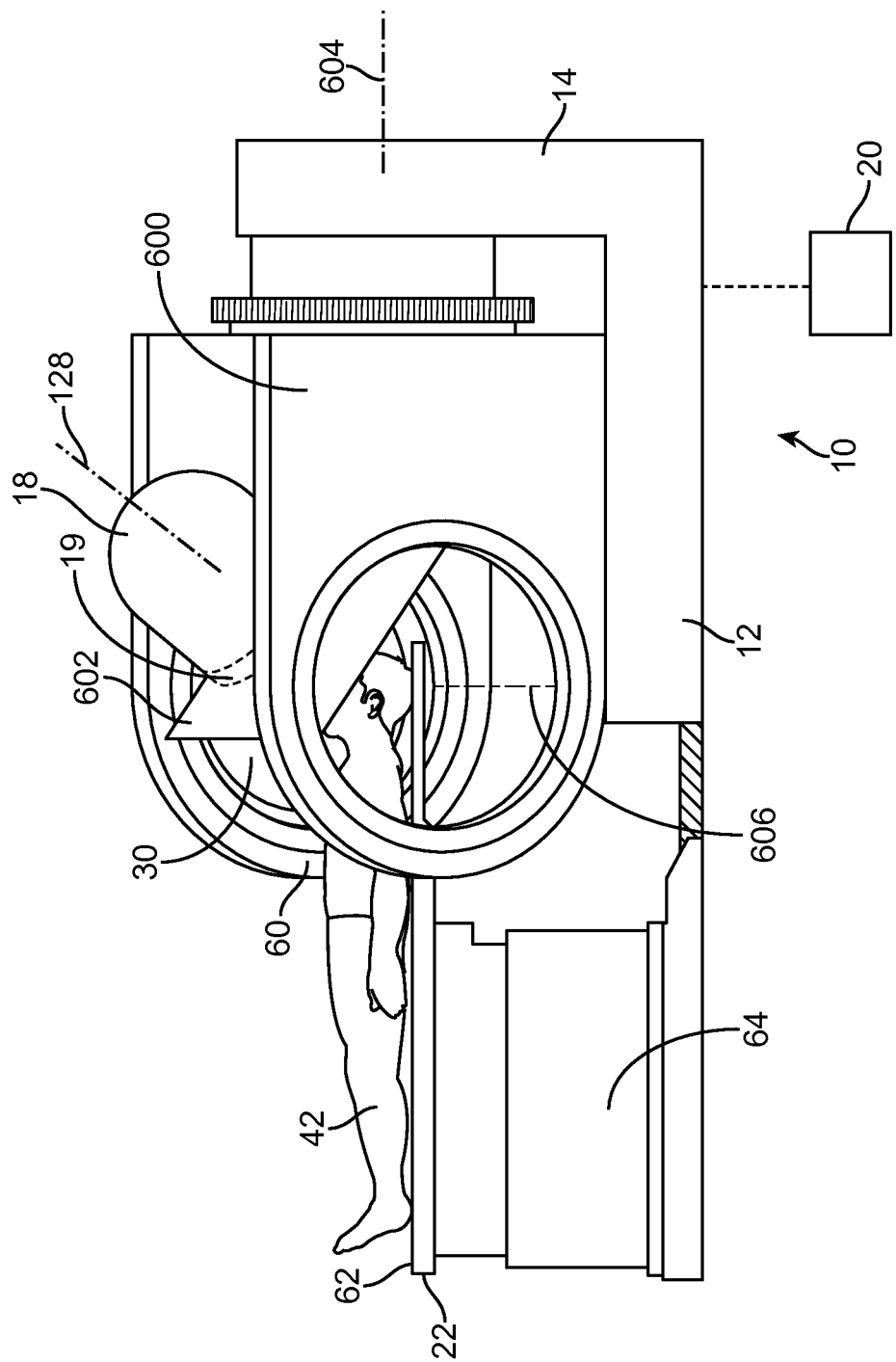
FIG. 10 illustrates another radiation system in accordance with other embodiments.

FIG. 10 illustrates another radiation system 10 in accordance with some embodiments. The radiation system 10 includes a base 12, a support 14, a radiation source 18, a collimator 19, a control system 20, and a patient support 22. These components are similar to those described with reference to the embodiments of FIG. 1. The system 10 also includes a capsule (not shown for clarity) that is coupled to the first support 600, the second support 602, or both. The capsule may be similar to the capsule 16 discussed previously, and may have any of the features discussed. Also, in other embodiments, part of the first support 600, part of the second support 602, or both, may form at least part (or all) of the capsule. The system 10 also includes a first support 600 that is rotatable relative to the support 14 about a first axis 604, a second support 602 that is rotatably coupled to the first support 600 so that the second support 602 can rotate relative to the first support 600 about a second axis 606. The second support 602 is configured to carry the radiation source 18 and the collimator 19 so that movement of the second support 602 will cause a corresponding movement of the radiation source 18 and the collimator 19. In the illustrated embodiments, the second axis 606 of rotation is perpendicular to the first axis 604 of rotation, and the axis 128 is also perpendicular to the axis 606. In other embodiments, the second axis 606 may form a non-perpendicular angle relative to the first axis 604. Also, in other embodiments, the axis 128 of the radiation source 18 may form a non-perpendicular angle relative to the second axis 606. In some embodiments, the radiation source 18 may be axially translated along the axis 128 so that it is moved closer towards the patient 42 or further away from the patient 42. In other embodiments, the radiation source 18 may be axially fixed along the axis 128.

As shown in the figure, the patient support 22 includes a table 62 for supporting the patient 42, and a positioner 64 configured to translate the table 62 axially so that the portion of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

As shown in FIG. 10, the system 10 is similar to the system 10 of FIG. 9A, except that the configuration of the first support 600, and the configuration of the second support 602 are different. In particular, the first support 600 includes two large ring bearing for allowing the second support 602 to be rotatably coupled thereto.

Figure 11A:
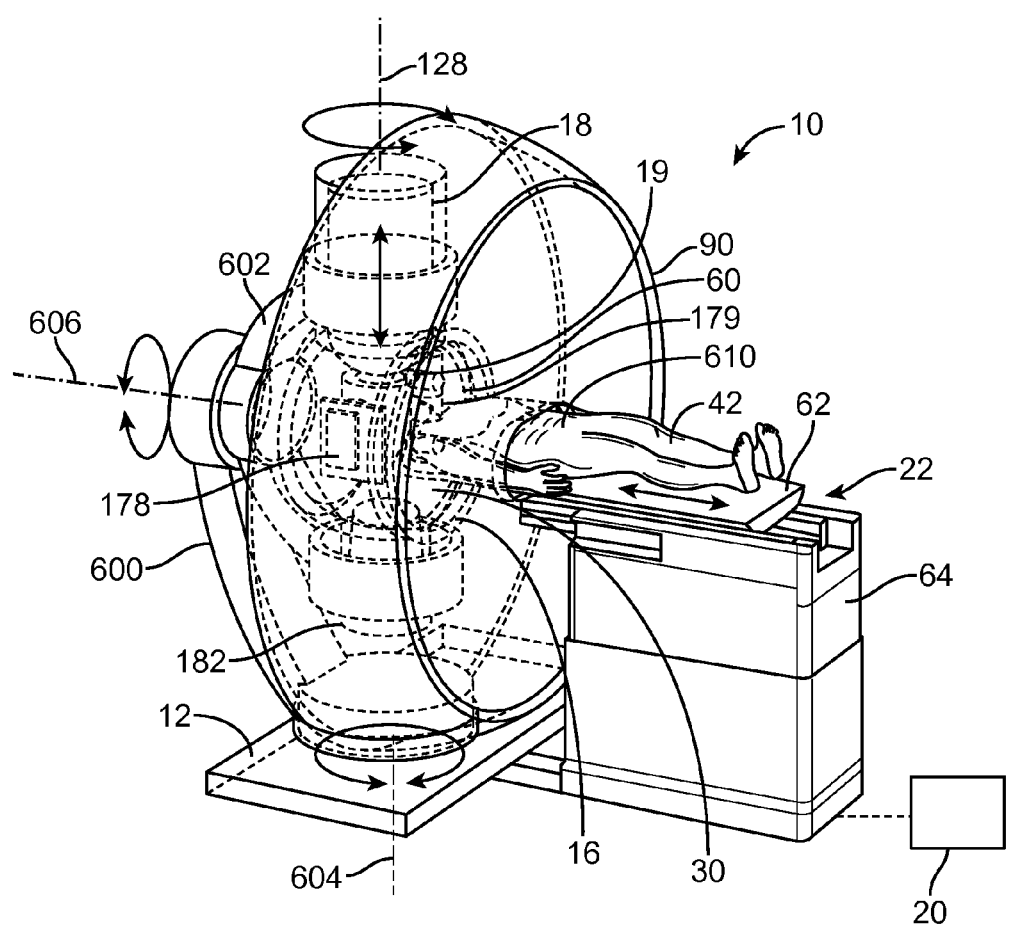
FIGS. 11A-11F illustrate other radiation systems in accordance with other embodiments.

FIG. 11A illustrates another radiation system 10 in accordance with some embodiments. The radiation system 10 includes a base 12, a capsule 16, a radiation source 18, a collimator 19, a control system 20, and a patient support 22. These components are similar to those described with reference to the embodiments of FIG. 8A. The system 10 also includes a first support 600 (e.g., a first gimbal) that is rotatable relative to the base about a first axis 604, a second support 602 (e.g., a second gimbal) that is rotatably coupled to the first support 600 so that the second support 602 can rotate relative to the first support 600 about a second axis 606. The capsule 16 is rotatably coupled to the second support 602 so that the capsule 16 can rotate relative to the second support 602 about the axis 128 of the radiation source 18. In other embodiments, the capsule 16 may be fixedly coupled to the second support 602. In the illustrated embodiments, the second axis 606 of rotation is perpendicular to the first axis 604 of rotation, and the axis 128 is also perpendicular to the axis 606. In other embodiments, the second axis 606 may form a non-perpendicular angle relative to the first axis 604. Also, in other embodiments, the axis 128 may form a non-perpendicular angle relative to the second axis 606. In some embodiments, the radiation source 18 may be axially translated along the axis 128 so that it is moved closer towards the patient 42 or further away from the patient 42. In other embodiments, the radiation source 18 may be axially fixed along the axis 128.

In the illustrated embodiments, the capsule 16 defines a space 30 for accommodating at least a portion of a patient 42. In the illustrated embodiments, the portion includes a head and a shoulder of the patient 42. In other embodiments, the portion may include other part(s) of the patient 42.

As shown in the figure, the capsule 16 also includes an opening 60 for allowing the portion of the patient 42 to go therethrough in order to reach the interior space 30 of the capsule 16. The patient support 22 includes a table 62 for supporting the patient 42, and a positioner 64 configured to translate the table 62 axially so that the portion of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

Figure 11B:
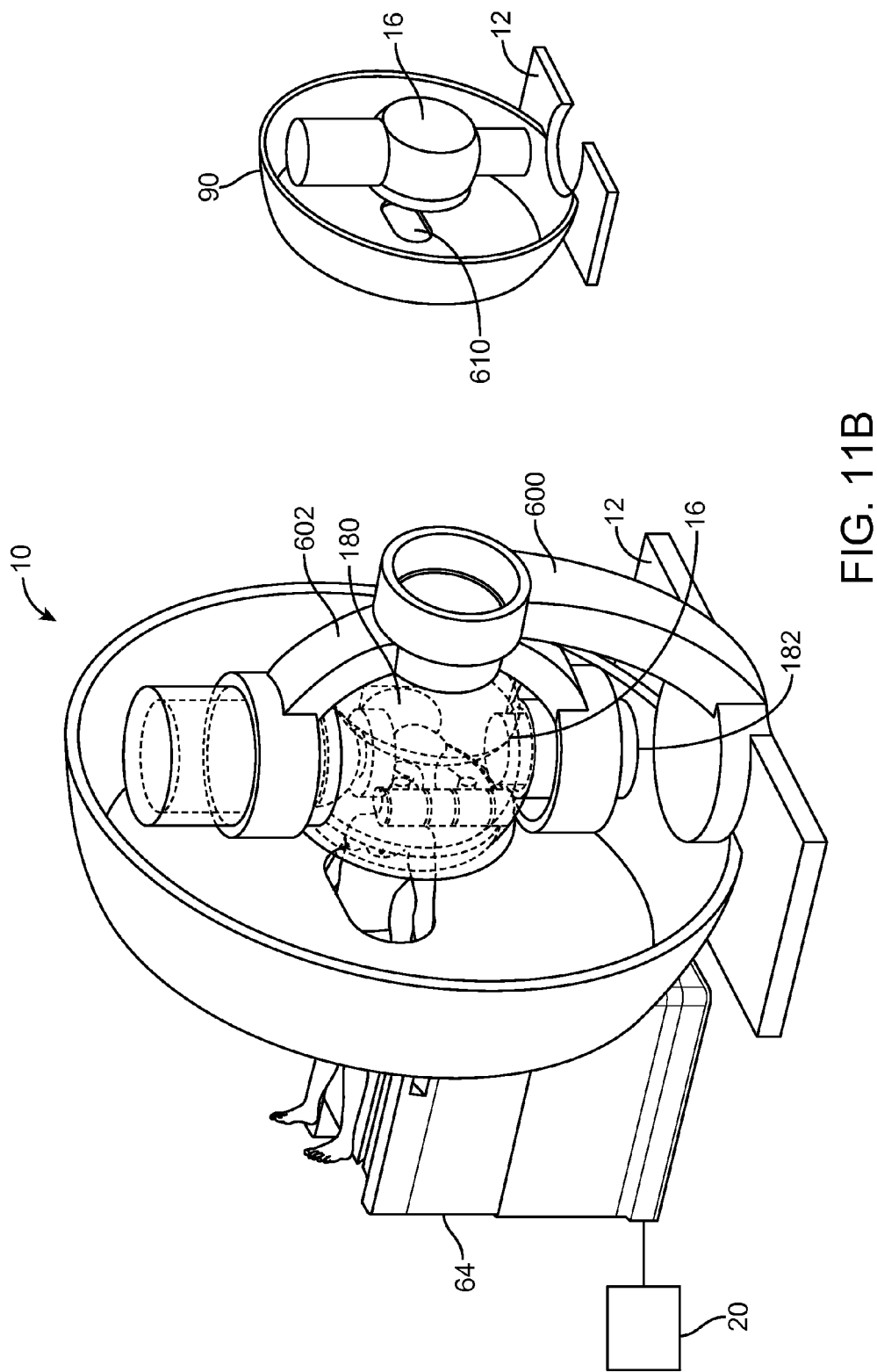

FIG. 11B illustrates the system 10 of FIG. 11A, particularly showing the system 10 having an imager 178 on one side of the capsule 16 and an imaging source 179 located on the opposite side of the capsule 16 for obtaining images before, during, and/or after a treatment session.

During a treatment session, the second support 602 may be rotated about the axis 606 relative to the first support 600 to thereby rotate the radiation source 18 around the patient 42. Also, the first support 600 may be rotated about the axis 604 relative to the support 12. This allows the radiation source 18 to be rotated about the axis 606 in different rotational planes. The different degrees of movement by the different components 600, 602 allow the radiation source 18 to be placed at different angular positions relative to the patient 42 so that radiation beam can be directed towards the patient 42 from different directions. In some embodiments, movements of the first support 600 and the second support 602 may occur simultaneously. In other embodiments, the movements of the first support 600 and the second support 602 may occur one after the other. Also, in some embodiments, the radiation source 18 may be translated along the axis 128 to place the radiation source 18 closer or further away from the patient 42. The axial movement of the radiation source 18 may occur simultaneously with a rotation of the radiation source 18, or sequentially after or before the rotation of the radiation source 18.

In the illustrated embodiments, the system 10 also includes a shield 90 disposed around the capsule 16. The shield 90 includes an opening 610 for allowing at least a part of the patient 42 to be inserted therethrough.

It should be noted that any of the shielding features described with reference to the embodiments of FIG. 1 may be optionally applied for the embodiments of FIG. 11A. For example, in some embodiments, any of the components (e.g., the capsule 16, the shield 90, or both) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement.

Also, in the illustrated embodiments of FIG. 11A, the shield 90 is configured to block at least some of the radiation that is resulted from an operation of the radiation source 18. In some embodiments, the shield 90 may be configured (e.g., have certain material density, certain geometry, and/or certain thickness), to block radiation (either alone or in combination with the capsule 16) so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90 may be configured to block off a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90 may be configured to block off (either alone or in combination with the capsule 16) a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield(s) 90 may be configured to block off all or most of the radiation resulted from an operation of the radiation source 18. In such cases, the capsule 16 may not include any shielding material.

Also, in some embodiments, the system 10 of FIG. 11A may optionally include an imager (similar to the imager 100 described with reference to FIG. 1) that cooperates with the radiation source 18 to obtain image(s).

Figure 11C:
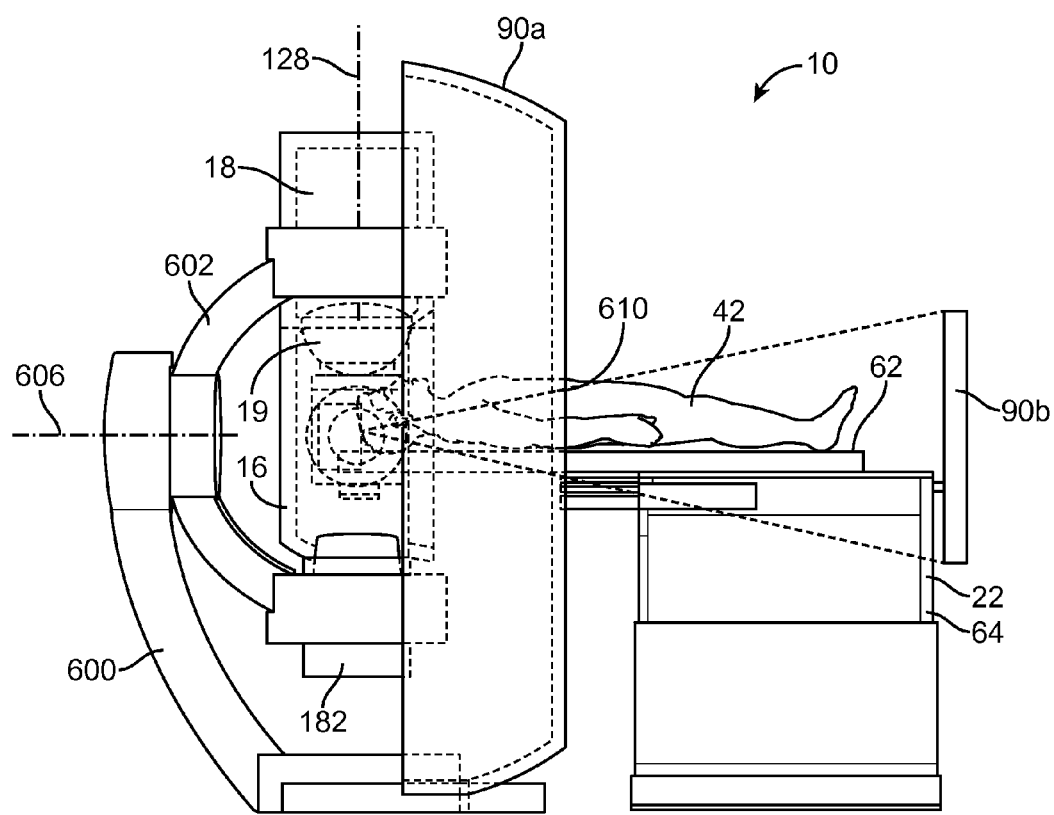

In some embodiments, the system 10 of FIG. 11A may optionally further include additional shield(s) 90. FIG. 11C illustrates a variation of the system 10 of FIG. 11A, particularly showing the system 10 having a first shield 90*a*, and a second shield 90*b*. The first shield 90*a* is similar to that shown in FIG. 11A. The second shield 90*b* is coupled to the patient support 22. The second shield 90*b* is configured to block at least some of the radiation exiting the opening 610 of the first shield 90*a*. In some embodiments, the shield 90*b* may be configured (e.g., have certain material density, certain geometry, and/or certain thickness) to block radiation so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90*b* may be configured to block off a sufficient amount of radiation (e.g., at least radiation traveling at a certain direction) resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90*b* may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield(s) 90 may be configured to block off all or most of the radiation resulted from an operation of the radiation source 18.

Figure 11D:
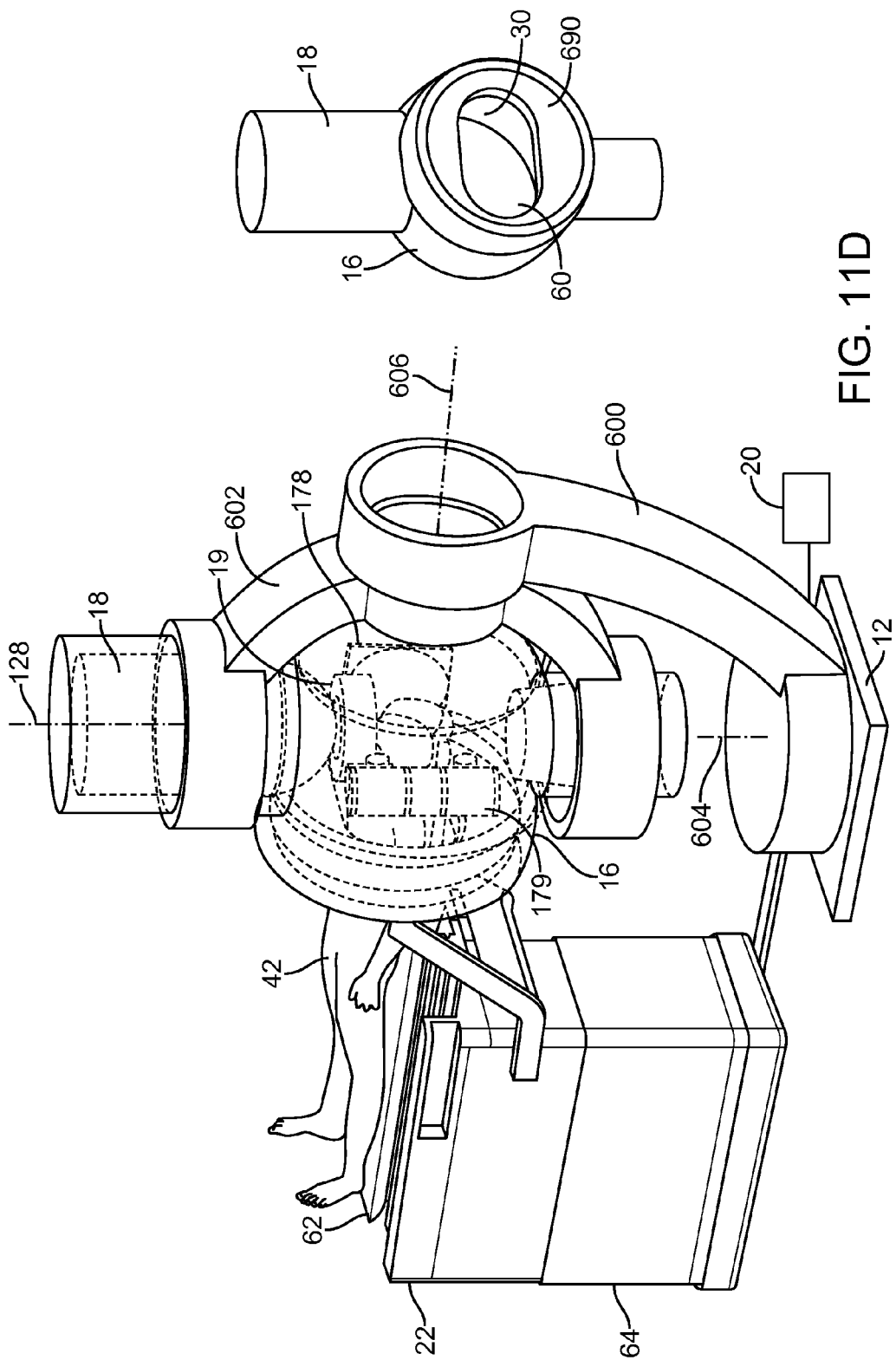

In other embodiments, the system 10 of FIG. 11A may not include the shield 90 (FIG. 11D). In such cases, the capsule 16 (including its end plate 690 that defines the opening 60) is configured to block off all or most of the radiation resulted from an operation of the radiation source 18. For example, in some embodiments, the shielding material for the capsule 16 may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material for the capsule 16 may be configured to block off a sufficient amount of radiation resulted from an operation of the radiation source 18 so that it reduces a significant amount (e.g., at least 50%, and more preferably, at least 90%) of the shielding requirement at a building.

Figure 11E:
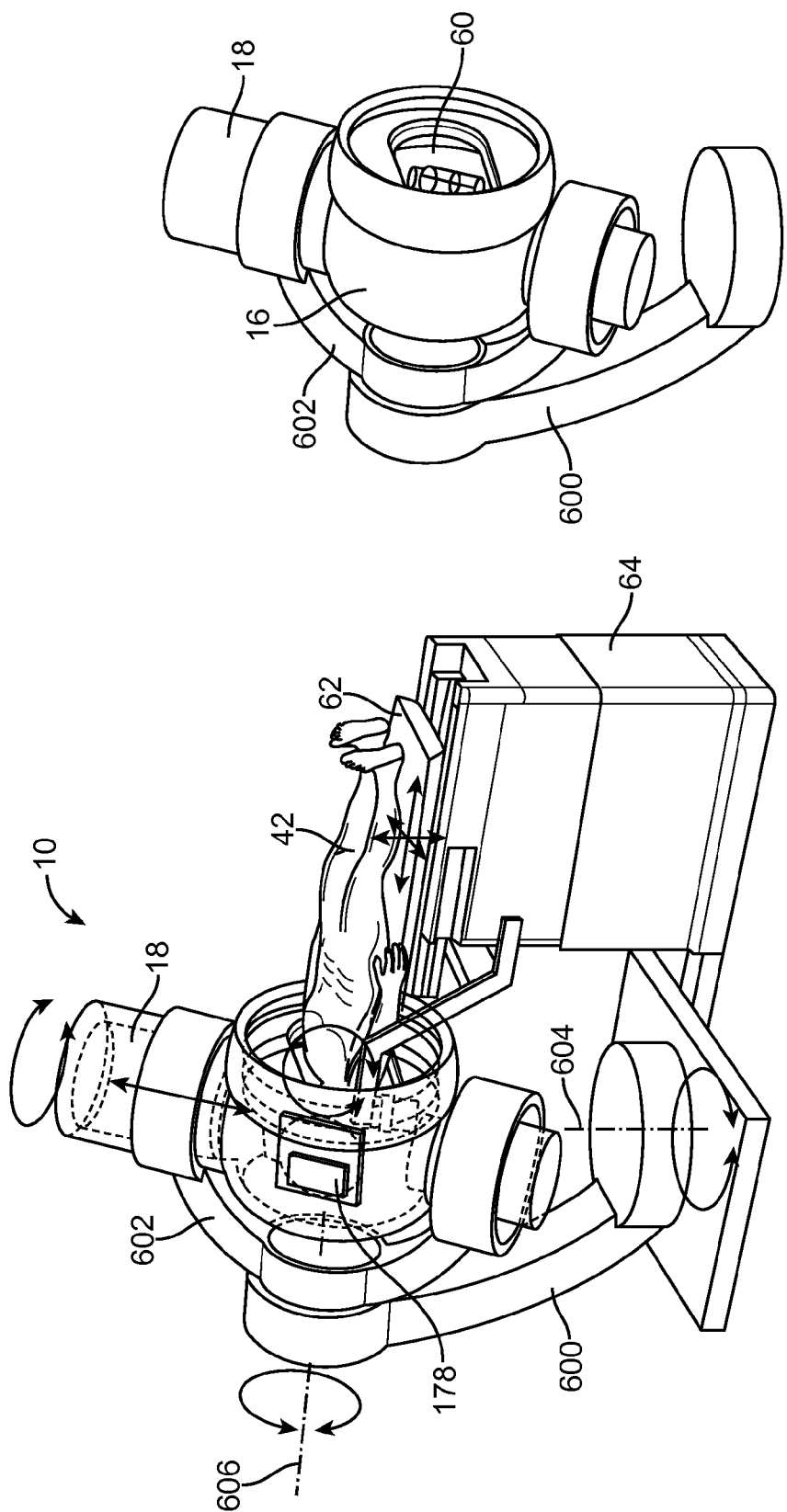

FIG. 11E illustrates different degrees of movement for different components of the system 10 of FIG. 11D.

Figure 11F:
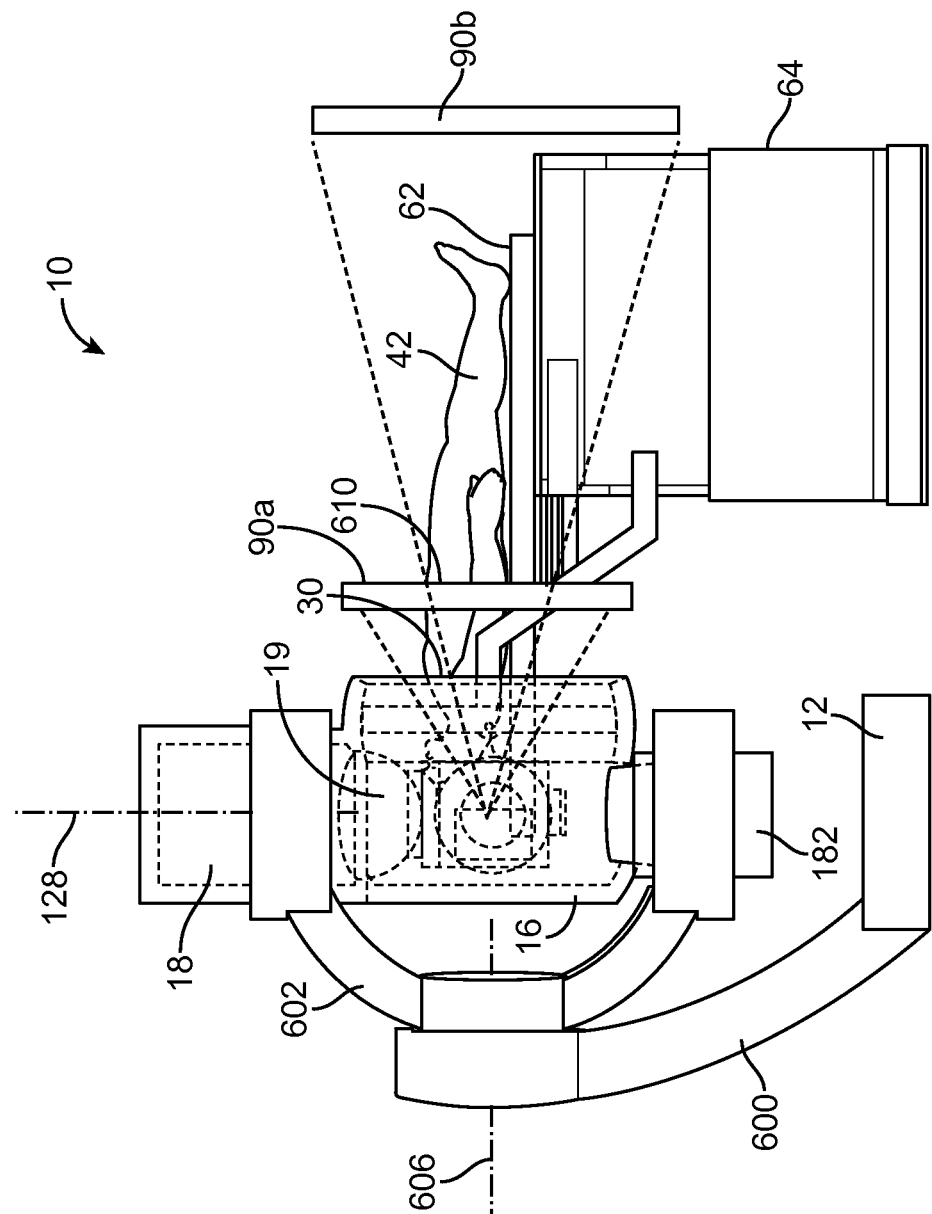

In some embodiments, the system 10 of FIG. 11D may optionally further include additional shield(s) 90. FIG. 11F illustrates a variation of the system 10 of FIG. 11D, particularly showing the system 10 having a first shield 90*a*, and a second shield 90*b*. The first shield 90*a* and the second shield 90*b* are coupled to the patient support 22. In other embodiments, the shields 90*a*, 90*b* may be coupled to other components of the system 10. The first shield 90*a* is configured to block at least some of the radiation exiting the opening 60 of the capsule 16. The second shield 90*b* is configured to block at least some of the radiation exiting the opening 610 of the first shield 90*a*. In some embodiments, the shield 90*a* and/or the shield 90*b* may be configured (e.g., have certain material density, certain geometry, and/or certain thickness) to block radiation (either by themselves or in combination with the capsule 16) so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90*a* and/or the shield 90*b* may be configured to block off (either by themselves or in combination with the capsule 16) a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90*a* and/or the shield 90*b* may be configured to block off (either by themselves or in combination with the capsule 16) a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield 90*a* and/or the shield 90*b* may be configured to block off all or most of the radiation resulted from an operation of the radiation source 18.

Figure 12A:
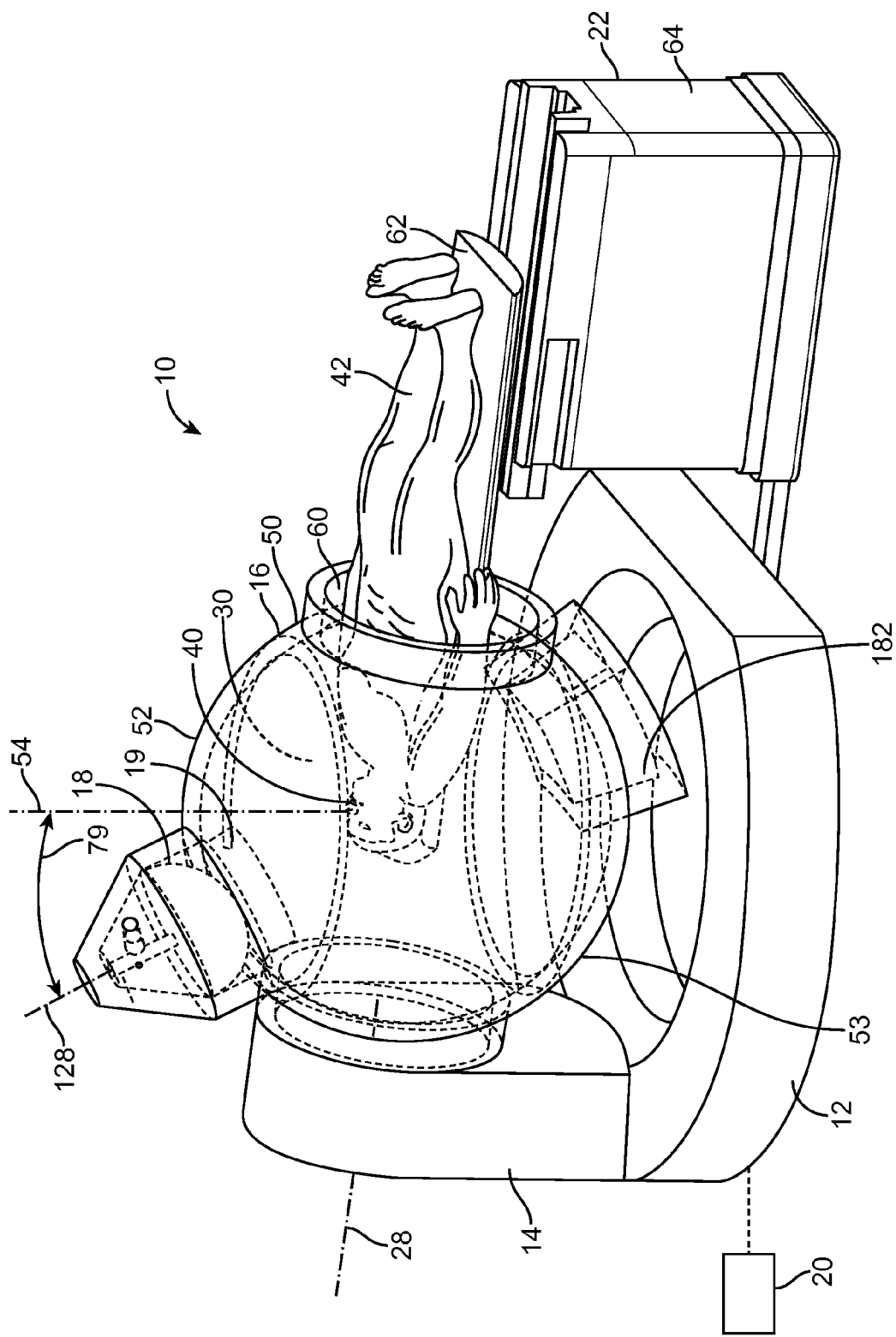

FIG. 12A illustrates another radiation system 10 in accordance with some embodiments. The radiation system 10 includes a base 12, a support 14, a capsule 16, a radiation source 18, a collimator 19, a control system 20, and a patient support 22. The system 10 is similar to that described with reference to FIG. 1, except that the capsule 16 includes a third portion 53 that rotatably couples to the portion 50. The portion 53 carries the beam stopper 182 and is configured to rotate operatively together with the portion 52. In particular, during use, as the portion 52 rotates relative to the portion 50, the portion 53 also rotates relative to the portion 50 so that the beam stopper 182 is always at the opposite side facing the radiation source (i.e., so that the beam stopper 182 is along the axis 128). As shown in the figure, the system 10 in FIG. 12A is rotatably supported only at one side of the capsule 16. However, in other embodiments, the system 10 may be rotatably supported at two opposite sides of the capsule 16. In the illustrated embodiments, the base 12 and the support 14 are manufactured as a single piece with an unity configuration. In other embodiments, the base 12 and the support 14 may be separate components that are coupled together. Also, in further embodiments, the support 14 may be moveable relative to the base 12 in one or more degrees of freedom. In still further embodiments, the base 12 may be considered to be a part of the support 14.

Figure 12B:
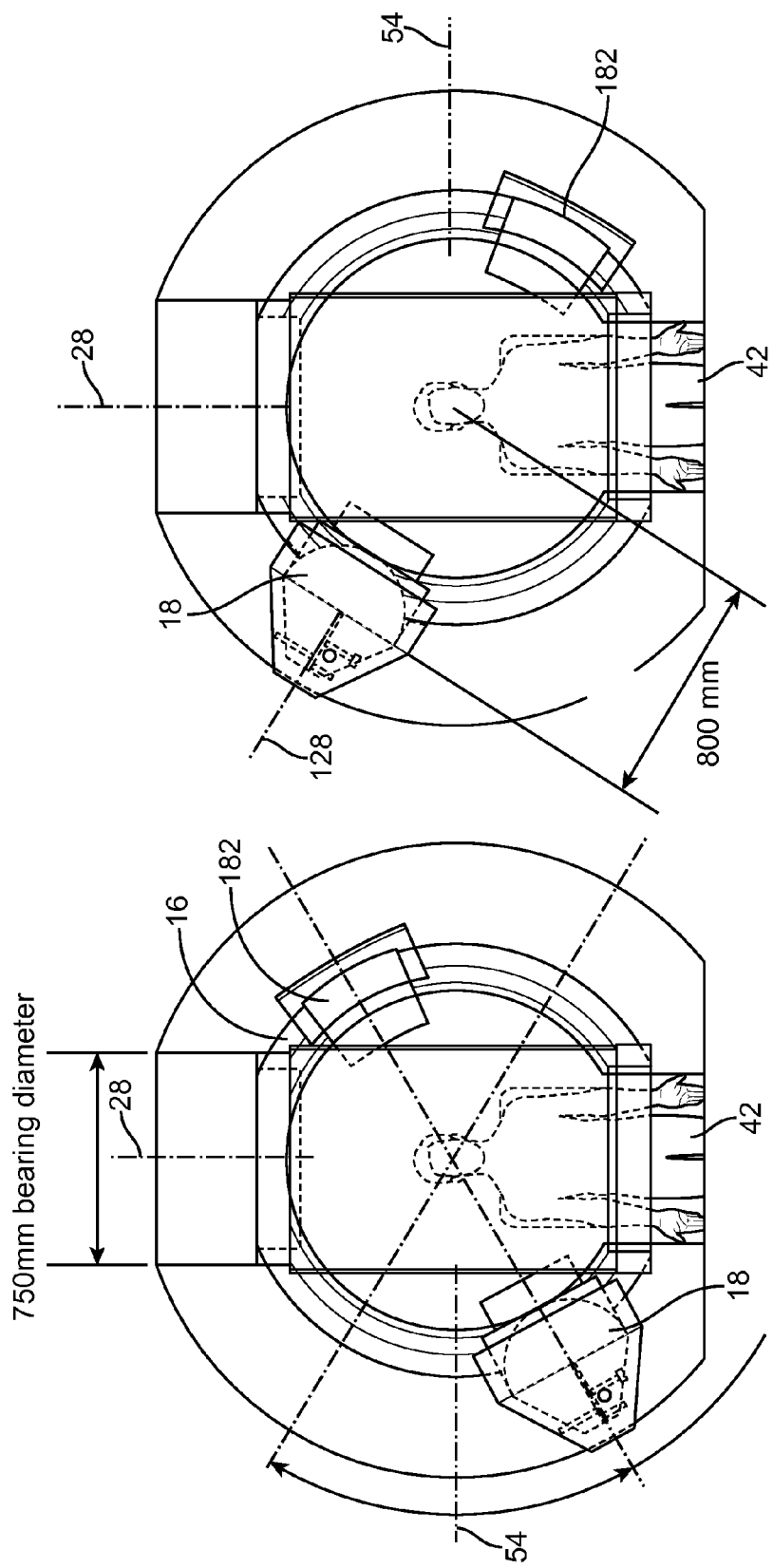

In the illustrated embodiments, the capsule 16 is rotatably coupled to the support 14 about axis 28, and defines a space 30 for accommodating at least a portion 40 of a patient 42. In the illustrated embodiments, the portion 40 includes a head and a shoulder of the patient 42. In other embodiments, the portion 40 may not include the shoulder. As shown in FIG. 12B, the rotatably coupling between the capsule 16 and the support 14 may be implemented using a large bearing, such as a bearing having a 750 mm diameter. In other embodiments, the bearing may be larger than 750 mm or less than 750 mm in diameter. Also, as shown in FIG. 12B, in some embodiments, the distance from source 18 to target may be 800 mm. In other embodiments, the distance from the source 18 to the target may be more than 800 mm or less than 800 mm. In further embodiments, the radiation source 18 may be axially translatable along the axis 128 to thereby vary the distance to target distance.

Figure 12C:
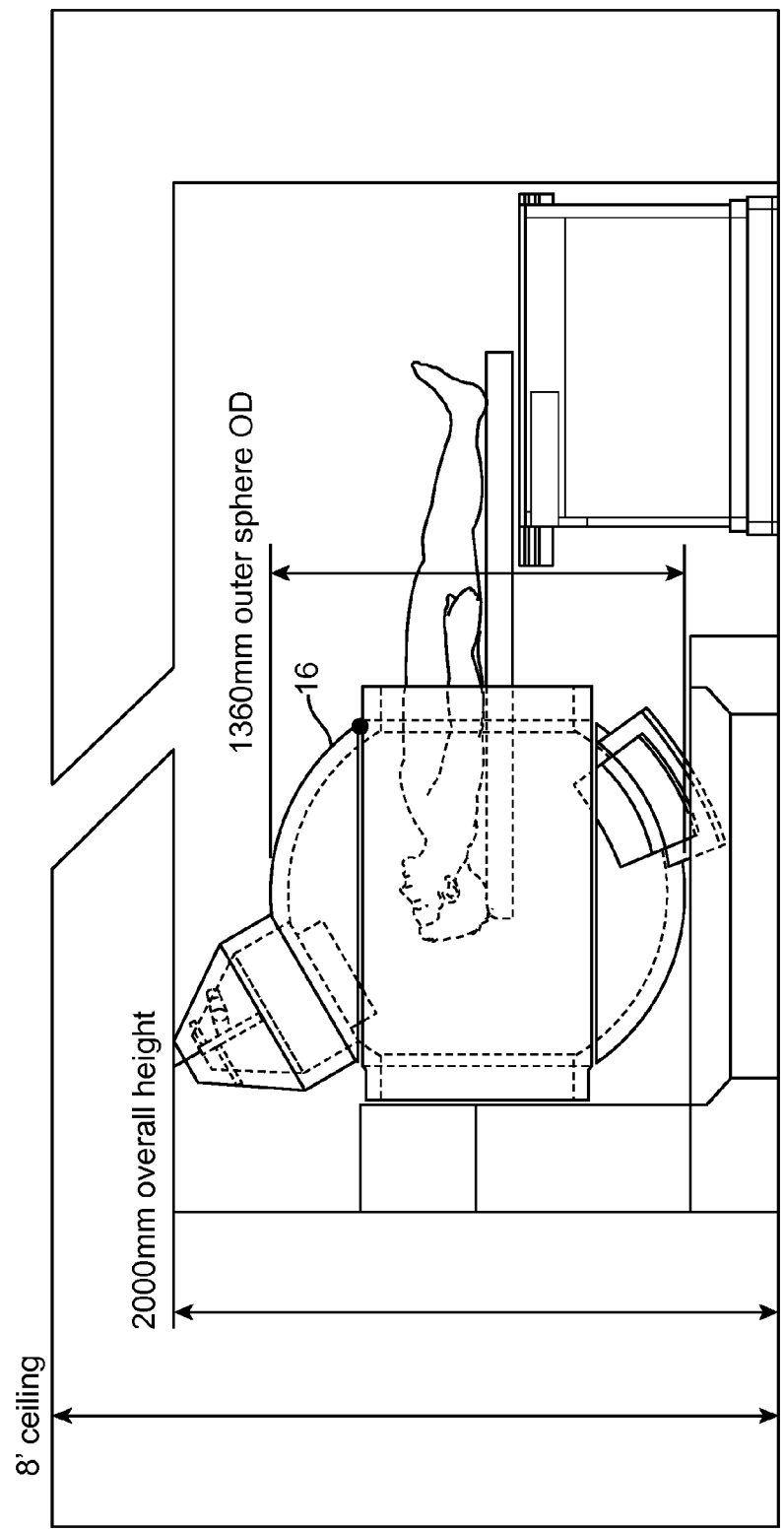

As shown in FIG. 12C, the capsule 16 may have an outer diameter of 1360 mm, and the overall height of the system 10 may be 2000 mm. In other embodiments, the capsule 16 may have an outer diameter that is more than 1360 mm or less than 1360 mm. Also, in other embodiments, the system 10 may have a height that is more than 2000 mm or less than 2000 mm.

Returning to FIG. 12A, the capsule 16 includes a first capsule portion 50 and a second capsule portion 52 that is rotatable relative to the first capsule portion 50 about axis 54. In one implementation, the first capsule portion 50 and the second capsule portion 52 may be rotatably coupled to each other using a tongue-and-groove mechanism, which may be more effective in preventing leakage of radiation between the coupling of the portions 50, 52 (because part of the tongue-and-groove mechanism may attenuate some of the radiation). In other embodiments, the first and second capsule portions 50, 52 may be coupled using other mechanisms. In the illustrated embodiments, the first and second capsule portions 50, 52 define an interior surface that has a partial spherical configuration. In other embodiments, the interior surface may have other configurations, and is not limited to a spherical configuration. Also, in some embodiments, the second capsule portion 52 may be a part of the radiation source 18.

As shown in FIG. 12A, the radiation source 18 is tilted so that it (e.g., the axis 128 of the radiation source 18) forms an angle 79 (e.g., a non-zero acute angle) relative to the axis 54. Such configuration allows the radiation source 18 to deliver radiation from different angles towards the portion 40 of the patient 42 as the second portion 52 rotates relative to the first portion 50 about the axis 54. In other embodiments, the capsule 16 may be rotated about the axis 28 to turn the radiation source 18 around the patient so that radiation may be delivered to the patient from different angles. In some embodiments, the rotation of the portion 52 about the axis 54, and the rotation of the capsule portion 50 about the axis 28, may be performed one after the other. Alternatively, the rotation of the second portion 52 about the axis 54, and the rotation of the first portion 50 about the axis 28, may be performed simultaneously. In some embodiments, the radiation source 18 may be configured to be tiltable relative to the second portion 52.

As shown in FIG. 12A, the capsule 16 also includes an opening 60 for allowing the portion 40 of the patient 42 to go therethrough in order to reach the interior space 30 of the capsule 16. The patient support 22 includes a table 62 for supporting the patient 42, and a positioner 64 configured to translate the table 62 axially so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

It should be noted that the operation of the system 10 of FIG. 12A is similar to that described with reference to the embodiments of FIG. 1.

It should be noted that any of the shielding features described with reference to the embodiments of FIG. 1 may be optionally applied for the embodiments of FIG. 12A. For example, in some embodiments, any of the components (e.g., the capsule 16) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement. Also, in some embodiments, the radiation system 10 may optionally further include one or more shields (e.g., the shield(s) 90 described with reference to FIG. 1) for blocking radiation that is resulted from an operation of the radiation source 18. The shield(s) may be coupled to any of the components in the system 10.

Figure 12D:
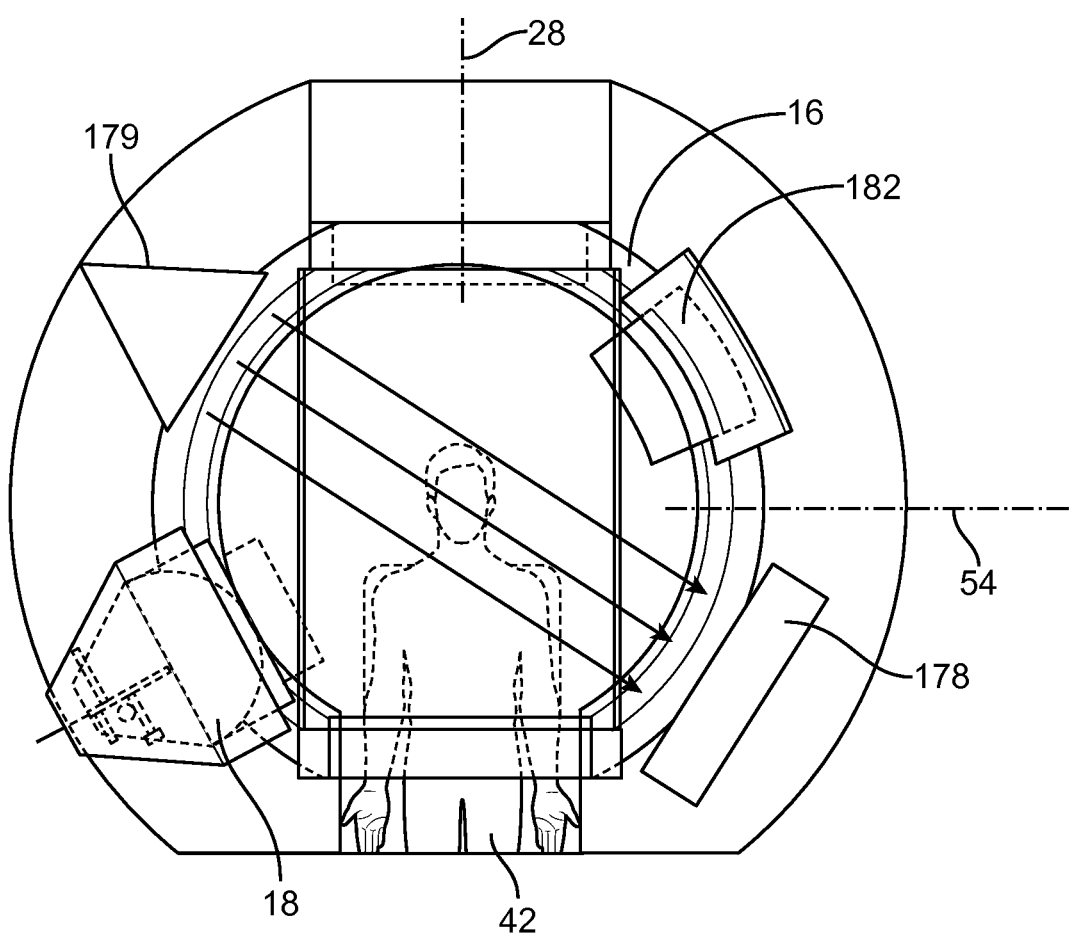

Also, in some embodiments, the system 10 may optionally include an imager (similar to the imager 100 described with reference to FIG. 1) that cooperates with the radiation source 18 to obtain image(s). Furthermore, in some embodiments in which the radiation source 18 is a treatment radiation source, the system 10 may optionally further include an imager 178 on one side of the capsule 16 and an imaging source 179 located on the opposite side of the capsule 16 for obtaining images before, during, and/or after a treatment session (FIG. 12D).

In other embodiments, the axis 54 of rotation may be non-perpendicular to the axis 28 of rotation (FIG. 12E). FIG. 12F shows the embodiments of FIG. 12E, particularly showing the capsule portion 52 having been rotated about the axis 54 so that the radiation source 18 is aiming upward (as opposed to the initial position in FIG. 12E in which the radiation source 18 is aiming downward from the top of the patient's head).

Figure 12G:
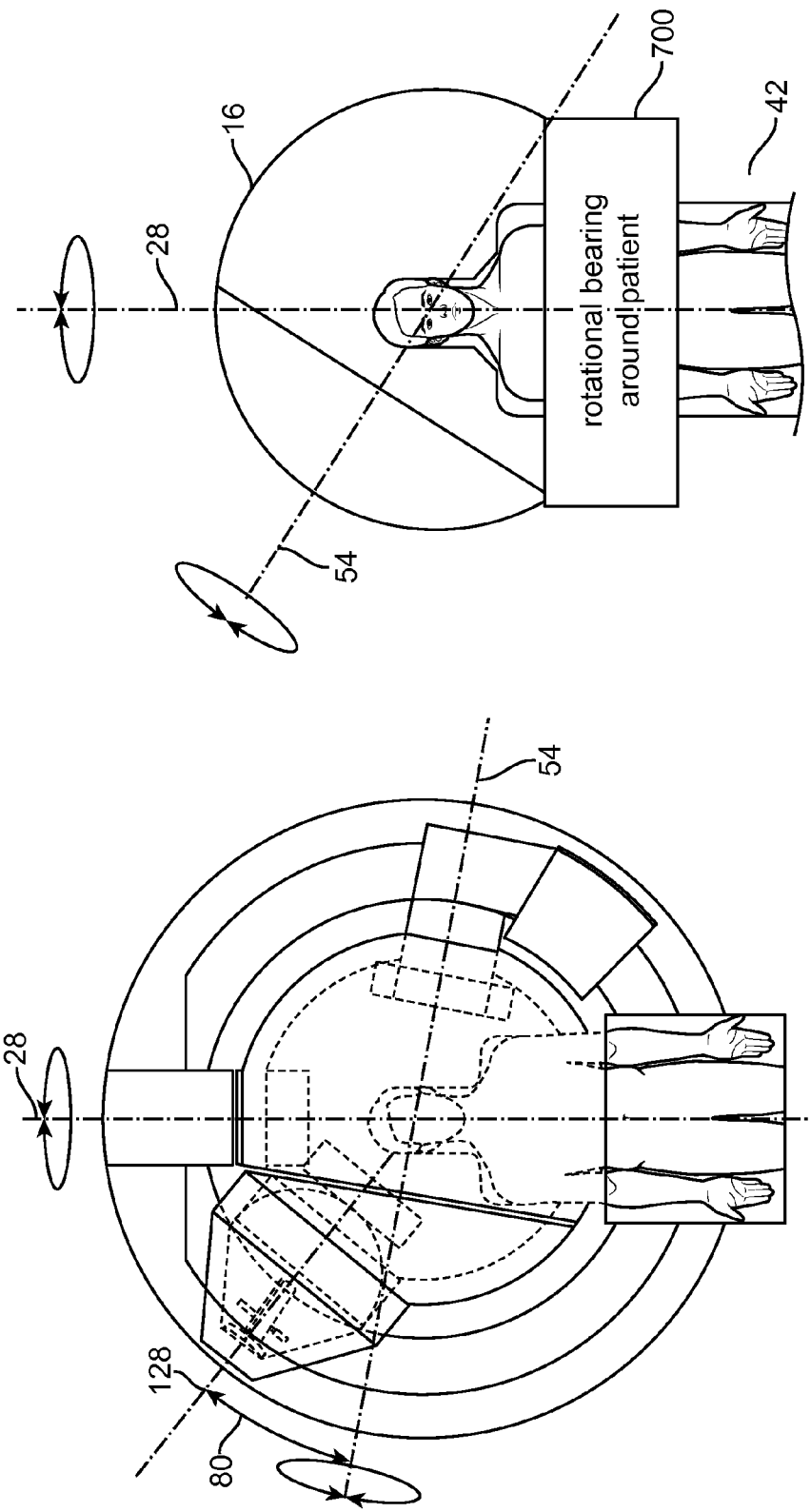

In the above embodiments the bearing for rotatably coupling the capsule 16 to the support 14 is located above the patient's head. In other embodiments, the bearing for rotatably coupling the capsule 16 to the support 14 may be located at other positions. For example, in other embodiments, the system 10 may include a bearing 700 located at the opposite side of the capsule 16 for rotatably coupling to the capsule 16 (FIG. 12G). For example, in some embodiments, the bearing 700 may be located next to the opening 60, or may itself define the opening 60 for accommodating at least a part of the patient 42.

Figure 13A:
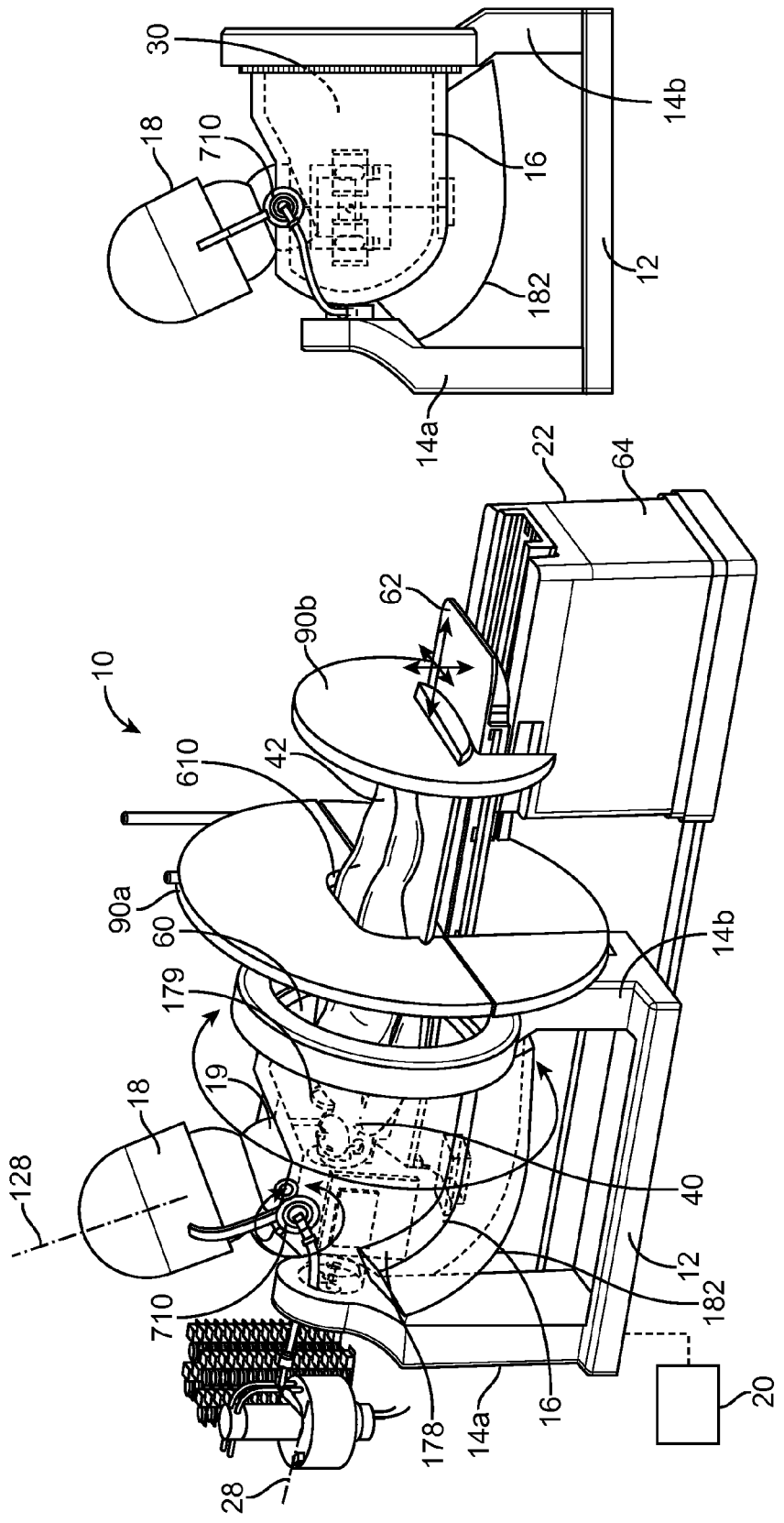
FIGS. 13A-13D illustrate another radiation system in accordance with other embodiments.
Figure 13B:
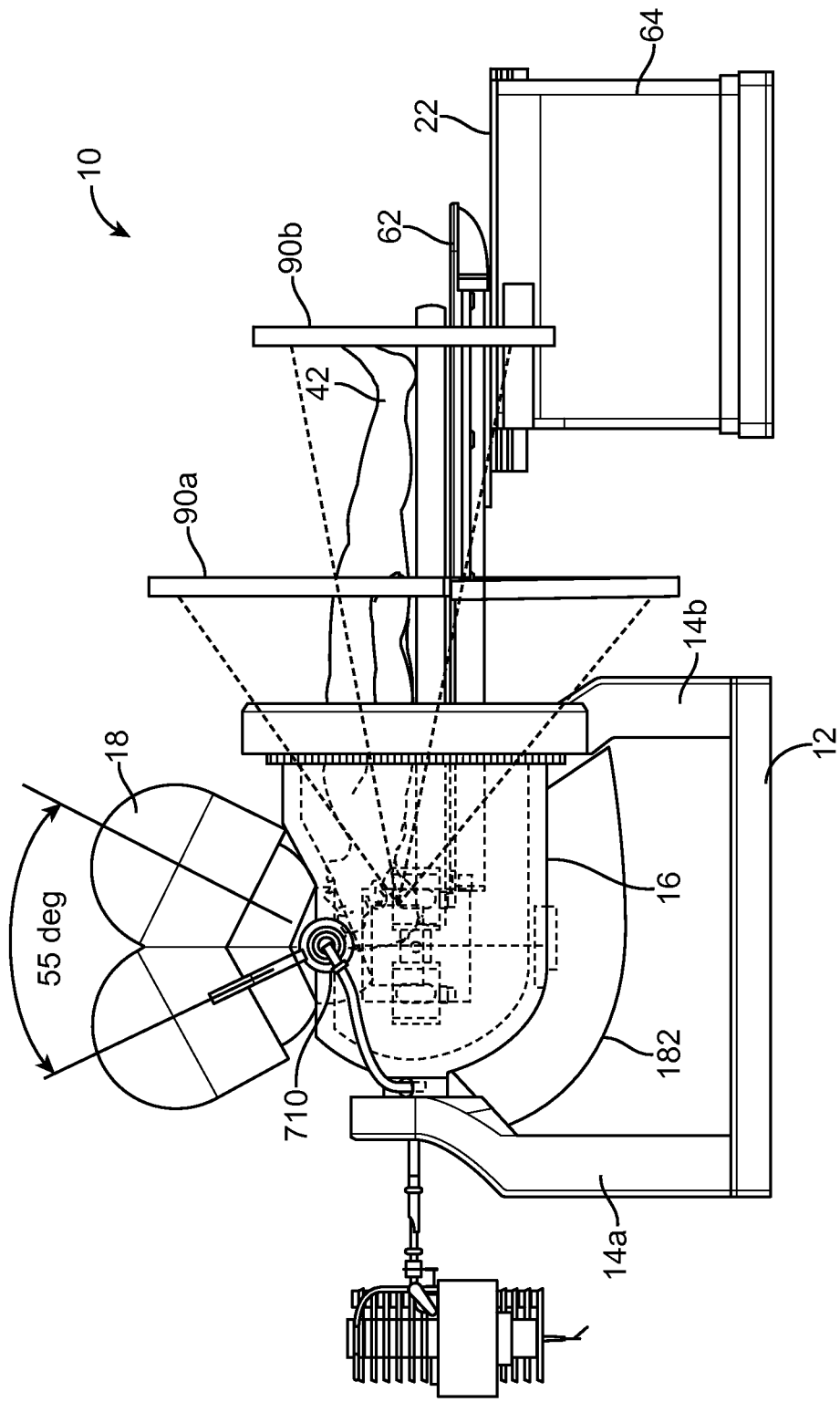

FIG. 13A illustrates another radiation system 10 in accordance with some embodiments. The radiation system 10 includes a base 12, a first support 14a, a second support 14b, a capsule 16, a radiation source 18, a collimator 19, a control system 20, and a patient support 22. The system 10 is similar as that described with reference to FIG. 7, except that the capsule 16 does not have a second portion 52 that rotates about the axis 54 relative to a first portion 50. Instead, the radiation source 18 is rotatably coupled to the capsule 16 via a hinge 710 so that the radiation source 18 can be rocked back-and-forth relative to the capsule 16. As shown in FIG. 13B, the radiation source 18 may tilt through an angular range of 55 degrees. In other embodiments, the angular range of tilting may be more than 55 degrees or less than 55 degrees. Returning to FIG. 13A, in the illustrated embodiments, the base 12 and the supports 14a, 14b are manufactured as a single piece with an unity configuration. In other embodiments, the base 12 and the supports 14a, 14b may be separate components that are coupled together. Also, in further embodiments, the supports 14a, 14b may be moveable relative to the base 12 in one or more degrees of freedom. In still further embodiments, the supports 14a, 14b may be considered to be parts of the base 12.

As shown in the figure, the radiation system 10 also includes a back stop 182 in operative position with respect to the radiation source 18. The back stop 182 may be fixedly coupled to the capsule 16 or to other components of the system 10. The back stop 182 is configured to block radiation that is in the radiation path of the radiation source 18. In the illustrated embodiments, the back stop 182 has a dimension that corresponds with the angular range of movement by the radiation source 18. In particular, the back stop 182 has an elongated shape so that regardless of the angle in which the radiation source 18 is tilted relative to the capsule 16, the back stop 182 will be able to block the radiation that is in the radiation path of the radiation source 18. In other embodiments, instead of being fixedly coupled to the capsule 16, the back stop 182 may be configured to move in synchronization with the tilting of the radiation source 18, so that when the tilting angle of the radiation source 18 changes, the back stop 182 will be moved accordingly to be in the radiation path of the radiation source 18.

In the illustrated embodiments, the capsule 16 is rotatably coupled to the support 14 about axis 28, and defines a space 30 for accommodating at least a portion 40 of a patient 42. In the illustrated embodiments, the portion 40 includes a head and a shoulder of the patient 42. In other embodiments, the portion 40 may include only the head of the patient 42.

During use, the radiation source 18 may be tilted so that it can deliver radiation towards the patient 42 from different angles. Also, the capsule 16 may be rotated about the axis 28 to turn the radiation source 18 around the patient so that radiation may be delivered to the patient from different angles. In some embodiments, the rotation of the capsule 16 about the axis 28, and the tilting of the radiation source 18 about the hinge 710, may be performed one after the other. Alternatively, the rotation of the capsule 16 about the axis 28, and the tilting of the radiation source 18, may be performed simultaneously. In some embodiments, the radiation source 18 may also be configured to be translated along the longitudinal axis 128 of the radiation source 18 to thereby change the source-to-target distance.

As shown in FIG. 13A, the capsule 16 also includes an opening 60 for allowing the portion 40 of the patient 42 to go therethrough in order to reach the interior space 30 of the capsule 16. The patient support 22 includes a table 62 for supporting the patient 42, and a positioner 64 configured to translate the table 62 axially so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

Figure 13D:
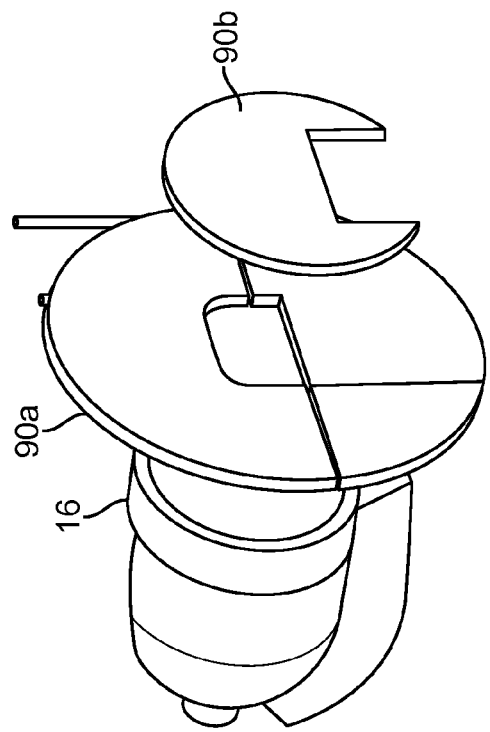
Figure 13C:
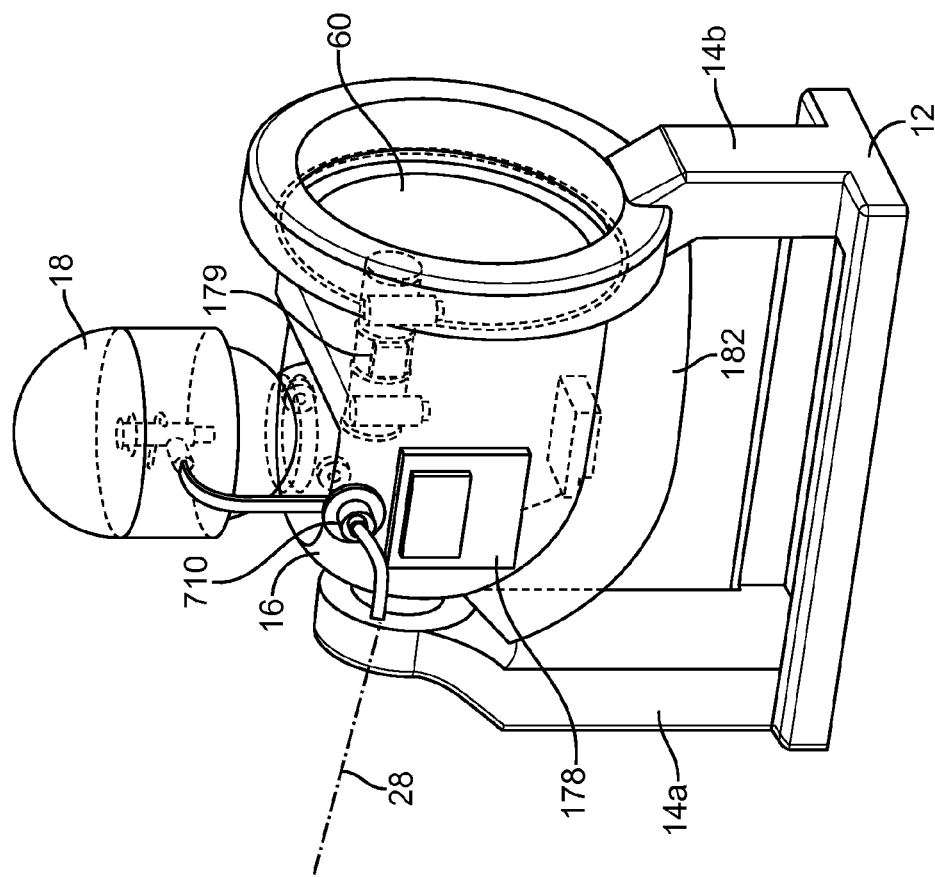

As shown in the figure, in some embodiments, the system 10 may optionally further include an imager 178 on one side of the capsule 16 and an imaging source 179 located on the opposite side of the capsule 16 for obtaining images before, during, and/or after a treatment session (FIGS. 13A, 13C).

Also, in some embodiments, the system 10 may optionally include an imager (similar to the imager 100 described with reference to FIG. 1) that cooperates with the radiation source 18 to obtain image(s).

It should be noted that any of the shielding features described with reference to the embodiments of FIG. 1 may be optionally applied for the embodiments of FIG. 13A. For example, in some embodiments, any of the components (e.g., the capsule 16) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement. Also, in some embodiments, the radiation system 10 may optionally further include one or more shields (e.g., the shield(s) 90 described with reference to FIG. 1) for blocking radiation that is resulted from an operation of the radiation source 18. The shield(s) may be coupled to any of the components in the system 10.

In the illustrated embodiments of FIG. 13A, the system 10 further includes a first shield 90a, and a second shield 90b, configured to block at least some of the radiation that is resulted from an operation of the radiation source 18. In particular, the first shield 90a is configured to block at least some of the radiation exiting from the opening 60 of the capsule 16, and the second shield 90b is configured to block at least some of the radiation exiting from the opening 610 of the first shield 90a (FIG. 13B). In some embodiments, the shields 90a and/or the shield 90b may be configured (e.g., have certain material density, certain geometry, and/or certain thickness) to block radiation (either by themselves or in combination with the capsule 16) so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90a and/or the shield 90b may be configured to block off (by themselves or in combination with the capsule 16) a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90a and/or the shield 90b may be configured to block off (either by themselves or in combination with the capsule 16) a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield 90a and/or the shield 90b may be configured to block off all or most of the radiation resulted from an operation of the radiation source 18 (at least at a certain direction). In such cases, the capsule 16 may not include any shielding material.

Although two shields 90a, 90b are shown, in other embodiments, the system 10 may include more than two shields 90 or fewer than two shields 90 (e.g., one shield or no shield).

In some embodiments, the shielding provided by the capsule 16 and shields 90a, 90b has a total weight that is 3200 kg (FIG. 13D). In other embodiments, the total weight of the shielding may be more than 3200 kg, or less than 3200 kg.

Figure 14A:
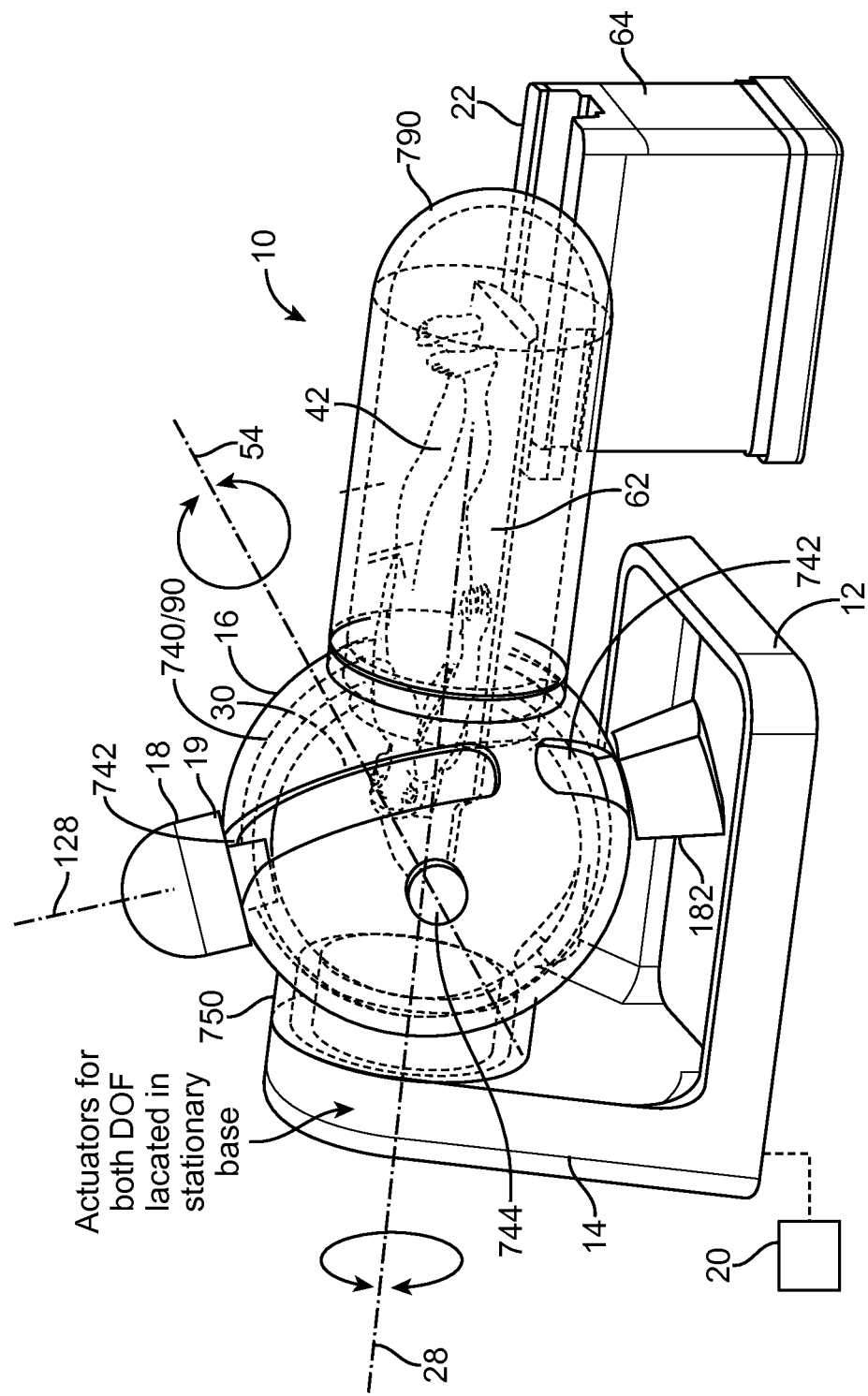
FIGS. 14A-14D illustrate another radiation system in accordance with other embodiments.

FIG. 14A illustrates another radiation system 10 in accordance with some embodiments. The radiation system 10 includes a base 12, a support 14, a capsule 16, a radiation source 18, a collimator 19, a control system 20, and a patient support 22. The system 10 also includes an inner support 740 that is rotatable within the capsule 16. The inner support 740 is coupled to, and carries, the radiation source 18 and the collimator 19, so that movement of the inner support 740 will cause the radiation source 18 and the collimator 19 to move together. The capsule 16 includes one or more slots 742 for accommodating motion of the radiation source 18 and the back stop 182 (or for accommodating structural components that couple the source 18 and the back stop 182 to the inner support 740). In some embodiments, the inner support 740 may have a spherical configuration. In other embodiments, the inner support 740 may have a partial spherical configuration. In further embodiments, the inner support 740 may have a C-shape or an arch shape. In some embodiments, the inner support 740 is concentrically disposed relative to the capsule 16, and defines a space for accommodating at least a part of the patient 42. In the illustrated embodiments, the inner support 742 is rotatably coupled to the capsule 16 via a hinge 744 (or a pair of hinges), which may include a bearing in some embodiments. Also, the capsule 16 is rotatably coupled to the support 14 via a bearing 750.

In some embodiments, the bearing 750 may have a diameter of 800 mm. In other embodiments, the bearing 750 may have a diameter that is more than 800 mm or less than 800 mm. Also, in some embodiments, the capsule 16 may have an outer diameter of 1300 mm. In other embodiments, the capsule 16 may have an outer diameter that is larger than 1300 mm or less than 1300 mm. Furthermore, in some embodiments, the system 10 may have an overall height of 2000 mm. In other embodiments, the system 10 may have an overall height that is larger than 2000 mm or less than 2000 mm.

In the illustrated embodiments, the base 12 and the support 14 are manufactured as a single piece with an unity configuration. In other embodiments, the base 12 and the support 14 may be separate components that are coupled together. Also, in further embodiments, the supports 14a, 14b may be moveable relative to the base 12 in one or more degrees of freedom. In still further embodiments, the support 14 may be considered to be a part of the base 12.

As shown in the figure, the radiation system 10 also includes a back stop 182 in operative position with respect to the radiation source 18. The back stop 182 may be fixedly coupled to the inner support 740 so that movement of the inner support 740 will cause the radiation source 18 and the back stop 182 to move together. The back stop 182 is configured to block radiation that is in the radiation path of the radiation source 18.

In the illustrated embodiments, the capsule 16 is rotatably coupled to the support 14 about axis 28, and defines a space 30 for accommodating at least a portion 40 of a patient 42. In the illustrated embodiments, the portion 40 includes a head and a shoulder of the patient 42. In other embodiments, the portion 40 may include only the head of the patient 42.

During use, the radiation source 18 may be rotated about the axis 28 by turning the capsule 16 about the axis 28 relative to the support 14, so that the radiation source 18 can deliver radiation towards the patient 42 from different angles. Also, the inner support 740 may be rotated about the axis 54 to turn the radiation source 18 around the patient so that radiation may be delivered to the patient from different angles. In some embodiments, the rotation of the capsule 16 about the axis 28, and the rotation of the inner support 742 relative to the capsule 16, may be performed one after the other. Alternatively, the rotation of the capsule 16 about the axis 28, and the rotation of the inner support 742, may be performed simultaneously. Also, in some embodiments, movement of the capsule 16 and the inner support 740 may be caused by respective actuators that reside in the housing of the support 14. In some embodiments, the radiation source 18 may also be configured to be translated along the longitudinal axis 128 of the radiation source 18 to thereby change the source-to-target distance.

Figure 14B:
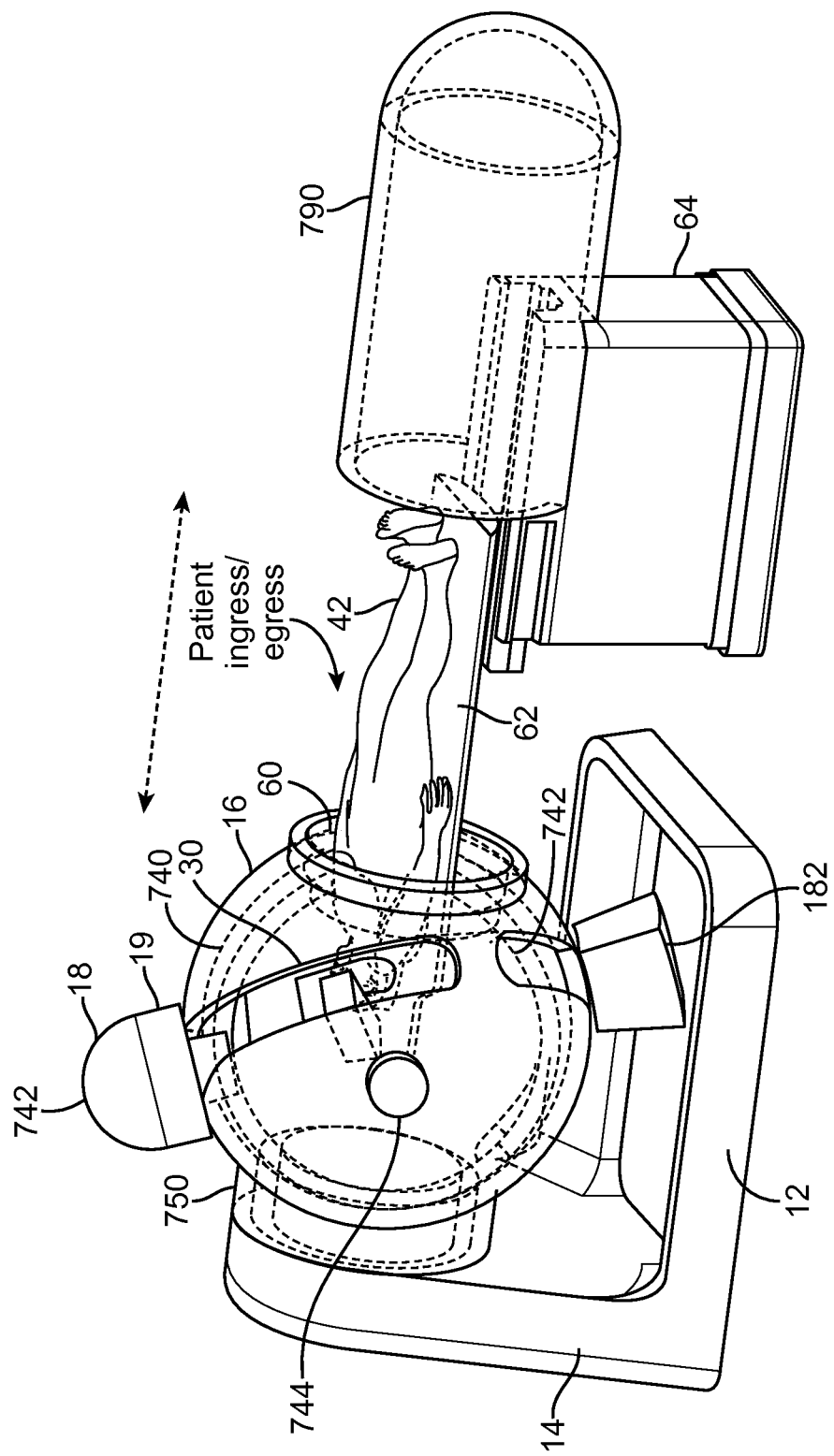

As shown in FIG. 14B, the capsule 16 also includes an opening 60 for allowing the portion 40 of the patient 42 to go therethrough in order to reach the interior space 30 of the capsule 16. The patient support 22 includes a table 62 for supporting the patient 42, and a positioner 64 configured to translate the table 62 axially so that the portion 40 of the patient 42 may be placed through the opening 60 to reach the space 30. In other embodiments, the positioner 64 may provide other movement(s) for the table 62. For example, in other embodiments, the positioner 64 may move the table 62 vertically up and down to allow the patient 42 to get up to the table 62 and/or to align the portion 40 with the opening 60 at the capsule 16. Additionally, or alternatively, a horizontal translation may be used to position the treatment volume at a desired location relative to the axes of rotation. In further embodiments, the positioner 64 may rotate the table 62 about a vertical axis to thereby place the patient 42 at different angular positions relative to the capsule 16. In the illustrated embodiments, the patient support 22 is coupled to the base 12 through the positioner 64. Such configuration allows the support 22 and the capsule 16 to be transported as a single unit. In other embodiments, the patient support 22 may be separated from the base 12. For example, in other embodiments, the patient support 22 may be transportable independently from the base 12.

Figure 14C:
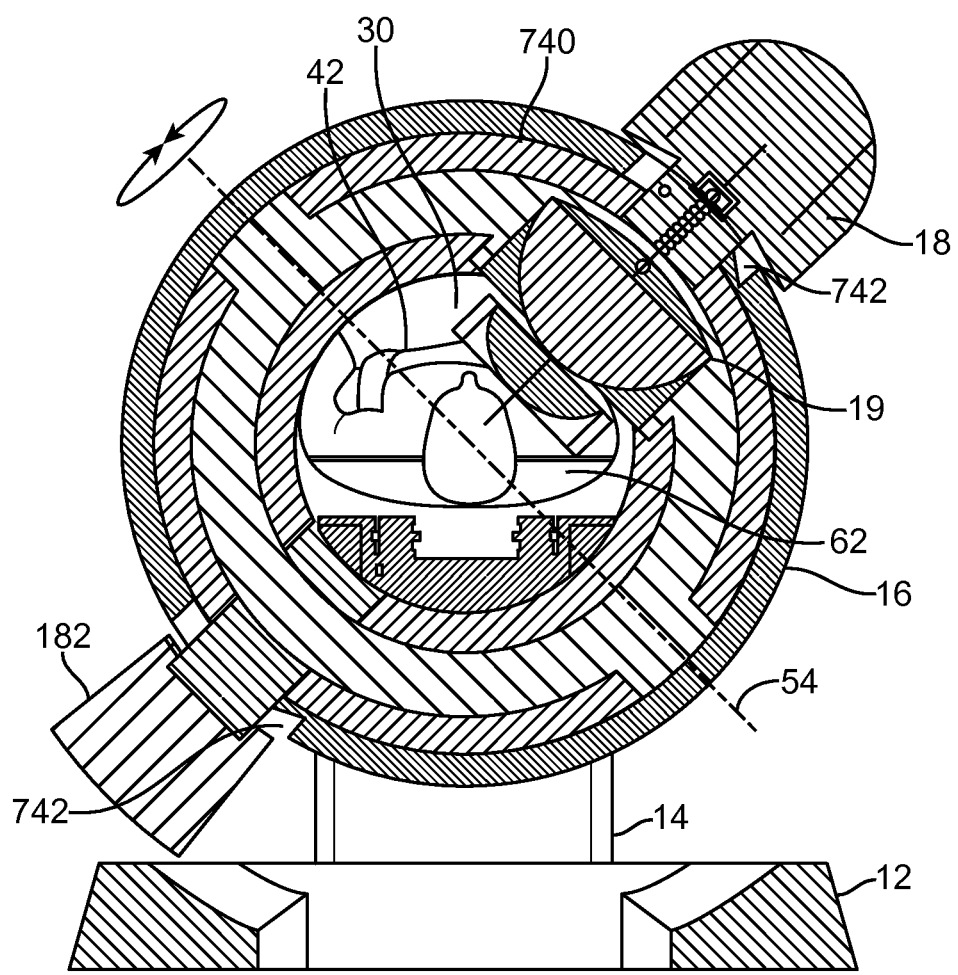

FIG. 14C is a cross sectional end view of the system 10 of FIG. 14A, showing various components of the system 10.

Figure 14D:
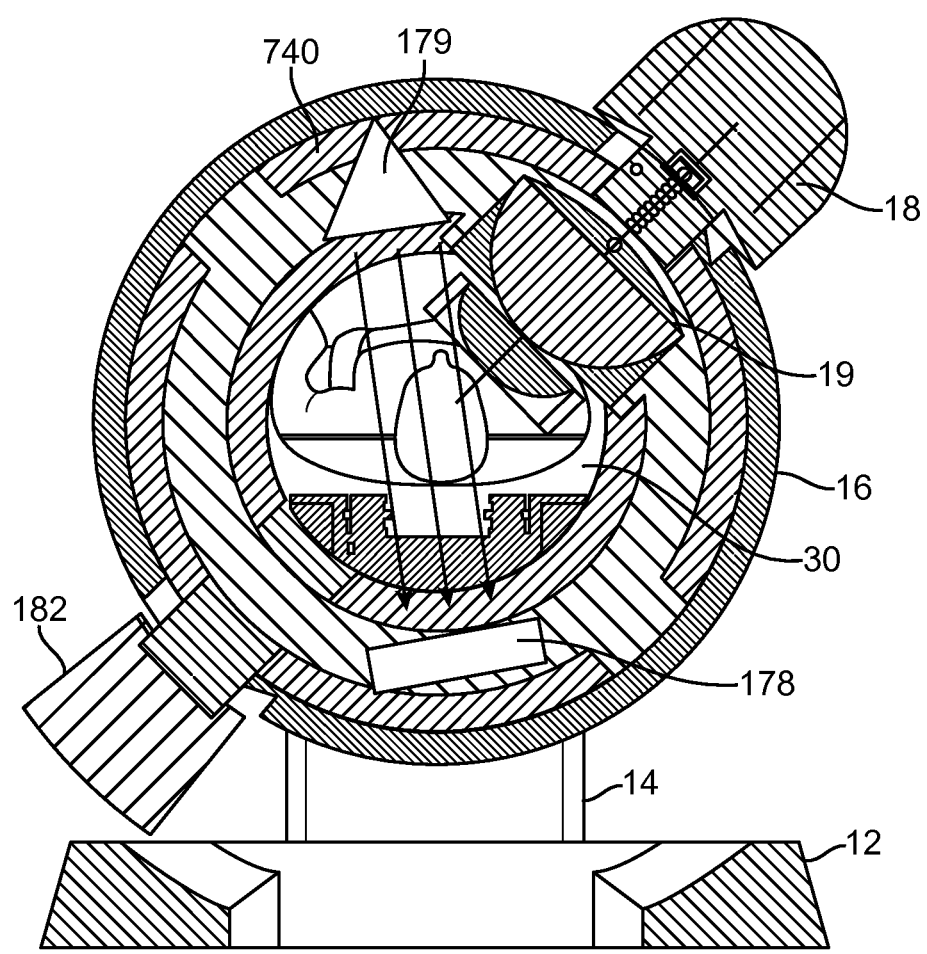

As shown in the figure, in some embodiments, the system 10 may optionally further include an imager 178 on one side of the capsule 16 and an imaging source 179 located on the opposite side of the capsule 16 for obtaining images before, during, and/or after a treatment session (FIG. 14D).

Also, in some embodiments, the system 10 may optionally include an imager (similar to the imager 100 described with reference to FIG. 1) that cooperates with the radiation source 18 to obtain image(s).

It should be noted that any of the shielding features described with reference to the embodiments of FIG. 1 may be optionally applied for the embodiments of FIG. 14A. For example, in some embodiments, any of the components (e.g., the capsule 16) surrounding at least a part of the patient 42 may include a shielding material that is configured to block at least some of the radiation that is resulted from an operation of the radiation source 18. The shielding material may include any material(s) that is known for providing radiation shielding, including but not limited to steel, lead, tungsten, or combination thereof. Also, in some embodiments, the shielding material may be configured (e.g., have certain material density, certain geometry, and/or certain thickness) to block radiation so that it reduces (attenuates) at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shielding material may be configured to block off a sufficient amount of radiation resulted from an operation of the radiation source 18 so that it obviates the need to provide additional shielding for non-occupational exposure at a treatment facility, such as a hospital or office. Such feature is advantageous because it allows the radiation system 10 to be useable at any location within the building (provided that the weight of the system 10 does not exceed the load-bearing capability of the building), or at any facility, without requiring expensive retrofit to be done to the building to provide shielding against ionizing radiation such as alpha, beta, gamma or neutron. In other embodiments, instead of completely eliminating shielding at a building, the shielding material may be configured to block off a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. For example, the shielding requirement for the entire room may be reduced, or only portion(s) of the room may need to be retrofitted for shielding requirement. Also, in some embodiments, the radiation system 10 may optionally further include one or more shields (e.g., the shield(s) 90 described with reference to FIG. 1) for blocking radiation that is resulted from an operation of the radiation source 18. The shield(s) may be coupled to any of the components in the system 10.

In some embodiments, in the system 10 of FIG. 14A, the inner support 740 may form a shield 90, which is configured to block at least some of the radiation that is resulted from an operation of the radiation source 18. In some embodiments, the shield 90 may be configured (e.g., have certain material density, certain geometry, and/or certain thickness) to block radiation (either alone or in combination with the capsule 16) so that it reduces at least 98%, and more preferably at least 99.9%, and even more preferably at least 99.999%, of the radiation (e.g., photons/charged particles, such as electrons, neutrons, etc.) resulted from an operation of the radiation source 18 traveling therethrough. In further embodiments, the shield 90 may be configured to block off (either alone or in combination with the capsule 16) a sufficient amount of radiation resulted from an operation of the radiation source 18 so that it obviates the need to provide shielding at a facility building, such as at a hospital. Such feature is advantageous because it allows the radiation system 10 to be useable at any location within the building, or at any facility, without requiring expensive retrofit to be done to the building to provide radiation shielding. In other embodiments, instead of completely eliminating shielding at a building, the shield 90 may be configured to block off (either alone or in combination with the capsule 16) a sufficient amount of radiation resulted from an operation of the radiation source 18 so that it reduces a significant amount (e.g., at least 50%, and more preferably, at least 90%) of the shielding requirement at a building. Such feature is advantageous because it allows the radiation system 10 to be useable at any location within the building, or at any facility, with minimal retrofit to be done to the building to provide radiation shielding. In other embodiments, the shield 90 may be configured to block off all or most of the radiation resulted from an operation of the radiation source 18. In such cases, the capsule 16 may not include any shielding material.

In other embodiments, the inner support 740 may form the capsule (e.g., capsule 16), and the outer shield may be considered to be the shield 90.

In some embodiments, the shielding provided by the capsule 16 and the shield 90 has a total weight that is 4450 kg. In other embodiments, the total weight of the shielding provided by the capsule 16 and the shield 90 may be more than 4450 kg, or less than 4450 kg.

Returning to FIGS. 14A and 14B, the system 10 may optionally further include a shield cover 790 for covering the portion of the patient 42 that is outside the capsule 16. The cover 790 may be translatable into an open configuration for allowing the patient to get on/off the patient support 62, and may be translatable into a closed configuration for blocking radiation that is resulted from an operation of the radiation source 18. For example, the cover 790 may be configured to block radiation that exits from the opening 60 of the capsule 16. In other embodiments, instead of being translatable, the cover 790 may be rotated between the open and closed configurations. In some embodiments, the cover 790 may be considered to be a shield, and may have any of the features discussed previously with reference to the shield 90.

Figure 15A:
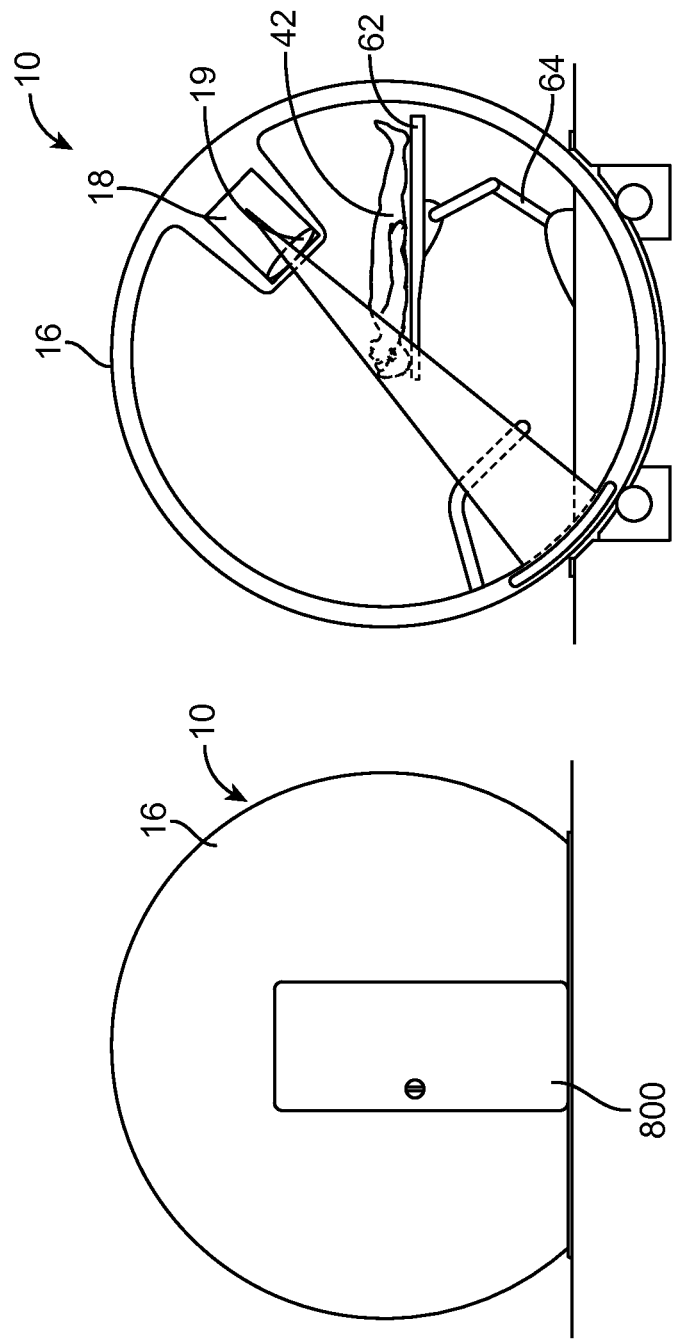
FIG. 15A illustrates another radiation system in accordance with other embodiments.
Figure 15B:
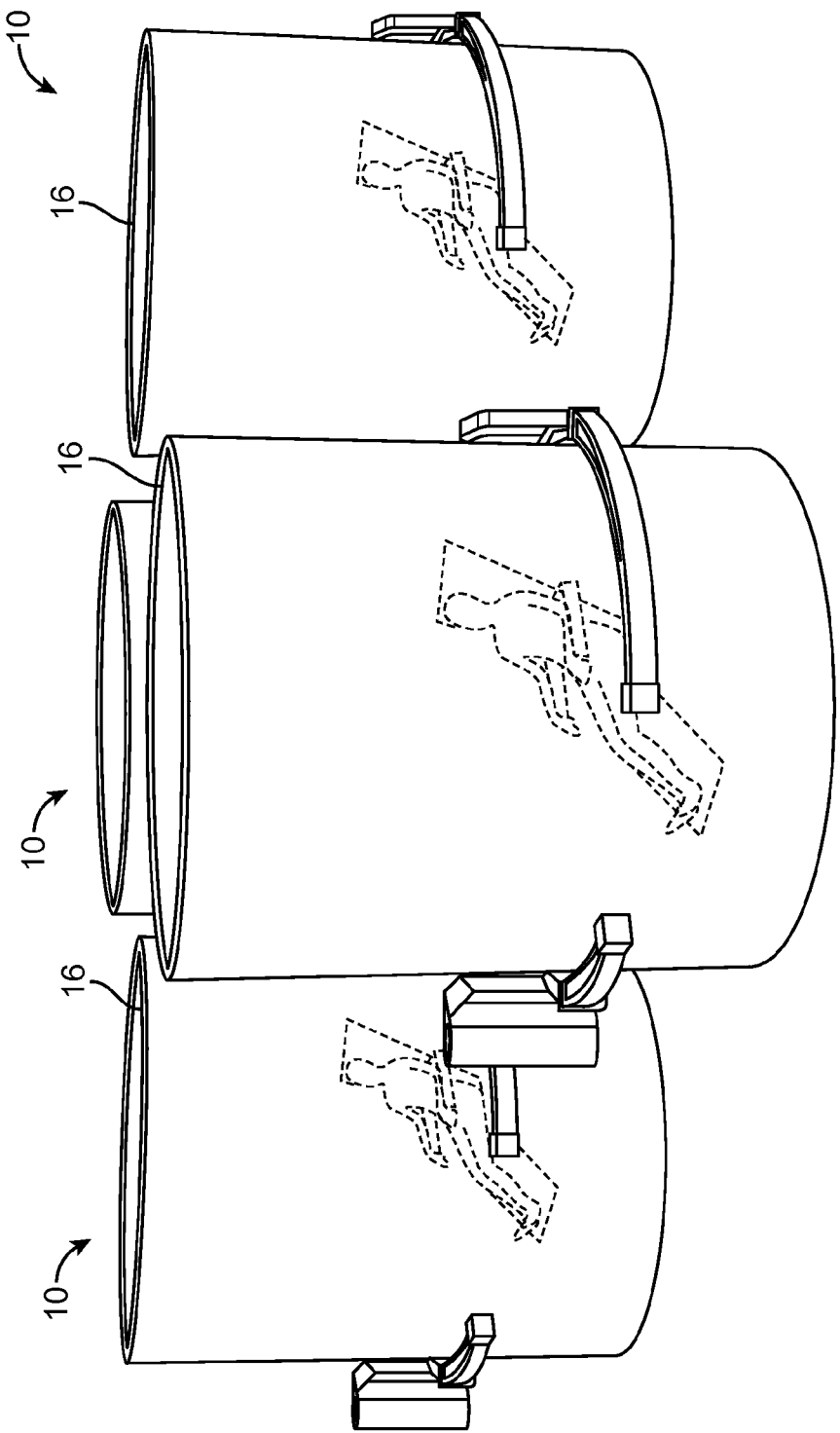
FIG. 15B illustrates another radiation system in accordance with other embodiments.

In one or more embodiments described herein (e.g., in the embodiments of FIG. 1, FIGS. 2A-2B, FIG. 3, FIG. 4, FIG. 5, FIG. 6, FIG. 7, FIG. 8, FIG. 9, FIG. 10, FIG. 11, FIG. 12, FIG. 13, or FIG. 14), the capsule 16 may have a size that completely surrounds the patient 42. FIG. 15A illustrates a radiation system 10 that includes a capsule 16 surrounding the entire patient 42 in accordance with some embodiments. The capsule 16 may have a door 800 that allows the patient 42 to enter into the space defined by the capsule 16. In some embodiments, the door 800 may itself be a shield that blocks at least part of the radiation generated from the operation of the radiation source 18. In the illustrated embodiments, the radiation source 18 of the system 10 is integrated with (e.g., fixedly coupled or moveably coupled to) the capsule 16. In other embodiments, the capsule 16 may be completely independent from the radiation source 18. For example, in other embodiments, the radiation source 18 may be part of a machine, which is encased by the capsule 16. The capsule 16 may have other shapes in other embodiments. For example, in other embodiments, the capsule 16 may have a cylindrical configuration (FIG. 15B). In the illustrated embodiments, the radiation source may be coupled to a mechanical positioner, which positions the radiation source.

In one or more embodiments described herein (e.g., in the embodiments of FIG. 1, FIGS. 2A-2B, FIG. 3, FIG. 4, FIG. 5, FIG. 6, FIG. 7, FIG. 8, FIG. 9, FIG. 10, FIG. 11, FIG. 12, FIG. 13, FIG. 14, FIG. 15), the system 10 may have a light weight and/or weight distribution. For example, in some embodiments, the system 10 may have a total weight that is less than 20 k lbs, and more preferably, less than 15 k lbs (e.g., 10 k lbs). Alternatively or additionally, in some embodiments, the system 10 may have a weight per square feet that is less than 500 lb/ft$^2$, and more preferably, less than 400 lb/ft$^2$, such as 300 lb/ft$^2$ or less (e.g., 200 lb/ft$^2$, 60 lb/ft$^2$, etc.). In further embodiments, the system 10 may have a weight per square feet that is less than 60 lb/ft$^2$. Configuring the system 10 to have a light weight and/or weight distribution is advantageous because it may obviate the need to retrofit a building in order to support the system 10. Also, such configuration may allow the system 10 to be placed in other floors that are higher than the basement. Various techniques may be employed to reduce a weight and/or a weight distribution of the system 10. For example, in some embodiments, a light weight accelerator (e.g., a X-band accelerator) may be used for the system 10. In other embodiments, other types of accelerator may be used. In one implementation, an energy requirement of the accelerator may be reduced by reducing the SID/SAD (e.g., to 800 mm or less), thereby reducing a required dose-rate output of the accelerator. This may in turn, reduce a size of the accelerator in some embodiments. In one or more embodiments described herein, the radiation source 18 may be axially translatable to reduce the SID/SAD distance. Also, in some embodiments, light weight materials may be used to make different components of the radiation system 10. In further embodiments, a desired weight distribution of the system 10 may be achieved by distributing one or more components of the system 10 over a larger surface area. For example, in some embodiments, the shielding material (e.g., the shielding material at the capsule 16 and/or at the shield(s) 90) for the radiation system 10 may be implemented using different shielding portions that are placed at different distances away from a part of the system 10. In one implementation, there may be a first shielding portion that is located closer to an isocenter of the system 10, and a second shielding portion that is located further away from the isocenter than the first shielding portion. In such cases, during a radiation procedure, radiation generated may be partially blocked by the first shielding portion, and then further blocked by the second shielding portion. Thus, in some embodiments, a radiation shielding for the system 10 may be implemented using different shielding portions (which may be considered to be parts of the capsule 16 and/or the shield 90). As long as these shielding portions are not retrofitted into the structures of a building, they may be considered to be parts of the system 10. In some embodiments, these shielding portions may be physically coupled (directly or indirectly) to components of the system 10. In other embodiments, one or more of these shielding portions may be stand-alone components that are not physically coupled to components of the system 10. Also, in some embodiments, all of the shielding for the system 10 may be located within 5 meters, and more preferably, within 3 meters, from an isocenter of the system 10.

In one or more embodiments (e.g., any of the embodiments of FIGS. 1-15), the shielding of the system 10 may be configured to achieve non-occupational exposure levels of 2 mR/hr or less in nearby uncontrolled areas of a facility (such as, within 10 meters from the system 10, and more preferably within 5 meters from the system 10, and more preferably within 3 meters from the system 10, and even more preferably within a distance of 1.5 m from the system 10—e.g., measured from an isocenter or from any surface of the system 10). Additionally, or alternatively, the shielding of the system 10 may be configured to achieve occupational exposure levels of 5 mR/hr or less are preferably achieved at the control console in the treatment room (such as, within 10 meters from the system 10, and more preferably within 5 meters from the system 10, and more preferably within 3 meters from the system 10, and even more preferably within a distance of 1.5 m from the system 10—e.g., measured from an isocenter or from any surface of the system 10). Additionally, or alternatively, in one or more embodiments (e.g., any of the embodiments of FIGS. 1-15), the shielding of the system 10 may be configured to satisfy the requirements under 10 CFR §20.1301, which prescribes dose limits for individual members of the public. For example, in some embodiments, the shielding for the system 10 may be configured so that (1) the total effective dose equivalent to individual members of the public does not exceed 0.1 rem (1 mSv) in a year, and (2) the dose in any unrestricted area from external sources does not exceed 0.002 rem (0.02 millisievert) in any one hour.

In one or more embodiments described herein, the weight of the system 10 may be less than 15000 lbs, and more preferably, less than 10000 lbs. In other embodiments, the weight of the system 10 may be more than 15000 lbs. Also, in one or more embodiments described herein, the loading to the floor due to the system 10 may be less than 500 psf, and more preferably less than 300 psf, and even more preferably 200 psf or less. In some embodiments, the support 12 of the system 10 may spread over an area that is sufficiently large so that the desired loading on the floor can be achieved. In some embodiments, the support 12 may include a gusseted frame for distributing the load down to a desirable level. Also, in one or more embodiments described herein, the system 10 may fit into an unshielded room no bigger than 15×20 ft. In other embodiments, the system 10 may fit into an unshielded room that is larger than 15×20 ft (e.g., 20×20 ft).

In one or more embodiments described herein, the energy of the electron beam (prior to bremstrahlung conversion to X-rays) provided by the radiation source of the system 10 may be anywhere from 1-6 MV, and more preferably anywhere from 1-3 MV, e.g., 2 MV (or less). In other embodiments, the energy of the electron beam may be more than 3 MV, or less than 1 MV. Also, in one or more embodiments described herein, the radiation source may include a X-Band machine, a S-Band machine, or other types of machines. Furthermore, in one or more embodiments described herein, the spot size of the beam provided by the radiation source of the system 10 may be 1 mm or less (e.g., 0.8 mm or less). In other embodiments, the spot size may be more than 1 mm. In addition, in one or more embodiments, the system 10 may be configured to deliver a dose of 75 Gy to a 5 mm diameter target (e.g., 5 mm×5 mm×5 mm volume) at 8-cm depth in under 45 minutes (e.g., 40 minutes). In other embodiments, the dose rate output may be different from the example described.

Furthermore, in one or more embodiments, the radiation source 18 may include multiple accelerators. For example, in some embodiments, the system 10 may include ten accelerators. In other embodiments, the system may include fewer than ten accelerators, or more than ten accelerators. Using multiple accelerators to implement the radiation source 18 is advantageous because they may reduce thermal stress on components of the radiation source 18. Also, using multiple accelerators to implement the radiation source 18 may allow a treatment energy requirement to be as low as 0.9 MV.

In one or more embodiments described herein, the system 10 may include a shield (e.g., shield 90 described herein) that is in a shape of a tube (like that shown in the embodiments of FIG. 3J or FIG. 14A) for covering at least a portion of the patient 42. The tube may include 18 mm (or other thickness) of Pb with steel framing, and an aesthetic fiberglass cover. In some embodiments, fresh air may be circulated in the tube using internal channels to provide a comfortable environment for the patient 42. Also, in some embodiments, light source(s) (e.g., replaceable LEDs or other types of light sources) may be provided in the tube. In further embodiments, the tube may include a sound source or a sound transmitter for transmitting sound that electronically filters out machine noise to thereby provide a quiet environment for the patient 42 while inside the tube. In some embodiments, the tube may be a single piece, or may include multiple components that are assembled together to form a tube during use. For example, in some embodiments, the system 10 may include arms that are computer controlled to move different shielding components to form a shield that encloses the patient 42. Such configuration may provide an automated shield placement. The shielding components may have overlapping surfaces (e.g., toothed edges, serrated mating surfaces, etc.) so that when they are moved to abut against each other to form a closed configuration, the overlapping surfaces of the respective shielding components may prevent leakage of radiation from within the tube.

Figure 16:
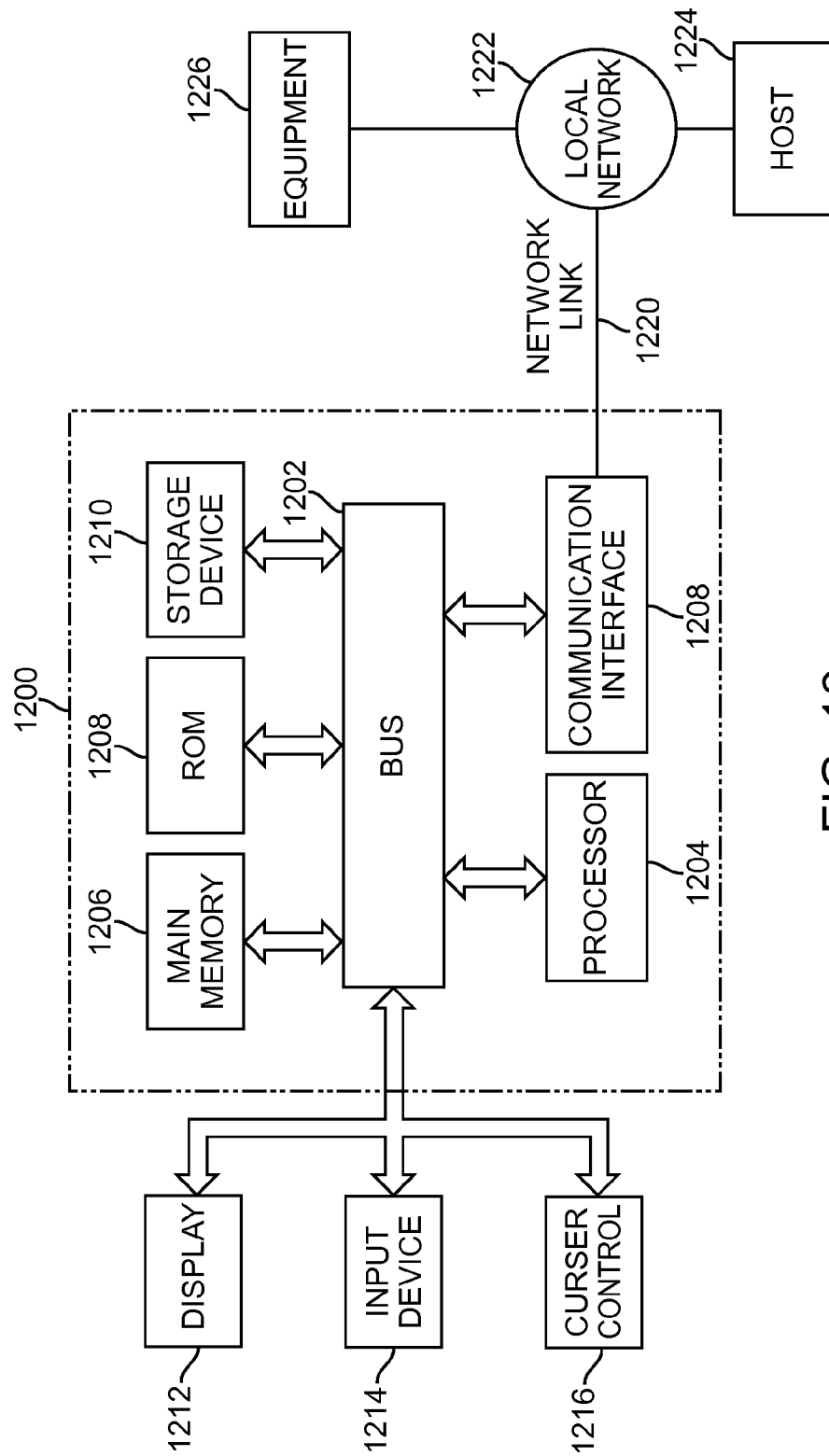
FIG. 16 illustrates an example of a computer system that may be used to implement a part of a radiation system in accordance with some embodiments.

FIG. 16 is a block diagram that illustrates an embodiment of a computer system 1200 upon which one or more components of the radiation system 10 may be implemented. In some embodiments, the computer system 1200 may be used to implement the processor 80. Computer system 1200 includes a bus 1202 or other communication mechanism for communicating information, and a processor 1204 coupled with the bus 1202 for processing information. The processor 1204 may be configured to perform various functions described herein. The computer system 1200 also includes a main memory 1206, such as a random access memory (RAM) or other dynamic storage device, coupled to the bus 1202 for storing information and instructions to be executed by the processor 1204. The main memory 1206 also may be used for storing temporary variables or other intermediate information during execution of instructions to be executed by the processor 1204. The computer system 1200 further includes a read only memory (ROM) 1208 or other static storage device coupled to the bus 1202 for storing static information and instructions for the processor 1204. A data storage device 1210, such as a magnetic disk or optical disk, is provided and coupled to the bus 1202 for storing information and instructions.

The computer system 1200 may be coupled via the bus 1202 to a display 1212, such as a cathode ray tube (CRT) or a flat panel, for displaying information to a user. An input device 1214, including alphanumeric and other keys, is coupled to the bus 1202 for communicating information and command selections to processor 1204. Another type of user input device is cursor control 1216, such as a mouse, a trackball, or cursor direction keys for communicating direction information and command selections to processor 1204 and for controlling cursor movement on display 1212. This input device typically has two degrees of freedom in two axes, a first axis (e.g., x) and a second axis (e.g., y), that allows the device to specify positions in a plane.

The computer system 1200 may be used for performing various functions in accordance with the embodiments described herein. According to one embodiment, such use is provided by computer system 1200 in response to processor 1204 executing one or more sequences of one or more instructions contained in the main memory 1206. Such instructions may be read into the main memory 1206 from another computer-readable medium, such as storage device 1210. Execution of the sequences of instructions contained in the main memory 1206 causes the processor 1204 to perform the process steps described herein. One or more processors in a multi-processing arrangement may also be employed to execute the sequences of instructions contained in the main memory 1206. In alternative embodiments, hard-wired circuitry may be used in place of or in combination with software instructions to implement the invention. Thus, embodiments of the processor described herein are not limited to any specific combination of hardware circuitry and software.

The term "computer-readable medium" as used herein refers to any medium that participates in providing instructions to the processor 1204 for execution. Such a medium may take many forms, including but not limited to, non-volatile media, volatile media, and transmission media. Non-volatile media (an example of non-transitory media) includes, for example, optical or magnetic disks, such as the storage device 1210. Volatile media (another example of non-transitory media) includes dynamic memory, such as the main memory 1206. Transmission media includes coaxial cables, copper wire and fiber optics, including the wires that comprise the bus 1202. Transmission media can also take the form of acoustic or light waves, such as those generated during radio wave and infrared data communications.

Common forms of computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, a PROM, and EPROM, a FLASH-EPROM, any other memory chip or cartridge, a carrier wave as described hereinafter, or any other medium from which a computer can read.

Various forms of computer-readable media may be involved in carrying one or more sequences of one or more instructions to the processor 1204 for execution. For example, the instructions may initially be carried on a magnetic disk of a remote computer. The remote computer can load the instructions into its dynamic memory and send the instructions over a telephone line using a modem. A modem local to the computer system 1200 can receive the data on the telephone line and use an infrared transmitter to convert the data to an infrared signal. An infrared detector coupled to the bus 1202 can receive the data carried in the infrared signal and place the data on the bus 1202. The bus 1202 carries the data to the main memory 1206, from which the processor 1204 retrieves and executes the instructions. The instructions received by the main memory 1206 may optionally be stored on the storage device 1210 either before or after execution by the processor 1204.

The computer system 1200 also includes a communication interface 1218 coupled to the bus 1202. The communication interface 1218 provides a two-way data communication coupling to a network link 1220 that is connected to a local network 1222. For example, the communication interface 1218 may be an integrated services digital network (ISDN) card or a modem to provide a data communication connection to a corresponding type of telephone line. As another example, the communication interface 1218 may be a local area network (LAN) card to provide a data communication connection to a compatible LAN. Wireless links may also be implemented. In any such implementation, the communication interface 1218 sends and receives electrical, electromagnetic or optical signals that carry data streams representing various types of information.

The network link 1220 typically provides data communication through one or more networks to other devices. For example, the network link 1220 may provide a connection through local network 1222 to a host computer 1224 or to equipment 1226 such as a radiation beam source or a switch operatively coupled to a radiation beam source. The data streams transported over the network link 1220 can comprise electrical, electromagnetic or optical signals. The signals through the various networks and the signals on the network link 1220 and through the communication interface 1218, which carry data to and from the computer system 1200, are exemplary forms of carrier waves transporting the information. The computer system 1200 can send messages and receive data, including program code, through the network(s), the network link 1220, and the communication interface 1218.

Although particular embodiments have been shown and described, it will be understood that they are not intended to limit the claimed inventions, and it will be obvious to those skilled in the art that various changes and modifications may be made without departing from the spirit and scope of the claimed inventions. The specification and drawings are, accordingly, to be regarded in an illustrative rather than restrictive sense. The claimed inventions are intended to cover alternatives, modifications, and equivalents.

The invention claimed is:

1. A radiation system, comprising:
a first support;
a first structure rotatably coupled to the first support so that the first structure is rotatable about a first axis relative to the first support;
a second structure rotatably coupled to the first structure so that the second structure is rotatable about a second axis that forms a non-zero angle relative to the first structure; and
a first radiation source connected to the second structure;
wherein the first structure and the second structure are parts of a container comprising a cavity for accommodating at least a portion of a patient, wherein the container comprises a wall portion that intersects a longitudinal axis of the patient, wherein the wall portion is a part of the first structure and/or a part of the second structure.

2. The system of claim 1, wherein the first structure comprises a first space, the second structure comprises a second space, and the first space and the second space are configured to collectively form the cavity to accommodate the at least a portion of the patient.

3. The system of claim 1, wherein the first radiation source is configured to rotate within a rotational plane about the second axis by rotating the second structure relative to the first structure about the second axis; and
wherein an angle between the rotational plane and the first axis is adjustable by rotation of the first structure about the first axis.

4. The system of claim 1, further comprising a beam stopper connected to the second structure.

5. The system of claim 1, wherein the first radiation source is configured to deliver treatment energy.

6. The system of claim 1, further comprising:
a second radiation source connected to the second structure; and
an imager connected to the second structure;
wherein the first radiation source is configured to deliver treatment radiation;
wherein the second radiation source is configured to deliver diagnostic radiation; and
wherein the first radiation source, the second radiation source, and the imager are rotatable relative to the first structure by movement of the second structure.

7. The system of claim 1, wherein the second structure includes a shielding material that is configured to block at least 98% of radiation resulted from an operation of the first radiation source.

8. A radiation system, comprising:
a first support;
a first structure rotatably coupled to the first support so that the first structure is rotatable about a first axis relative to the first support;
a second structure rotatably coupled to the first structure so that the second structure is rotatable about a second axis that forms a non-zero angle relative to the first structure; and
a first radiation source connected to the second structure;
wherein the first structure and the second structure are parts of a capsule comprising a cavity for accommodating at least a portion of a patient; and
wherein the radiation system further comprises a third structure rotatably coupled to the second structure, wherein the second structure is rotatable relative to both the first and the third structures about the second axis.

9. The system of claim 8, further comprising a second support for supporting the third structure.

10. The system of claim 8, wherein the first structure and the third structure are configured to rotate simultaneously relative to the second structure, or vice versa.

11. A radiation system, comprising:
a first support;
a first structure rotatably coupled to the first support so that the first structure is rotatable about a first axis relative to the first support;
a second structure rotatably coupled to the first structure so that the second structure is rotatable about a second axis that forms a non-zero angle relative to the first structure; and
a first radiation source connected to the second structure;
wherein the first structure and the second structure are parts of a capsule comprising a cavity for accommodating at least a portion of a patient; and
wherein the first structure has an interface plane that interfaces with the second structure, the interface plane forming an acute angle with respect to the first axis.

12. A radiation system, comprising:
a first support;
a first structure rotatably coupled to the first support so that the first structure is rotatable about a first axis relative to the first support;
a second structure rotatably coupled to the first structure so that the second structure is rotatable about a second axis; and
a first radiation source connected to the second structure;
wherein the first radiation source is configured to rotate within a rotational plane about the second axis by rotating the second structure relative to the first structure about the second axis; and wherein an angle between the rotational plane and the first axis is adjustable by rotation of the first structure about the first axis.

13. The system of claim 12, wherein the first structure comprises a first space, the second structure comprises a second space, and the first space and the second space are configured to collectively accommodate at least a portion of a patient.

14. The system of claim 12, wherein the first radiation source is configured to deliver treatment energy.

15. The system of claim 12, further comprising:
a second radiation source connected to the second structure; and
an imager connected to the second structure;
wherein the first radiation source is configured to deliver treatment radiation;
wherein the second radiation source is configured to deliver diagnostic radiation; and
wherein the first radiation source, the second radiation source, and the imager are rotatable relative to the first structure by movement of the second structure.

16. The system of claim 12, wherein the second structure includes a shielding material that is configured to block at least 98% of radiation resulted from an operation of the first radiation source.

17. A radiation system, comprising:
a first support;
a first structure rotatably coupled to the first support so that the first structure is rotatable about a first axis relative to the first support;
a second structure rotatably coupled to the first structure so that the second structure is rotatable about a second axis; and
a first radiation source connected to the second structure;
wherein the first radiation source is configured to rotate within a rotational plane about the second axis by rotating the second structure relative to the first structure about the second axis;
wherein an angle between the rotational plane and the first axis is adjustable by rotation of the first structure about the first axis; and
wherein the radiation system further comprises a third structure rotatably coupled to the second structure, wherein the second structure is rotatable relative to both the first and the third structures about the second axis.

18. The system of claim 17, further comprising a second support for supporting the third structure.

19. The system of claim 17, wherein the first structure and the third structure are configured to rotate simultaneously relative to the second structure, or vice versa.

20. A radiation system, comprising:
a first support;
a first structure rotatably coupled to the first support so that the first structure is rotatable about a first axis relative to the first support;
a second structure rotatably coupled to the first structure so that the second structure is rotatable about a second axis; and
a first radiation source connected to the second structure;
wherein the first radiation source is configured to rotate within a rotational plane about the second axis by rotating the second structure relative to the first structure about the second axis;
wherein an angle between the rotational plane and the first axis is adjustable by rotation of the first structure about the first axis; and
wherein the first structure has an interface plane that interfaces with the second structure, the interface plane forming an acute angle with respect to the first axis.

* * * * *